US012662470B2

(12) United States Patent
Beck et al.

(10) Patent No.: US 12,662,470 B2
(45) Date of Patent: Jun. 23, 2026

(54) HYDROXY AND (HALO)ALKOXY SUBSTITUTED TETRAHYDROFURANS AS MODULATORS OF SODIUM CHANNELS

(71) Applicant: VERTEX PHARMACEUTICALS INCORPORATED, Boston, MA (US)

(72) Inventors: Elizabeth Mary Beck, Abingdon (GB); Robert Pullin, Oxford (GB); Gorka Etxebarria Jardi, Badalona (ES); Dean Stamos, Lexington, MA (US); Yvonne Schmidt, San Diego, CA (US); Joseph Pontillo, San Diego, CA (US); Stephen Andrew Thomson, Durham, NC (US); David Matthew Shaw, Oxford (GB); Nadia M. Ahmad, Hayes (GB); Lidio Marx Carvalho Meireles, San Marcos, CA (US); Sarah Skerratt, Cambridge (GB); Sara S. Hadida Ruah, La Jolla, CA (US); Timothy Donald Neubert, San Diego, CA (US); Dennis James Hurley, San Marcos, CA (US); Steven John Durrant, Headington (GB); Christopher Wray, Berkshire (GB); Anisa Nizarali Virani, Thatcham (GB); Kiri North, Oxford (GB); Bhairavi Galan, Abingdon (GB); Ronald Marcellus Knegtel, Abingdon (GB); Ewa Iwona Chudyk, Wantage (GB); Joanne Louise Pinder, Didcot (GB); Bruno Artur Sousa, Reading (GB); Francoise Pierard, Abingdon (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 296 days.

(21) Appl. No.: 18/566,305

(22) PCT Filed: Jun. 3, 2022

(86) PCT No.: PCT/US2022/072758

§ 371 (c)(1),
(2) Date: Dec. 1, 2023

(87) PCT Pub. No.: WO2022/256842

PCT Pub. Date: Dec. 8, 2022

(65) Prior Publication Data

US 2024/0294512 A1 Sep. 5, 2024

Related U.S. Application Data

(60) Provisional application No. 63/197,141, filed on Jun. 4, 2021.

(51) Int. Cl.
*C07D 405/12* (2006.01)
*A61K 31/443* (2006.01)
*A61K 31/501* (2006.01)

(52) U.S. Cl.
CPC .......... *C07D 405/12* (2013.01); *A61K 31/443* (2013.01); *A61K 31/501* (2013.01)

(58) Field of Classification Search
CPC .. C07D 405/12; A61K 31/443; A61K 31/501; A61P 29/00
See application file for complete search history.

(56) References Cited

U.S. PATENT DOCUMENTS 5,304,121 A 4/1994 Sahatjian
5,886,026 A 3/1999 Hunter et al.
(Continued)

FOREIGN PATENT DOCUMENTS

CN 111217776 6/2020
CN 111808019 10/2020
(Continued)

OTHER PUBLICATIONS

Parella et al. J. Org. Chem. 2015, 80, 4, 2339-2355. (Year: 2015).*
(Continued)

*Primary Examiner* — Matthew P Coughlin
*Assistant Examiner* — Ashli A Chicks
(74) *Attorney, Agent, or Firm* — Barnes & Thornburg LLP

(57) ABSTRACT

Compounds of formula I and pharmaceutically acceptable salts thereof, useful as inhibitors of sodium channels are provided. Also provided are pharmaceutical compositions comprising the compounds or pharmaceutically acceptable
(Continued)

salts and methods of using the compounds, pharmaceutically acceptable salts, and pharmaceutical compositions in the treatment of various disorders, including pain.

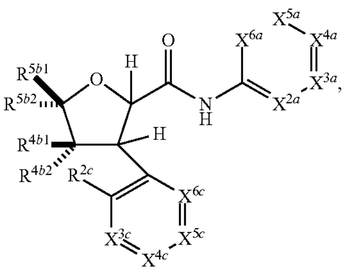

I

20 Claims, 3 Drawing Sheets

(56) References Cited

U.S. PATENT DOCUMENTS

| | | | |
|---|---|---|---|
| 6,099,562 | A | 8/2000 | Ding et al. |
| 8,389,734 | B2 | 3/2013 | Chen et al. |
| 8,466,188 | B2 | 6/2013 | Chafeev et al. |
| 8,519,137 | B2 | 8/2013 | Joshi et al. |
| 8,779,197 | B2 | 7/2014 | Chen et al. |
| 8,841,483 | B2 | 9/2014 | Joshi et al. |
| 8,865,771 | B2 | 10/2014 | Chen et al. |
| 8,883,840 | B2 | 11/2014 | Chafeev et al. |
| 9,051,270 | B2 | 6/2015 | Hadida-Ruah et al. |
| 9,108,903 | B2 | 8/2015 | Hadida-Ruah et al. |
| 9,139,529 | B2 | 9/2015 | Hadida-Ruah et al. |
| 9,163,042 | B2 | 10/2015 | Anderson et al. |
| 9,393,235 | B2 | 7/2016 | Hadida-Ruah et al. |
| 9,421,196 | B2 | 8/2016 | Hadida-Ruah et al. |
| 9,464,102 | B2 | 10/2016 | Anderson et al. |
| 9,758,483 | B2 | 9/2017 | Hadida-Ruah et al. |
| 9,783,501 | B2 | 10/2017 | Hadida-Ruah et al. |
| 9,828,397 | B2 | 11/2017 | Anderson et al. |
| 10,087,143 | B2 | 10/2018 | Hadida-Ruah et al. |
| 10,253,054 | B2 | 4/2019 | Anderson et al. |
| 10,647,661 | B2 | 5/2020 | Ahmad et al. |
| 10,738,009 | B2 | 8/2020 | Hadida-Ruah et al. |
| 10,787,472 | B2 | 9/2020 | Anderson et al. |
| 11,203,571 | B2 | 12/2021 | Hadida-Ruah et al. |
| 11,358,977 | B2 | 6/2022 | Jiang et al. |
| 11,529,337 | B2 | 12/2022 | Agarwal et al. |
| 11,603,351 | B2 | 3/2023 | Ahmad et al. |
| 11,673,864 | B2 | 6/2023 | Hadida-Ruah et al. |
| 11,773,119 | B2 | 10/2023 | Anderson et al. |
| 11,827,627 | B2 | 11/2023 | Beck et al. |
| 11,834,441 | B2 | 12/2023 | Durrant et al. |
| 11,919,887 | B2 | 3/2024 | Durrant et al. |
| 2004/0006237 | A1 | 1/2004 | Dolitzky et al. |
| 2007/0238733 | A1 | 10/2007 | Joshi et al. |
| 2008/0312235 | A1 | 12/2008 | Lane et al. |
| 2009/0048306 | A1 | 2/2009 | Bagal et al. |
| 2009/0099233 | A1 | 4/2009 | Joshi et al. |
| 2009/0118333 | A1 | 5/2009 | Chen et al. |
| 2009/0118338 | A1 | 5/2009 | Chen et al. |
| 2011/0306607 | A1 | 12/2011 | Hadida-Ruah et al. |
| 2012/0196869 | A1 | 8/2012 | Hadida Ruah et al. |
| 2012/0220605 | A1 | 8/2012 | Pajouhesh et al. |
| 2012/0245136 | A1 | 9/2012 | Hadida-Ruah et al. |
| 2012/0264749 | A1 | 10/2012 | Hadida-Ruah et al. |
| 2013/0231370 | A1 | 9/2013 | Chen et al. |
| 2013/0274243 | A1 | 10/2013 | Bagal et al. |
| 2013/0303535 | A1 | 11/2013 | Tsuboi et al. |
| 2014/0187533 | A1 | 7/2014 | Pajouhesh et al. |
| 2014/0213616 | A1 | 7/2014 | Hadida-Ruah et al. |
| 2014/0221435 | A1 | 8/2014 | Hadida-Ruah et al. |
| 2014/0228371 | A1 | 8/2014 | Hadida-Ruah et al. |
| 2014/0296313 | A1 | 10/2014 | Bagal et al. |
| 2015/0005304 | A1 | 1/2015 | Hadida-Ruah et al. |
| 2015/0166589 | A1 | 6/2015 | Anderson et al. |
| 2015/0246028 | A1 | 9/2015 | Hadida-Ruah et al. |
| 2015/0336945 | A1 | 11/2015 | Hadida-Ruah et al. |
| 2016/0009743 | A1 | 1/2016 | Anderson et al. |
| 2016/0152561 | A1 | 6/2016 | Hadida-Ruah et al. |
| 2016/0376295 | A1 | 12/2016 | Anderson et al. |
| 2017/0037009 | A1 | 2/2017 | Hadida-Ruah et al. |
| 2018/0016235 | A1 | 1/2018 | Hadida-Ruah et al. |
| 2018/0044361 | A1 | 2/2018 | Anderson et al. |
| 2019/0016671 | A1 | 1/2019 | Ahmad et al. |
| 2019/0248745 | A1 | 8/2019 | Hadida-Ruah et al. |
| 2019/0276483 | A1 | 9/2019 | Anderson et al. |
| 2019/0343817 | A1 | 11/2019 | Agarwal et al. |
| 2020/0140411 | A1 | 5/2020 | Arasappan et al. |
| 2020/0377535 | A1 | 12/2020 | Anderson et al. |
| 2021/0047271 | A1 | 2/2021 | Hadida-Ruah et al. |
| 2021/0052610 | A1 | 2/2021 | Agarwal et al. |
| 2021/0094906 | A1 | 4/2021 | Ahmad et al. |
| 2021/0155643 | A1 | 5/2021 | Jiang et al. |
| 2021/0198241 | A1 | 7/2021 | Durrant |
| 2022/0110923 | A1 | 4/2022 | Thomson |
| 2023/0009251 | A1 | 1/2023 | Beck |
| 2023/0062053 | A1 | 3/2023 | Thomson |
| 2023/0286907 | A1 | 9/2023 | Ahmad et al. |
| 2023/0286961 | A1 | 9/2023 | Durrant et al. |
| 2023/0373925 | A1 | 11/2023 | Miller et al. |
| 2023/0382910 | A1 | 11/2023 | Miller et al. |
| 2024/0182455 | A1 | 6/2024 | Beck et al. |

FOREIGN PATENT DOCUMENTS

| | | | |
|---|---|---|---|
| CN | 112225695 | | 1/2021 |
| CN | 112300051 | | 2/2021 |
| CN | 112300069 | | 2/2021 |
| CN | 112390745 | | 2/2021 |
| CN | 112441969 | | 3/2021 |
| CN | 112457294 | | 3/2021 |
| CN | 112479996 | | 3/2021 |
| JP | 2004-509881 | A | 4/2004 |
| WO | WO 2002/008748 | A3 | 1/2002 |
| WO | 02/24673 | A | 3/2002 |
| WO | WO 2006/011050 | A2 | 2/2006 |
| WO | WO 2008/135826 | A2 | 11/2008 |
| WO | WO 2010/129864 | A2 | 11/2010 |
| WO | WO 2011/026240 | A1 | 3/2011 |
| WO | WO 2011/140425 | A1 | 11/2011 |
| WO | WO 2012/106499 | A1 | 8/2012 |
| WO | WO 2012/112743 | A1 | 8/2012 |
| WO | WO 2012/116440 | A1 | 9/2012 |
| WO | WO 2012/125613 | A1 | 9/2012 |
| WO | WO 2013/061205 | A2 | 5/2013 |
| WO | WO 2013/086229 | A1 | 6/2013 |
| WO | WO 2013/109521 | A1 | 7/2013 |
| WO | WO 2013/114250 | A1 | 8/2013 |
| WO | WO 2013/131018 | A1 | 9/2013 |
| WO | WO 2013/134518 | A1 | 9/2013 |
| WO | WO 2014/120808 | A1 | 8/2014 |
| WO | WO 2014/120815 | A1 | 8/2014 |
| WO | WO 2014/120820 | A1 | 8/2014 |
| WO | WO 2014/201206 | A1 | 12/2014 |
| WO | WO 2015/010065 | A1 | 1/2015 |
| WO | WO 2015/089361 | A1 | 6/2015 |
| WO | WO 2015/157559 | A2 | 10/2015 |
| WO | WO 2016/141035 | A1 | 9/2016 |
| WO | WO 2017/059385 | A1 | 4/2017 |
| WO | WO 2018/183781 | A1 | 10/2018 |
| WO | WO 2018/183782 | A1 | 10/2018 |
| WO | WO 2018/213426 | A1 | 11/2018 |
| WO | WO 2019/014352 | A1 | 1/2019 |
| WO | WO 2020/014243 | A1 | 1/2020 |
| WO | WO 2020/014246 | A1 | 1/2020 |
| WO | WO 2020/072835 | A1 | 4/2020 |
| WO | WO 2020/092187 | A1 | 5/2020 |
| WO | WO 2020/092667 | A1 | 5/2020 |

(56) References Cited

FOREIGN PATENT DOCUMENTS

| | | |
|---|---|---|
| WO | WO 2020/117626 A1 | 6/2020 |
| WO | WO 2020/140959 A1 | 7/2020 |
| WO | WO 2020/146612 A1 | 7/2020 |
| WO | WO 2020/146682 A1 | 7/2020 |
| WO | WO 2020/151728 A1 | 7/2020 |
| WO | WO 2020/261114 A1 | 12/2020 |
| WO | WO 2021/032074 A1 | 2/2021 |
| WO | WO 2021/047622 A1 | 3/2021 |
| WO | WO 2021/113627 A1 | 6/2021 |
| WO | WO 2021/252818 A1 | 12/2021 |
| WO | WO 2021/252820 A1 | 12/2021 |
| WO | WO 2021/252822 A1 | 12/2021 |
| WO | WO 2021/257418 A1 | 12/2021 |
| WO | WO 2021/257420 A1 | 12/2021 |
| WO | WO 2021/257490 A1 | 12/2021 |
| WO | WO 2022/036297 A1 | 2/2022 |
| WO | WO 2022/037641 A1 | 2/2022 |
| WO | WO 2022/037647 A1 | 2/2022 |

OTHER PUBLICATIONS

Akopian, A.N., L. Sivilotti, and J.N. Wood, "A tetrodotoxin-resistant voltage-gated sodium channel expressed by sensory neurons." *Nature*, 1996. 379(6562): pp. 257-262.).

Berge S.M., et al. "Pharmaceutical Salts," *J. Pharmaceutical Sciences*, 66, (Jan. 1977), pp. 1-19.

Black, J.A., et al., "Multiple sodium channel isoforms and mitogen-activated protein kinases are present in painful human neuromas." *Ann Neurol*, 2008. 64(6): pp. 644-653.

Blair, N.T. and B.P. Bean, "Roles of tetrodotoxin (TTX)-sensitive Na+ current, TTX-resistant Na+ current, and Ca2+ current in the action potentials of nociceptive sensory neurons." *J Neurosci.*, 2002. 22(23): pp. 10277-10290).

CAS No. 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione.

CAS No. 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl]ester).

Catterall, W. A., Goldin, A. L., and Waxman, S. G., International Union of Pharmacology. XLVII. "Nomenclature and structure-function relationships of voltage-gated sodium channels." *Pharmacol Rev* 57 (4), pp. 397 (2005).

Chahine, M., Chatelier, A., Babich, O., and Krupp, J. J., "Voltage-gated sodium channels in neurological disorders." *CNS Neurol Disord Drug Targets* 7 (2), pp. 144-158 (2008).

Choi, J.S. and S.G. Waxman, "Physiological interactions between NaV1.7 and NaV1.8 sodium channels: a computer simulation study." *J Neurophysiol.* 106(6): pp. 3173-3184.

Coward, K., et al., "Immunolocalization of SNS/PN3 and NaN/SNS2 sodium channels in human pain states." *Pain*, 2000. 85(1-2): pp. 41-50.

Dieleman, J.P., et al., "Incidence rates and treatment of neuropathic pain conditions in the general population." *Pain*, 2008. 137(3): pp. 681-688.

Dong, X.W., et al., "Small interfering RNA-mediated selective knockdown of Na(V)1.8 tetrodotoxin-resistant sodium channel reverses mechanical allodynia in neuropathic rats." *Neuroscience*, 2007. 146(2): pp. 812-821.

England, S., "Voltage-gated sodium channels: the search for subtype-selective analgesics." *Expert Opin Investig Drugs* 17 (12), pp. 1849-64 (2008).

Fornwald, J.A. et al., "Gene Expression in Mammalian Cells Using BacMam, a Modified Baculovirus System," *Methods in Molecular Biology*, 1350, (2016), pp. 95-116.

Gonzalez, J.E. and Tsien, R.Y. Improved indicators of cell membrane potential that use fluorescence resonance energy transfer, *Chem. Biol.* 4, (1997), pp. 269-277.

Gonzalez, J.E. and Tsien, R.Y. "Voltage Sensing by Fluorescence Resonance Energy Transfer in Single Cells," *Biophys. J.* 69, (Oct. 1995), pp. 1272-1280.

Harbeson, S.L. and R. D. Tung, "Deuterium In Drug Discovery and Development," *Ann. Rep. Med. Chem.*, 46, (2011), pp. 403-417.

Huang, C.J. et al. "Characterization of voltage-gated sodium channel blockers by electrical stimulation and fluorescence detection of membrane potential," *Nature Biotech.* 24, 4, (Apr. 2006), pp. 439-446.

Huang, H.L., et al., "Proteomic profiling of neuromas reveals alterations in protein composition and local protein synthesis in hyper-excitable nerves." *Mol Pain*, 2008. 4: p. 33.

International Search Report and Written Opinion for PCT/US2022/032238, September 26, 2022, 14 pgs.

Iqbal et al., "Diabetic Peripheral Neuropathy: Epidemiology, Diagnosis, and Pharmacotherapy", Clin. Ther., 2018 40(6): pp. 828-849.

Jarvis, M.F., et al., "A-803467, a potent and selective $Na_v$1.8 sodium channel blocker, attenuates neuropathic and inflammatory pain in the rat." *Proc Natl Acad Sci. U S A*, May 15, 2007. 104(20): pp. 8520-8525.

Joshi, S.K., et al., "Involvement of the TTX-resistant sodium channel Nav1.8 in inflammatory and neuropathic, but not post-operative, pain states." Pain, 2006. 123(1-2): pp. 75-82.

Krafte, D. S. and Bannon, A. W., "Sodium channels and nociception: recent concepts and therapeutic opportunities." *Curr Opin Pharmacol* 8 (1), pp. 50-56 (2008).

Lai, J., et al., "Inhibition of neuropathic pain by decreased expression of the tetrodotoxin-resistant sodium channel, NaV1.8." *Pain*, 2002. 95(1-2): pp. 143-152.

Qiu, F., et al., "Increased expression of tetrodotoxin-resistant sodium channels NaV1.8 and NaV1.9 within dorsal root ganglia in a rat model of bone cancer pain." *Neurosci. Lett.* 512(2012): pp. 61-66).

Renganathan, M., T.R. Cummins, and S.G. Waxman, "Contribution of Na(V)1.8 sodium channels to action potential electrogenesis in DRG neurons." *J Neurophysiol.*, 2001. 86(2): pp. 629-640.

Roza, C., et al., "The tetrodotoxin-resistant Na+ channel NaV1.8 is essential for the expression of spontaneous activity in damaged sensory axons of mice." *J Physiol.*, 2003. 550(Pt 3): pp. 921-926).

Ruangsri, S., et al., "Relationship of axonal voltage-gated sodium channel 1.8 (NaV1.8) mRNA accumulation to sciatic nerve injury-induced painful neuropathy in rats." *J Biol Chem.* 286(46): 2011, pp. 39836-39847).

Rush, A.M., et al., "A single sodium channel mutation produces hyper- or hypoexcitability in different types of neurons." *Proc Natl Acad Sci USA*, 2006. 103(21): pp. 8245-8250).

Rush, A.M. and T.R. Cummins, "Painful Research: Identification of a Small-Molecule Inhibitor that Selectively Targets NaV1.8 Sodium Channels." *Mol Interv*, 2007. 7(4): pp. 192-195).

Soderpalm, B., "Anticonvulsants: aspects of their mechanisms of action." *Eur J Pain* 6 Suppl A, pp. 3-9 (2002).

Strickland, I.T., et al., "Changes in the expression of NaV1.7, NaV1.8 and NaV1.9 in a distinct population of dorsal root ganglia innervating the rat knee joint in a model of chronic inflammatory joint pain." *Eur J Pain*, 2008. 12(5): pp. 564-572.

Sun, W., et al., "Reduced conduction failure of the main axon of polymodal nociceptive C-fibres contributes to painful diabetic neuropathy in rats." *Brain.* 135(Pt 2): Jan. 2012, pp. 359-375.

Wang, G. K., Mitchell, J., and Wang, S. Y., "Block of persistent late Na+ currents by antidepressant sertraline and paroxetine." *J Membr Biol* 222 (2), pp. 79-90 (2008).

Yiangou, Y., et al., "SNS/PN3 and SNS2/NaN sodium channel-like immunoreactivity in human adult and neonate injured sensory nerves." *FEBS Lett*, 2000. 467(2-3): pp. 249-252.

* cited by examiner

HYDROXY AND (HALO)ALKOXY SUBSTITUTED TETRAHYDROFURANS AS MODULATORS OF SODIUM CHANNELS

CROSS-REFERENCE TO RELATED APPLICATIONS

This application is a National Stage application of International Application No. PCT/US2022/072758, filed Jun. 3, 2022, which application claims the benefit of U.S. Provisional Application No. 63/197,141, filed Jun. 4, 2021, which is incorporated by reference herein in its entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain,* 2008. 137(3): p. 681-8). Neuropathic pain can be divided into two categories, pain caused by generalized metabolic damage to the nerve and pain caused by a discrete nerve injury. The metabolic neuropathies include post-herpetic neuropathy, diabetic neuropathy, and drug-induced neuropathy. Discrete nerve injury indications include post-amputation pain, post-surgical nerve injury pain, and nerve entrapment injuries like neuropathic back pain. Neuropathic pain is a major cause of disability worldwide, negatively affecting patient's sleep, mood, and functionality. *Clin. Ther.,* 2018 40(6): p. 828-49.

Voltage-gated sodium channels ($Na_V$s) are involved in pain signaling. $Na_V$s mediate the rapid upstroke of the action potential of many excitable cell types (e.g. neurons, skeletal myocytes, cardiac myocytes), and thus are involved in the initiation of electrical signaling in those cells (Hille, Bertil, *Ion Channels of Excitable Membranes*, Third ed. (Sinauer Associates, Inc., Sunderland, M A, 2001)). Support for the assertion that $Na_V$s play a critical and central role in pain signaling arises from (1) evaluation of the role $Na_V$s plays in normal physiology, (2) pathological states arising from mutations in the $Na_V$1.8 gene (SCN10A). (3) preclinical work in animal models, and (4) pharmacology of known $Na_V$1.8-modulating agents. In addition, because $Na_V$1.8 expression is restricted to peripheral neurons, particularly those that sense pain (e.g., the dorsal root ganglia), $Na_V$1.8 inhibitors are less likely to be associated with the side effects commonly observed with other sodium channel modulators and the abuse liability associated with opioid therapies. Therefore, targeting the underlying biology of pain through selective $Na_V$1.8 inhibition represents a novel approach to analgesic drug development that has the potential to address an urgent unmet need for safe and effective acute and chronic pain therapies (Rush, A. M. and T. R. Cummins, *Painful Research: Identification of a Small-Molecule Inhibitor that Selectively Targets $Na_V$1.8 Sodium Channels.* Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). Because of the role $Na_V$s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_V$s form a subfamily of the voltage-gated ion channel super-family and comprises 9 isoforms, designated $Na_V$1.1-$Na_V$1.9. The tissue localizations of the nine isoforms vary. $Na_V$1.4 is the primary sodium channel of skeletal muscle, and $Na_V$1.5 is the primary sodium channel of cardiac myocytes. $Na_V$s 1.7, 1.8 and 1.9 are primarily localized to the peripheral nervous system, while $Na_V$s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V$1.8 channels were identified as likely targets for analgesia (Akopian, A. N., L. Sivilotti, and J. N. Wood, A tetrodotoxin-resistant voltage-gated sodium channel expressed by sensory neurons. *Nature,* 1996. 379 (6562): p. 257-62). Since then, $Na_V$1.8 has been shown to be a carrier of the sodium current that maintains action potential firing in small dorsal root ganglia (DRG) neurons (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J. Neurosci.,* 2002. 22(23): p. 10277-90). $Na_V$1.8 is involved in spontaneous firing in damaged neurons, like those that drive neuropathic pain (Roza, C., et al., The tetrodotoxin-resistant $Na^+$ channel $Na_V$1.8 is essential for the expression of spontaneous activity in damaged sensory axons of mice. *J. Physiol.,* 2003. 550 (Pt 3): p. 921-6; Jarvis, M. F., et al., A-803467, a potent and selective $Na_V$1.8 sodium channel blocker, attenuates neuropathic and inflammatory pain in the rat. *Proc. Natl. Acad. Sci. USA,* 2007. 104(20): p. 8520-5; Joshi, S. K., et al., Involvement of the TTX-resistant sodium channel $Na_V$1.8 in inflammatory and neuropathic, but not post-operative, pain states. *Pain,* 2006. 123(1-2): pp. 75-82; Lai, J., et al., Inhibition of neuropathic pain by decreased expression of the tetrodotoxin-resistant sodium channel, $Na_V$1.8. *Pain,* 2002. 95(1-2): p. 143-52; Dong, X. W., et al., Small interfering RNA-mediated selective knockdown of $Na_V$1.8 tetrodotoxin-resistant sodium channel reverses mechanical allodynia in neuropathic rats. *Neuroscience,* 2007. 146(2): p. 812-21; Huang, H. L., et al., Proteomic profiling of neuromas reveals alterations in protein composition and local protein synthesis in hyper-excitable nerves. *Mol. Pain,* 2008. 4: p. 33; Black, J. A., et al., Multiple sodium channel isoforms and mitogen-activated protein kinases are present in painful human neuromas. *Ann. Neurol.,* 2008. 64(6): p. 644-53; Coward, K., et al., Immunolocalization of SNS/PN3 and NaN/SNS2 sodium channels in human pain states. *Pain,* 2000. 85(1-2): p. 41-50; Yiangou, Y., et al., SNS/PN3 and SNS2/NaN sodium channel-like immunoreactivity in human adult and neonate injured sensory nerves. *FEBS Lett.,* 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.* 286(46): p. 39836-47). The small DRG neurons where $Na_V1.8$ is expressed include the nociceptors involved in pain signaling. $Na_V1.8$ mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.,* 2002. 22(23): p. 10277-90). $Na_V1.8$ is necessary for rapid repetitive action potentials in nociceptors, and for spontaneous activity of damaged neurons (Choi, J. S. and S. G. Waxman, Physiological interactions between $Na_V1.7$ and $Na_V1.8$ sodium channels: a computer simulation study. *J. Neurophysiol.* 106(6): p. 3173-84; Renganathan, M., T. R. Cummins, and S. G. Waxman, Contribution of $Na_{(V)}1.8$ sodium channels to action potential electrogenesis in DRG neurons. *J. Neurophysiol.,* 2001. 86(2): p. 629-40; Roza, C., et al., The tetrodotoxin-resistant $Na^+$ channel $Na_V1.8$ is essential for the expression of spontaneous activity in damaged sensory axons of mice. *J. Physiol.,* 2003. 550(Pt 3): p. 921-6). In depolarized or damaged DRG neurons, $Na_V1.8$ appears to be a driver of hyper-excitablility (Rush, A. M., et al., A single sodium channel mutation produces hyper- or hypoexcitability in different types of neurons. *Proc. Natl. Acad. Sci. USA,* 2006. 103(21): p. 8245-50). In some animal pain models, $Na_V1.8$ mRNA expression levels have been shown to increase in the DRG (Sun, W., et al., Reduced conduction failure of the main axon of polymodal nociceptive C-fibers contributes to painful diabetic neuropathy in rats. *Brain,* 135(Pt 2): p. 359-75; Strickland, I. T., et al., Changes in the expression of $Na_V1.7$, $Na_V1.8$ and $Na_V1.9$ in a distinct population of dorsal root ganglia innervating the rat knee joint in a model of chronic inflammatory joint pain. *Eur. J. Pain,* 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.,* 512(2): p. 61-6).

The inventors have discovered that some voltage-gated sodium channel inhibitors have limitations as therapeutic agents due to, for example, a poor therapeutic window (e.g., due to a lack of $Na_V$ isoform selectivity, low potency, and/or other reasons). Accordingly, there remains a need to develop selective voltage-gated sodium channel inhibitors, such as selective $Na_V1.8$ inhibitors.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

Figure 1:
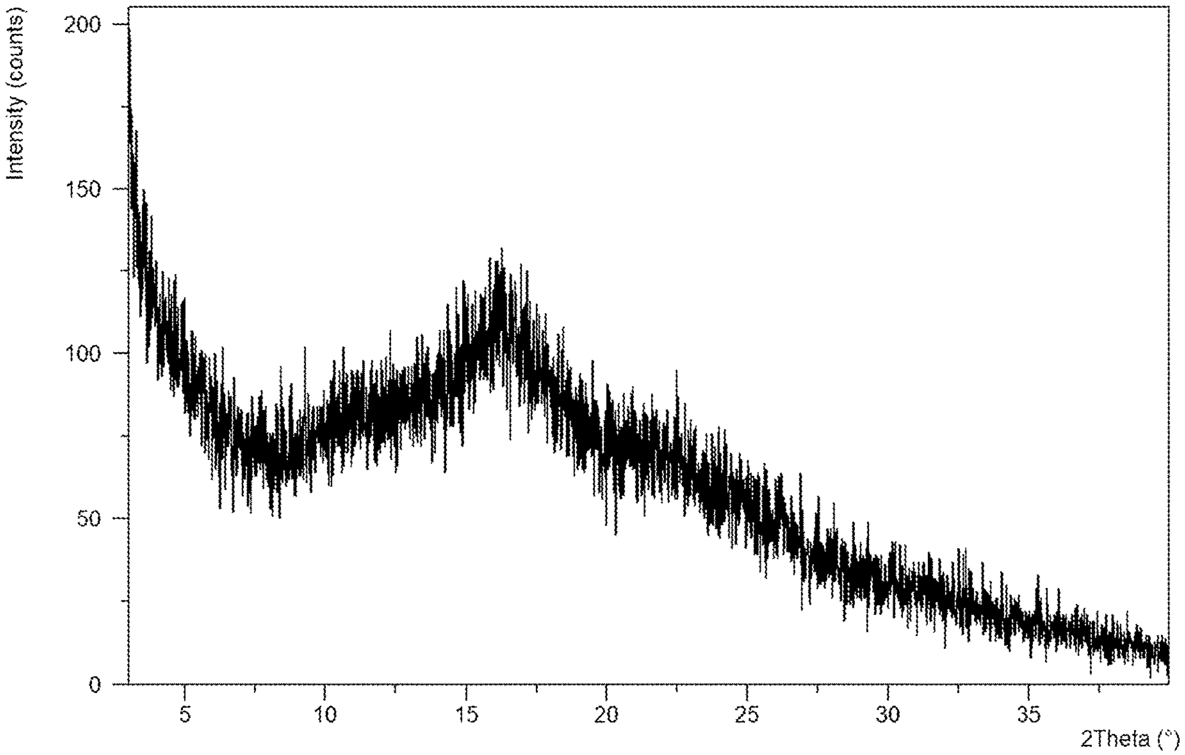
FIG. 1 depicts an XRPD pattern characteristic of amorphous Compound 4.

In one aspect, the invention relates to a compound of formula (I):

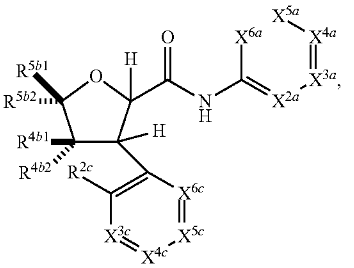

I or a pharmaceutically acceptable salt thereof, wherein:

$X^{2a}$ is N, $N^+$—$O^-$, or C—$R^{2a}$;

$X^{3a}$ is N, $N^+$—$O^-$, C—$R^{3a}$, C—$CONR_2$, or C—$CH_{1-n}(R^A)(OH)(CH_2OH)_n$;

$X^{4a}$ is N, $N^+$—$O^-$, C—$R^{4a}$, C—$CONR_2$, or C—$CH_{1-n}(R^A)(OH)(CH_2OH)_n$;

$X^{5a}$ is N, $N^+$—$O^-$, or C—$R^{5a}$;

$X^{6a}$ is N, $N^+$—$O^-$, or C—$R^{6a}$;

each R is independently H or $C_1$-$C_6$ alkyl;

n is 0 or 1;

$R^A$ is H or $CH_3$;

$R^{2a}$, $R^{3a}$, $R^{4a}$, $R^{5a}$, and $R^{6a}$ are each independently H, halo, $C_1$-$C_6$ alkyl, or $C_1$-$C_6$ haloalkyl;

one of $R^{4b1}$ and $R^{4b2}$ is OH, $C_1$-$C_6$ alkoxy, or $C_1$-$C_6$ haloalkoxy, and the other is H;

$R^{5b1}$ and $R^{5b2}$ are each independently H, $C_1$-$C_6$ alkyl, $C_3$-$C_6$ cycloalkyl, or $C_1$-$C_6$ haloalkyl;

$X^{3c}$ is N or C—$R^{3c}$;

$X^{4c}$ is N or C—$R^{4c}$;

$X^{5c}$ is N or C—$R^{5c}$;

$X^{6c}$ is N or C—$R^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;

$L^1$ is a bond or O;

$L^2$ is a bond or $C_1$-$C_6$ alkylene;

$R^{3c}$ is H, halo, $C_1$-$C_6$ alkyl, or $C_1$-$C_6$ haloalkyl;

$R^{4c}$ is H, halo, $C_1$-$C_6$ alkyl, or $C_1$-$C_6$ haloalkyl;

$R^{5c}$ is H, halo, $C_1$-$C_6$ alkyl, or $C_1$-$C_6$ haloalkyl; and $R^{6c}$ is H, halo, $C_1$-$C_6$ alkyl, or $C_1$-$C_6$ haloalkyl;

provided that no more than two of $X^{2a}$, $X^{3a}$, $X^{4a}$, $X^{5a}$, and $X^{6a}$ are N or $N^+$—$O^-$;

provided that at least one of $X^{3a}$ and $X^{4a}$ is N, $N^+$—$O^-$, C—$R^{3a}$, or C—$R^{4a}$; and provided that no more than one of $X^{3c}$, $X^{4c}$, $X^{5c}$, and $X^{6c}$ is N.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry," Thomas Sorrell, University Science Books, Sausalito: 1999, and "March's Advanced Organic Chemistry," $5^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formula (I), and all of the embodiments thereof (e.g., formulas (I-A), etc.), as described herein, and to the compounds identified in Table A.

As described herein, the compounds of the invention comprise multiple variable groups (e.g., $X^{3a}$, $R^4$, $R^{5b1}$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and optionally their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The chemical structures depicted herein are intended to be understood as they would be understood by one of ordinary skill in the art. For example, with respect to formulas (I), (I-A), (I-A-1), (I-B), and (I-B-1), $X^{2a}$ and $X^{3a}$ are connected by a single bond, $X^{5a}$ and $X^{6a}$ are connected by a double bond, and $X^{4c}$ and $X^{5c}$ are connected by a single bond, even though the bonds between these groups may be obscured by the atom labels in the chemical structures. Using a different style, the structure of Formula I can be drawn as follows to show the bonds:

I

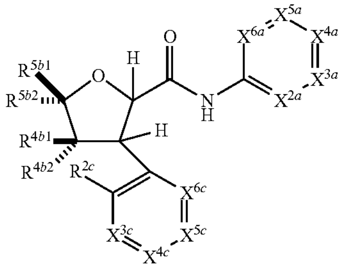

Moreover, a substituent depicted as "$CF_3$" or "$F_3C$" in a chemical structure refers to a trifluoromethyl substituent, regardless of which depiction appears in the chemical structure.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "alkenyl" refers to a straight or branched hydrocarbon chain radical group consisting solely of carbon and hydrogen atoms, containing one or more carbon-carbon double bonds, and having the specified number of carbon atoms, which is attached to the rest of the molecule by a single bond. For example, a "$C_2$-$C_6$ alkenyl" group is an alkenyl group having between two and six carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. For example, a "$C_3$-$C_8$ cycloalkyl" group is a cycloalkyl group having between three and eight carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —$OR_a$ where $R_a$ is an alkyl group having the specified number of carbon atoms. For example, a "$C_1$-$C_6$ alkoxy" group is a radical of the formula —$OR_a$ where $R_a$ is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "alkylene" refers to a divalent, straight or branched hydrocarbon chain radical group consisting solely of carbon and hydrogen atoms, containing no unsaturation, and having the specified number of carbon atoms, which is attached to the rest of the molecule by two single bonds. For example, a "$C_1$-$C_6$ alkylene" group is an alkylene group having between one and six carbon atoms.

As used herein, the term "optionally substituted" refers to a group that is either unsubstituted or substituted with the subsequently identified substituents. For example, a group that is "optionally substituted with 1-2 halo" is either unsubstituted, substituted with 1 halo group, or substituted with 2 halo groups.

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers of the compounds identified by the chemical names and chemical structures provided herein. In addition, single stereoisomers, double bond isomers, conformational isomers, and tautomers as well as mixtures of stereoisomers, double bond isomers, conformational isomers, and tautomers are within the scope of the invention.

As used herein, in any chemical structure or formula, a non-bold, straight bond attached to a stereocenter of a compound, such as in

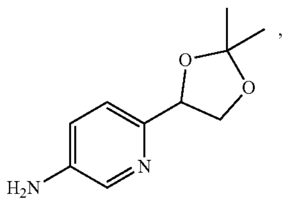

denotes that the configuration of the stereocenter is unspecified. The compound may have any configuration, or a mixture of configurations, at the stereocenter.

As used herein, in any chemical structure or formula, a bold or hashed straight bond attached to a stereocenter of a compound, such as in

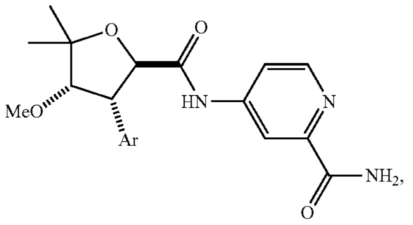

denotes the relative stereochemistry of the stereocenter, relative to other stereocenter(s) to which bold or hashed straight bonds are attached.

As used herein, in any chemical structure or formula, a bold or hashed wedge bond attached to a stereocenter of a compound, such as in

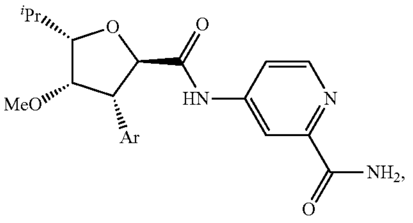

denotes the absolute stereochemistry of the stereocenter, as well as the relative stereochemistry of the stereocenter, relative to other stereocenter(s) to which bold or hashed wedge bonds are attached.

As used herein, the prefix "rac-," when used in connection with a chiral compound, refers to a racemic mixture of the compound. In a compound bearing the "rac-" prefix, the (R)- and (S)-designators in the chemical name reflect the relative stereochemistry of the compound.

As used herein, the prefix "rel-," when used in connection with a chiral compound, refers to a single enantiomer of unknown absolute configuration. In a compound bearing the "rel-" prefix, the (R)- and (S)-designators in the chemical name reflect the relative stereochemistry of the compound, but do not necessarily reflect the absolute stereochemistry of the compound. Where the relative stereochemistry of a given stereocenter is unknown, no stereochemical designator is provided. In some instances, the absolute configuration of some stereocenters is known, while only the relative configuration of the other stereocenters is known. In these instances, the stereochemical designators associated with the stereocenters of known absolute configuration are marked with an asterisk (*), e.g., (R*)— and (S*)—, while the stereochemical designators associated with stereocenters of unknown absolute configuration are not so marked. The unmarked stereochemical designators associated with the stereocenters of unknown absolute configuration reflect the relative stereochemistry of those stereocenters with respect to other stereocenters of unknown absolute configuration, but do not necessarily reflect the relative stereochemistry with respect to the stereocenters of known absolute configuration.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, colloid, or pharmaceutical composition, or dosage form) with one or more other substances, or in the form of a hydrate, solvate, or co-crystal.

As used herein, the term "amorphous" refers to a solid material having no long-range order in the position of its molecules. Amorphous solids are generally glasses or supercooled liquids in which the molecules are arranged in a random manner so that there is no well-defined arrangement, e.g., molecular packing, and no long-range order. Amorphous solids are generally rather isotropic, i.e., exhibit similar properties in all directions and do not have definite melting points. Instead, they typically exhibit a glass transition temperature which marks a transition from glassy amorphous state to supercooled liquid amorphous state upon heating. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e., the material is not crystalline, but is amorphous, as determined by XRPD). Instead, one or several broad peaks (e.g., halos) may appear in the XRPD pattern of the material. See US 2004/0006237 for a representative comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, solid state NMR may also be used to characterize crystalline or amorphous forms.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^{1}H$ and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "$^{1}H$" refers to protium. Where an atom in a compound of the invention, or a pharmaceutically acceptable salt thereof, is designated as protium, protium is present at the specified position at at least the natural abundance concentration of protium.

As used herein, "D," "d," and "$^{2}H$" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labeled" compounds and salts). Examples of stable isotopes which are commercially available and suitable for the invention include without limitation isotopes of hydrogen, carbon, nitrogen, oxygen, and phosphorus, for example $^{2}H$, $^{3}C$, $^{15}N$, $^{18}O$, $^{17}O$, and $^{31}P$, respectively.

The isotope-labeled compounds and salts can be used in a number of beneficial ways, including as medicaments. In some embodiments, the isotope-labeled compounds and salts are deuterium ($^{2}H$)-labeled. Deuterium ($^{2}H$)-labeled compounds and salts are therapeutically useful with potential therapeutic advantages over the non-$^{2}H$-labeled compounds. In general, deuterium ($^{2}H$)-labeled compounds and salts can have higher metabolic stability as compared to those that are not isotope-labeled owing to the kinetic isotope effect described below. Higher metabolic stability translates directly into an increased in vivo half-life or lower dosages, which under most circumstances would represent a preferred embodiment of the present invention. The isotope-labeled compounds and salts can usually be prepared by carrying out the procedures disclosed in the synthesis schemes, the examples and the related description, replacing a non-isotope-labeled reactant by a readily available isotope-labeled reactant.

The deuterium ($^{2}H$)-labeled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For example, if deuterium is bonded to a carbon atom at a non-exchangeable position, rate differences of $k_H/k_D=2\text{-}7$ are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labeled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (~45% deuterium incorporation). In some embodiments, the isotopic enrichment factor is at least 3500 (~52.5% deuterium incorporation), at least 4000 (~60% deuterium incorporation), at least 4500 (~67.5% deuterium incorporation), at least 5000 (~75% deuterium incorporation), at least 5500 (~82.5% deuterium incorporation), at least 6000 (~90% deuterium incorporation), at least 6333.3 (~95% deuterium incorporation), at least 6466.7 (~97% deuterium incorporation), at least 6600 (~99% deuterium incorporation), or at least 6633.3 (~99.5% deuterium incorporation).

In some embodiments, the invention relates to a compound of formula (I-A)

I-A

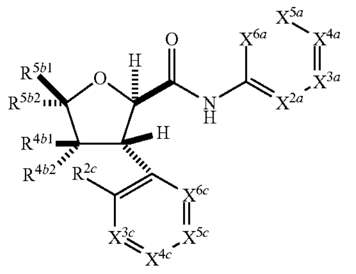

or a pharmaceutically acceptable salt thereof, wherein $X^{2a}$, $X^{3a}$, $X^{4a}$, $X^{5a}$, $X^{6a}$, $R^{4b}$, $R^{4b2}$, $R^{5b1}$, $R^{5b2}$, $X^{3c}$, $X^{4c}$, $X^{5c}$, $X^{6c}$, and $R^{2c}$ are defined as set forth above in connection with formula (I).

In some embodiments, the invention relates to a compound of formula (I-A-1)

I-A-1

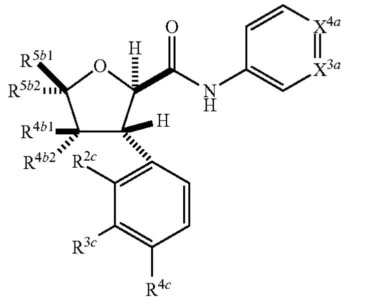

or a pharmaceutically acceptable salt thereof, wherein $X^{3a}$, $X^{4a}$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-B)

I-B

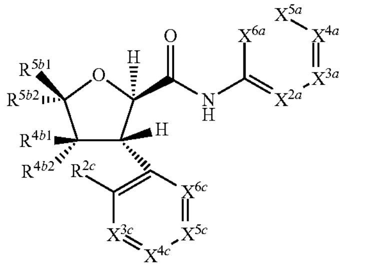

or a pharmaceutically acceptable salt thereof, wherein $X^{2a}$, $X^{3a}$, $X^{4a}$, $X^{5a}$, $X^{6a}$, $R^{4b1}$, $R^{4b2}$, $R^{5b1}$, $R^{5b2}$, $X^{3c}$, $X^{4c}$, $X^{5c}$, $X^{6c}$, and $R^{2c}$ are defined as set forth above in connection with formula (I).

In some embodiments, the invention relates to a compound of formula (I-B-1)

I-B-1

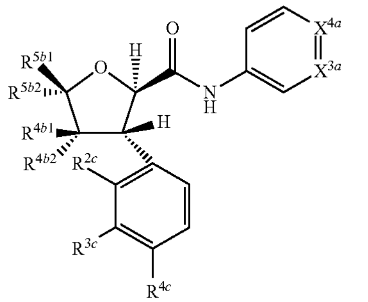

or a pharmaceutically acceptable salt thereof, wherein $X^{3a}$, $X^{4a}$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of any one of formulas (I), (I-A), and (I-B), or a pharmaceutically acceptable salt thereof, wherein $X^{2a}$ is C—$R^{2a}$; and $R^{2a}$ is H.

In some embodiments, the invention relates to a compound of any one of formulas (I), (I-A), (I-A-1), (I-B), and (I-B-1), or a pharmaceutically acceptable salt thereof, wherein $X^{3a}$ is N, C—$CONR_2$, or C—$CH_{1-n}(R^A)(OH)(CH_2OH)_n$. In some embodiments, $X^{3a}$ is N. In other embodiments, $X^{3a}$ is C—$CH_{1-n}(R^A)(OH)(CH_2OH)_n$, and n is 0. In other embodiments, $X^{3a}$ is C—$CH_{1-n}(R^A)(OH)(CH_2OH)_n$, and n is 1.

In some embodiments, the invention relates to a compound of any one of formulas (I), (I-A), (I-A-1), (I-B), and (I-B-1), or a pharmaceutically acceptable salt thereof, wherein $X^{4a}$ is N, C—$CONR_2$, or C—$CH_{1-n}(R^A)(OH)(CH_2OH)_n$. In some embodiments, $X^{4a}$ is N. In other embodiments, $X^{4a}$ is C—$CH_{1-n}(R^A)(OH)(CH_2OH)_n$, and n is 0. In other embodiments, $X^{4a}$ is C—$CH_{1-n}(R^A)(OH)(CH_2OH)_n$, and n is 1.

In some embodiments, the invention relates to a compound of any one of formulas (I), (I-A), (I-A-1), (I-B), and (I-B-1), or a pharmaceutically acceptable salt thereof, wherein one of $X^{3a}$ and $X^{4a}$ is N and the other is C—$CONR_2$, or C—$CH_{1-n}(R^A)(OH)(CH_2OH)_n$.

In some embodiments, the invention relates to a compound of any one of formulas (I), (I-A), (I-A-1), (I-B), and (I-B-1), or a pharmaceutically acceptable salt thereof, wherein $X^{3a}$ is C—$CH_{1-n}(R^A)(OH)(CH_2OH)_n$. In one such embodiment the compound is

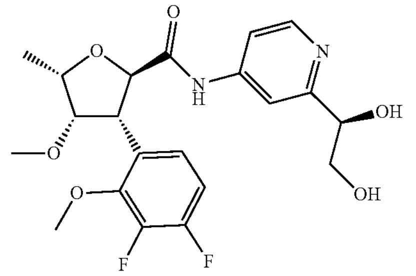 [SMILES: COc1c([C@@H]2[C@H](OC)[C@H](C)O[C@H]2C(=O)Nc2ccnc([C@@H](O)CO)c2)ccc(F)c1F]

In this compound, $R^A$ is H and n is 1.

In some embodiments, the invention relates to a compound of any one of formulas (I), (I-A), (I-A-1), (I-B), and (I-B-1), or a pharmaceutically acceptable salt thereof, wherein $R^{5b2}$ is $C_1$-$C_6$ alkyl or $C_1$-$C_6$ haloalkyl. In some embodiments, $R^{5b2}$ is $CH_3$, $CH(CH_3)_2$, or $CF_3$. In some embodiments, $R^{5b2}$ is $CH(CH_3)_2$. In some embodiments, $R^{5b2}$ is $CF_3$.

In some embodiments, the invention relates to a compound of any one of formulas (I), (I-A), (I-A-1), (I-B), and (I-B-1), or a pharmaceutically acceptable salt thereof, wherein $R^{5b1}$ is H, $C_1$-$C_6$ alkyl or $C_1$-$C_6$ haloalkyl. In some embodiments, $R^{5b1}$ is H, $CH_3$ or $CF_3$. In some embodiments, $R^{5b1}$ is H. In some embodiments, $R^{5b1}$ is $CH_3$.

In some embodiments, the invention relates to a compound of any one of formulas (I), (I-A), (I-A-1), (I-B), and (I-B-1), or a pharmaceutically acceptable salt thereof, wherein $R^{4b1}$ is H or $C_1$-$C_6$ alkoxy. In some embodiments, $R^{4b1}$ is H or $OCH_3$. In some embodiments, $R^{4b1}$ is H. In some embodiments, $R^{4b1}$ is $OCH_3$.

In some embodiments, the invention relates to a compound of any one of formulas (I), (I-A), (I-A-1), (I-B), and (I-B-1), or a pharmaceutically acceptable salt thereof, wherein $R^{4b2}$ is OH, $C_1$-$C_6$ alkoxy, or $C_1$-$C_6$ haloalkoxy. In some embodiments, $R^{4b2}$ is OH. In some embodiments, $R^{4b2}$ is $C_1$-$C_6$ alkoxy. In some embodiments, $R^{4b2}$ is $OCH_3$, $OCH_2CH_3$, or $OCH(CH_3)_2$. In some embodiments, $R^{4b2}$ is $OCH_3$. In some embodiments, $R^{4b2}$ is $OCH_2CH_3$. In some embodiments, $R^{4b2}$ is $OCH(CH_3)_2$.

In some embodiments, the invention relates to a compound of any one of formulas (I), (I-A), (I-A-1), (I-B), and (I-B-1), or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy. In some embodiments, $R^{2c}$ is OH, Cl, $CH_3$, $OCH_3$, $OCD_3$, $OCH_2CH_3$, $OCH(CH_3)_2$, $OCH_2CH_2F$, or $OCH_2CHF_2$. In some embodiments, $R^{2c}$ is $CH_3$ or $OCH_3$. In some embodiments, $R^{2c}$ is $CH_3$. In some embodiments, $R^{2c}$ is $OCH_3$.

In some embodiments, the invention relates to a compound of any one of formulas (I), (I-A), and (I-B), or a pharmaceutically acceptable salt thereof, wherein $X^{3c}$ is C—$R^{3c}$, and $R^{3c}$ is halo or $C_1$-$C_6$ alkyl. In some embodiments, $R^{3c}$ is F. In other embodiments, $R^{3c}$ is $CH_3$.

In some embodiments, the invention relates to a compound of any one of formulas (I-A-1) and (I-B-1), or a pharmaceutically acceptable salt thereof, wherein $R^{3c}$ is halo or $C_1$-$C_6$ alkyl. In some embodiments, $R^{3c}$ is F. In other embodiments, $R^{3c}$ is $CH_3$.

In some embodiments, the invention relates to a compound of any one of formulas (I), (I-A), and (I-B), or a pharmaceutically acceptable salt thereof, wherein $X^{4c}$ is C—$R^{4c}$, and $R^{4c}$ is halo. In some embodiments, $R^{4c}$ is F.

In some embodiments, the invention relates to a compound of any one of formulas (I-A-1) and (I-B-1), or a pharmaceutically acceptable salt thereof, wherein $R^{4c}$ is halo. In some embodiments, $R^{4c}$ is F.

In some embodiments, the invention relates to a compound of any one of formulas (I), (I-A), and (I-B), or a pharmaceutically acceptable salt thereof, wherein $R^{5c}$ is H.

In some embodiments, the invention relates to a compound of any one of formulas (I), (I-A), and (I-B), or a pharmaceutically acceptable salt thereof, wherein $R^{6c}$ is H.

In some embodiments, the invention relates to a compound of any one of formulas (I), (I-A), (I-A-1), (I-B), and (I-B-1), or a pharmaceutically acceptable salt thereof, wherein $R^{4b2}$ is $C_1$-$C_6$ alkoxy. In some embodiments, $R^{4b2}$ is $OCH_2CH_3$ or $OCH_3$. In some embodiments, $R^{4b2}$ is $OCH_3$.

In some embodiments, the invention relates to a compound of any one of formulas (I), (I-A), (I-A-1), (I-B), and (I-B-1), or a pharmaceutically acceptable salt thereof, wherein $R^{4b1}$ is $C_1$-$C_6$ alkoxy. In some embodiments, $R^{4b1}$ is $OCH_2CH_3$ or $OCH_3$. In some embodiments, $R^{4b1}$ is $OCH_3$.

In some embodiments, the invention relates to a compound of any one of formulas (I), (I-A), (I-A-1), (I-B), and (I-B-1), or any embodiment thereof, i.e., the compound in non-salt form.

In some embodiments, the invention relates to a compound selected from Table A, or a pharmaceutically acceptable salt thereof. In other embodiments, the invention relates to a compound selected from Table A, i.e., the compound in non-salt form.

TABLE A

| Compound Structures and Names. |
| --- |
| 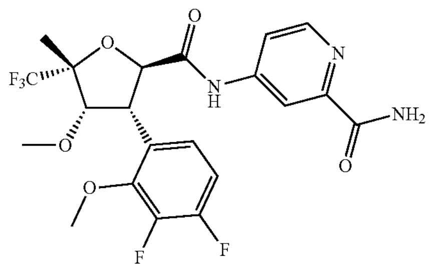 [SMILES: COc1c([C@H]2[C@H](C(=O)Nc3ccnc(C(N)=O)c3)O[C@@](C)(C(F)(F)F)[C@H]2OC)ccc(F)c1F]<br>4-((2R,3R,4S,5R)-3-(3,4-difluoro-2-methoxyphenyl)-4-methoxy-5-methyl-5-(trifluoromethyl)tetrahydrofuran-2-carboxamido)picolinamide |
| 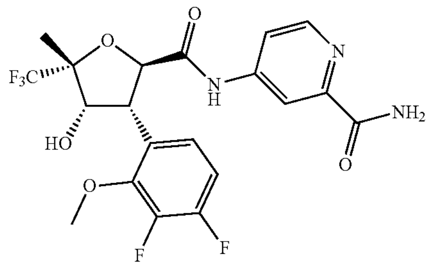 [SMILES: COc1c([C@H]2[C@H](C(=O)Nc3ccnc(C(N)=O)c3)O[C@@](C)(C(F)(F)F)[C@H]2O)ccc(F)c1F]<br>4-((2R,3R,4S,5R)-3-(3,4-difluoro-2-methoxyphenyl)-4-hydroxy-5-methyl-5-(trifluoromethyl)tetrahydrofuran-2-carboxamido)picolinamide |
| 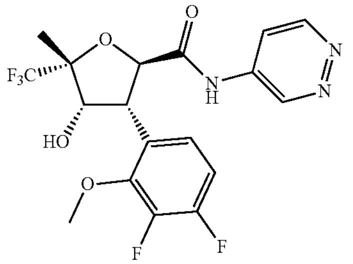 [SMILES: COc1c([C@H]2[C@H](C(=O)Nc3ccnnc3)O[C@@](C)(C(F)(F)F)[C@H]2O)ccc(F)c1F]<br>(2R,3R,4S,5R)-3-(3,4-difluoro-2-methoxyphenyl)-4-hydroxy-5-methyl-N-(pyridazin-4-yl)-5-(trifluoromethyl)tetrahydrofuran-2-carboxamide |
| 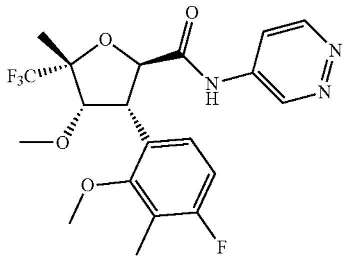 [SMILES: COc1c([C@H]2[C@H](C(=O)Nc3ccnnc3)O[C@@](C)(C(F)(F)F)[C@H]2OC)ccc(F)c1C]<br>(2R,3R,4S,5R)-3-(4-fluoro-2-methoxy-3-methylphenyl)-4-methoxy-5-methyl-N-(pyridazin-4-yl)-5-(trifluoromethyl)tetrahydrofuran-2-carboxamide |

TABLE A-continued

| Compound Structures and Names. |
| --- |
| 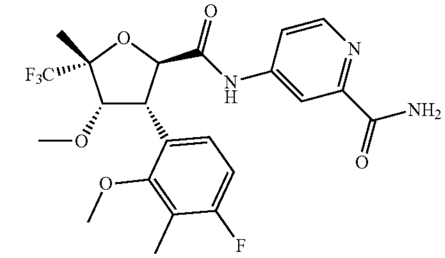 [SMILES: COc1c([C@H]2[C@H](C(=O)Nc3ccnc(C(N)=O)c3)O[C@@](C)(C(F)(F)F)[C@H]2OC)ccc(F)c1C]<br>4-((2R,3R,4S,5R)-3-(4-fluoro-2-methoxy-3-methylphenyl)-4-methoxy-5-methyl-5-(trifluoromethyl)tetrahydrofuran-2-carboxamido)picolinamide |
| 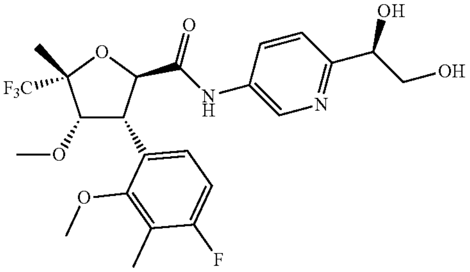 [SMILES: COc1c([C@H]2[C@H](C(=O)Nc3ccc([C@@H](O)CO)nc3)O[C@@](C)(C(F)(F)F)[C@H]2OC)ccc(F)c1C]<br>(2R,3R,4S,5R)-N-(6-((R)-1,2-dihydroxyethyl)pyridin-3-yl)-3-(4-fluoro-2-methoxy-3-methylphenyl)-4-methoxy-5-methyl-5-(trifluoromethyl)tetrahydrofuran-2-carboxamide |
| 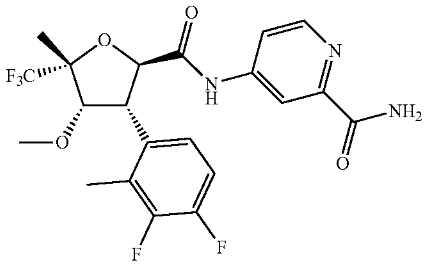 [SMILES: CO[C@H]1[C@@H](c2ccc(F)c(F)c2C)[C@H](C(=O)Nc2ccnc(C(N)=O)c2)O[C@@]1(C)C(F)(F)F]<br>4-((2R,3R,4S,5R)-3-(3,4-difluoro-2-methylphenyl)-4-methoxy-5-methyl-5-(trifluoromethyl)tetrahydrofuran-2-carboxamido)picolinamide |
| 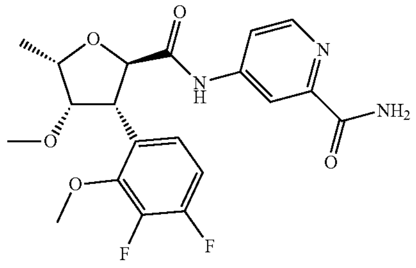 [SMILES: COc1c([C@@H]2[C@H](OC)[C@H](C)O[C@H]2C(=O)Nc2ccnc(C(N)=O)c2)ccc(F)c1F]<br>4-((2R,3R,4S,5S)-3-(3,4-difluoro-2-methoxyphenyl)-4-methoxy-5-methyltetrahydrofuran-2-carboxamido)picolinamide |

TABLE A-continued

| Compound Structures and Names. |
| --- |
| 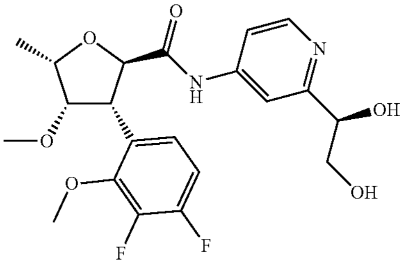 [SMILES: COc1c([C@@H]2[C@H](OC)[C@H](C)O[C@H]2C(=O)Nc2ccnc([C@@H](O)CO)c2)ccc(F)c1F]<br>(2R,3R,4S,5S)-3-(3,4-difluoro-2-methoxyphenyl)-N-(2-((R)-1,2-dihydroxyethyl)pyridin-4-yl)-4-methoxy-5-methyltetrahydrofuran-2-carboxamide |
| 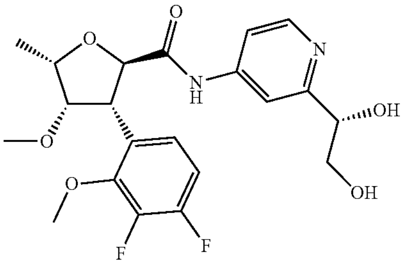 [SMILES: COc1c([C@@H]2[C@H](OC)[C@H](C)O[C@H]2C(=O)Nc2ccnc([C@H](O)CO)c2)ccc(F)c1F]<br>(2R,3R,4S,5S)-3-(3,4-difluoro-2-methoxyphenyl)-N-(2-((S)-1,2-dihydroxyethyl)pyridin-4-yl)-4-methoxy-5-methyltetrahydrofuran-2-carboxamide |
| 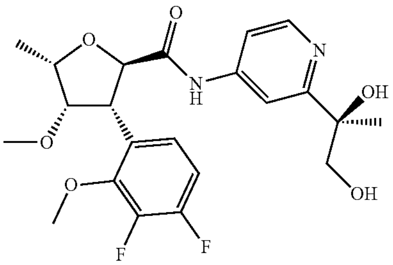 [SMILES: COc1c([C@@H]2[C@H](OC)[C@H](C)O[C@H]2C(=O)Nc2ccnc([C@@](C)(O)CO)c2)ccc(F)c1F]<br>(2R,3R,4S,5S)-3-(3,4-difluoro-2-methoxyphenyl)-N-(2-((R)-1,2-dihydroxypropan-2-yl)pyridin-4-yl)-4-methoxy-5-methyltetrahydrofuran-2-carboxamide |
| 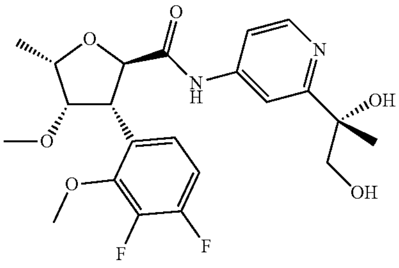 [SMILES: COc1c([C@@H]2[C@H](OC)[C@H](C)O[C@H]2C(=O)Nc2ccnc([C@](C)(O)CO)c2)ccc(F)c1F]<br>(2R,3R,4S,5S)-3-(3,4-difluoro-2-methoxyphenyl)-N-(2-((S)-1,2-dihydroxypropan-2-yl)pyridin-4-yl)-4-methoxy-5-methyltetrahydrofuran-2-carboxamide |

| Compound Structures and Names. |
| --- |
| 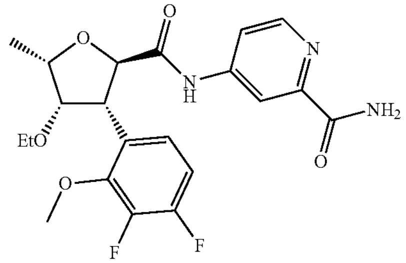 4-((2R,3R,4S,5S)-3-(3,4-difluoro-2-methoxyphenyl)-4-ethoxy-5-methyltetrahydrofuran-2-carboxamido)picolinamide |
| 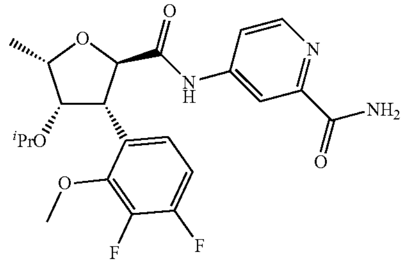 [SMILES: COc1c([C@@H]2[C@H](OC(C)C)[C@H](C)O[C@H]2C(=O)Nc2ccnc(C(N)=O)c2)ccc(F)c1F] 4-((2R,3R,4S,5S)-3-(3,4-difluoro-2-methoxyphenyl)-4-isopropoxy-5-methyltetrahydrofuran-2-carboxamido)picolinamide |
| 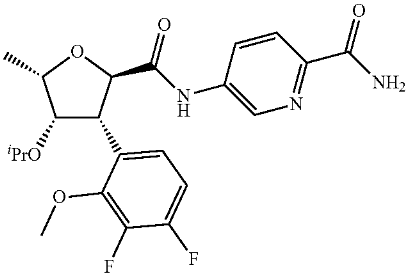 [SMILES: COc1c([C@@H]2[C@H](OC(C)C)[C@H](C)O[C@H]2C(=O)Nc2ccc(C(N)=O)nc2)ccc(F)c1F] 5-((2R,3R,4S,5S)-3-(3,4-difluoro-2-methoxyphenyl)-4-isopropoxy-5-methyltetrahydrofuran-2-carboxamido)picolinamide |
| 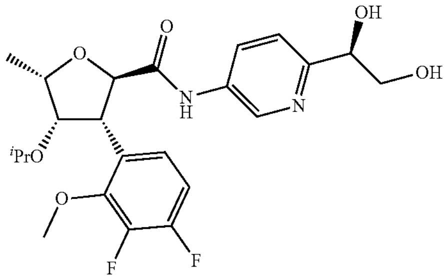 [SMILES: COc1c([C@@H]2[C@H](OC(C)C)[C@H](C)O[C@H]2C(=O)Nc2ccc([C@@H](O)CO)nc2)ccc(F)c1F] (2R,3R,4S,5S)-3-(3,4-difluoro-2-methoxyphenyl)-N-(6-((R)-1,2-dihydroxyethyl)pyridin-3-yl)-4-isopropoxy-5-methyltetrahydrofuran-2-carboxamide |

| Compound Structures and Names. |
| --- |
| 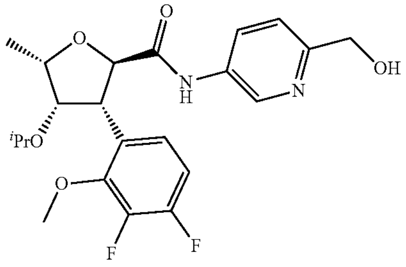 [SMILES: COc1c([C@@H]2[C@H](OC(C)C)[C@H](C)O[C@H]2C(=O)Nc2ccc(CO)nc2)ccc(F)c1F] (2R,3R,4S,5S)-3-(3,4-difluoro-2-methoxyphenyl)-N-(6-(hydroxymethyl)pyridin-3-yl)-4-isopropoxy-5-methyltetrahydrofuran-2-carboxamide |
| 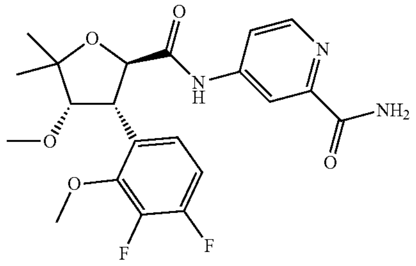 [SMILES: COc1c([C@H]2[C@H](C(=O)Nc3ccnc(C(N)=O)c3)OC(C)(C)[C@H]2OC)ccc(F)c1F] 4-((2R,3R,4S)-3-(3,4-difluoro-2-methoxyphenyl)-4-methoxy-5,5-dimethyltetrahydrofuran-2-carboxamido)picolinamide |
| 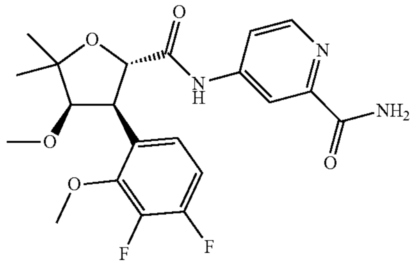 [SMILES: COc1c([C@@H]2[C@@H](C(=O)Nc3ccnc(C(N)=O)c3)OC(C)(C)[C@@H]2OC)ccc(F)c1F] 4-((2S,3S,4R)-3-(3,4-difluoro-2-methoxyphenyl)-4-methoxy-5,5-dimethyltetrahydrofuran-2-carboxamido)picolinamide |
| 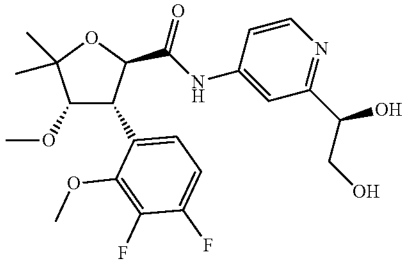 [SMILES: COc1c([C@H]2[C@H](C(=O)Nc3ccnc([C@@H](O)CO)c3)OC(C)(C)[C@H]2OC)ccc(F)c1F] (2R,3R,4S)-3-(3,4-difluoro-2-methoxyphenyl)-N-(2-((R)-1,2-dihydroxyethyl)pyridin-4-yl)-4-methoxy-5,5-dimethyltetrahydrofuran-2-carboxamide |

TABLE A-continued

| Compound Structures and Names. |
|---|
| 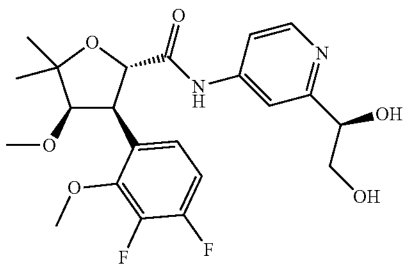 [SMILES: COc1c([C@@H]2[C@@H](C(=O)Nc3ccnc([C@@H](O)CO)c3)OC(C)(C)[C@@H]2OC)ccc(F)c1F] (2S,3S,4R)-3-(3,4-difluoro-2-methoxyphenyl)-N-(2-((R)-1,2-dihydroxyethyl)pyridin-4-yl)-4-methoxy-5,5-dimethyltetrahydrofuran-2-carboxamide |
| 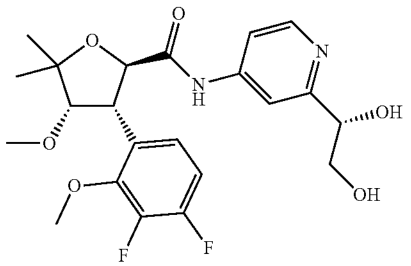 [SMILES: COc1c([C@H]2[C@H](C(=O)Nc3ccnc([C@H](O)CO)c3)OC(C)(C)[C@H]2OC)ccc(F)c1F] (2R,3R,4S)-3-(3,4-difluoro-2-methoxyphenyl)-N-(2-((S)-1,2-dihydroxyethyl)pyridin-4-yl)-4-methoxy-5,5-dimethyltetrahydrofuran-2-carboxamide |
| 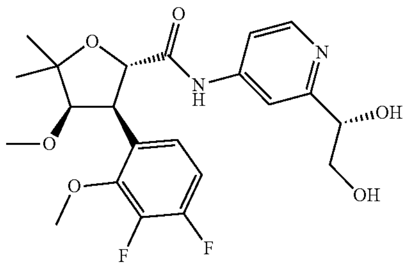 [SMILES: COc1c([C@@H]2[C@@H](C(=O)Nc3ccnc([C@H](O)CO)c3)OC(C)(C)[C@@H]2OC)ccc(F)c1F] (2S,3S,4R)-3-(3,4-difluoro-2-methoxyphenyl)-N-(2-((S)-1,2-dihydroxyethyl)pyridin-4-yl)-4-methoxy-5,5-dimethyltetrahydrofuran-2-carboxamide |
| 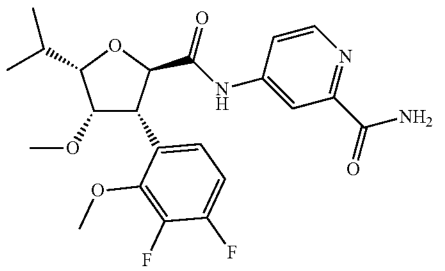 [SMILES: COc1c([C@@H]2[C@H](OC)[C@H](C(C)C)O[C@H]2C(=O)Nc2ccnc(C(N)=O)c2)ccc(F)c1F] 4-((2R,3R,4S,5S)-3-(3,4-difluoro-2-methoxyphenyl)-5-isopropyl-4-methoxytetrahydrofuran-2-carboxamido)picolinamide |

TABLE A-continued

| Compound Structures and Names. |
|---|
| 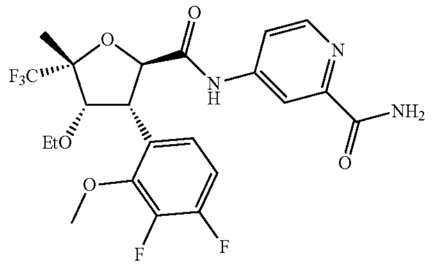 4-((2R,3R,4S,5R)-3-(3,4-difluoro-2-methoxyphenyl)-4-ethoxy-5-methyl-5-(trifluoromethyl)tetrahydrofuran-2-carboxamido)picolinamide |

In some embodiments, the invention relates to a compound of formula

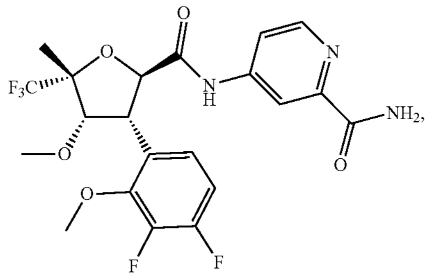 [SMILES: COc1c([C@H]2[C@H](C(=O)Nc3ccnc(C(N)=O)c3)O[C@@](C)(C(F)(F)F)[C@H]2OC)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

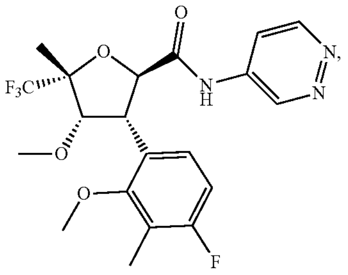 [SMILES: COc1c([C@H]2[C@H](C(=O)Nc3ccnnc3)O[C@@](C)(C(F)(F)F)[C@H]2OC)ccc(F)c1C]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

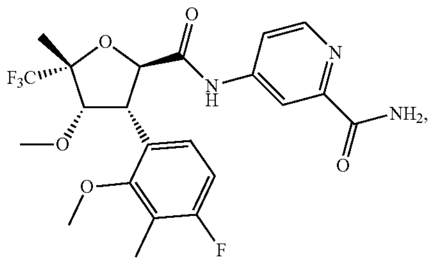 [SMILES: COc1c([C@H]2[C@H](C(=O)Nc3ccnc(C(N)=O)c3)O[C@@](C)(C(F)(F)F)[C@H]2OC)ccc(F)c1C]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

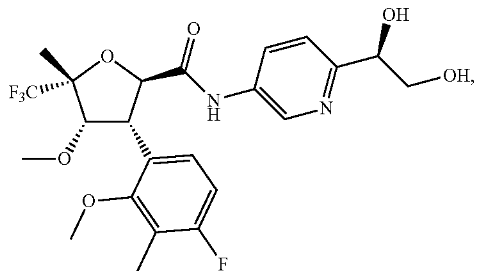 [SMILES: COc1c([C@H]2[C@H](C(=O)Nc3ccc([C@@H](O)CO)nc3)O[C@@](C)(C(F)(F)F)[C@H]2OC)ccc(F)c1C]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

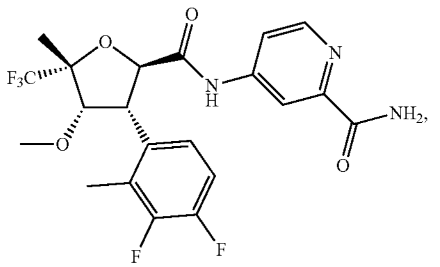 [SMILES: CO[C@H]1[C@@H](c2ccc(F)c(F)c2C)[C@H](C(=O)Nc2ccnc(C(N)=O)c2)O[C@@]1(C)C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

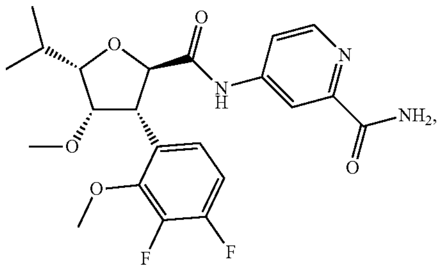 [SMILES: COc1c([C@@H]2[C@H](OC)[C@H](C(C)C)O[C@H]2C(=O)Nc2ccnc(C(N)=O)c2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

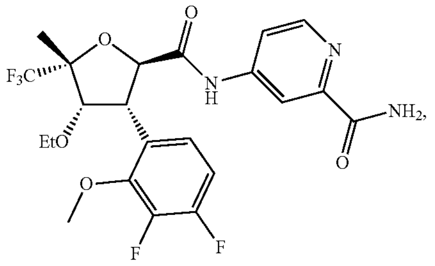 [SMILES: CCO[C@H]1[C@@H](c2ccc(F)c(F)c2OC)[C@H](C(=O)Nc2ccnc(C(N)=O)c2)O[C@@]1(C)C(F)(F)F]

or a pharmaceutically acceptable salt thereof. In other embodiments, the invention relates to the foregoing compound in non-salt form. Such compound is considered to be a "compound of the invention," as that term is used herein.

Salts, Compositions, Uses, Formulation, Administration and Additional Agents

Pharmaceutically Acceptable Salts and Compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences,* 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate, powdered tragacanth, malt, gelatin, talc, excipients such as cocoa butter and suppository waxes, oils such as peanut oil, cottonseed oil, safflower oil, sesame oil, olive oil, corn oil and soybean oil, glycols, such a propylene glycol or polyethylene glycol, esters such as ethyl oleate and ethyl laurate, agar, buffering agents such as magnesium hydroxide and aluminum hydroxide, alginic acid, pyrogen-free water, isotonic saline, Ringer's solution, ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is $Na_V1.8$.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion injury, complex regional pain syndrome, drug therapy induced neuralgia, cancer chemotherapy induced neuralgia, anti-retroviral therapy induced neuralgia, post spinal cord injury pain, small fiber neuropathy, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., joint replacement pain, soft tissue surgery pain, herniorrhaphy pain, bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of herniorrhaphy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method of treating or lessening the severity in a subject of a neurodegenerative disease comprising administering an effective amount of a compound of the invention, a pharmaceutically acceptable salt thereof or a pharmaceutical composition thereof. In some aspects, the neurodegenerative disease comprises multiple sclerosis. In some aspects, the neurodegenerative disease comprises Pitt Hopkins Syndrome (PTHS).

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a method of treating or lessening the severity in a subject of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, post-surgical pain (e.g., joint replacement pain, soft tissue surgery pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers-Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain, non-malignant chronic bone pain, rheumatoid arthritis, osteoarthritis, spinal stenosis, neuropathic low back pain, myofascial pain syndrome, fibromyalgia, temporomandibular joint pain, chronic visceral pain, abdominal pain, pancreatic pain, IBS pain, chronic and acute headache pain, migraine, tension headache, cluster headaches, chronic and acute neuropathic pain, post-herpetic neuralgia, diabetic neuropathy, HIV-associated neuropathy, trigeminal neuralgia, Charcot-Marie-Tooth neuropathy, hereditary sensory neuropathy, peripheral nerve injury, painful neuromas, ectopic proximal and distal discharges, radiculopathy, chemotherapy induced neuropathic pain, radiotherapy-induced neuropathic pain, persistent/chronic post-surgical pain (e.g., post amputation, post-thoracotomy, post-cardiac surgery), post-mastectomy pain, central pain, spinal cord injury pain, post-stroke pain, thalamic pain, phantom pain (e.g., following removal of lower extremity, upper extremity, breast), intractable pain, acute pain, acute post-operative pain, acute musculoskeletal pain, joint pain, mechanical low back pain, neck pain, tendonitis, injury pain, exercise pain, acute visceral pain, pyelonephritis, appendicitis, cholecystitis, intestinal obstruction, hernias, chest pain, cardiac pain, pelvic pain, renal colic pain, acute obstetric pain, labor pain, cesarean section pain, acute inflammatory pain, burn pain, trauma pain, acute intermittent pain, endometriosis, acute herpes zoster pain, sickle cell anemia, acute pancreatitis, breakthrough pain, orofacial pain, sinusitis pain, dental pain, multiple sclerosis (MS) pain, pain in depression, leprosy pain, Behcet's disease pain, adiposis dolorosa, phlebitic pain, Guillain-Barre pain, painful legs and moving toes, Haglund syndrome, erythromelalgia pain, Fabry's disease pain, bladder and urogenital disease, urinary incontinence, pathological cough, hyperactive bladder, painful bladder syndrome, interstitial cystitis (IC), prostatitis, complex regional pain syndrome (CRPS), type I, complex regional pain syndrome (CRPS) type II, widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion injury, complex regional pain syndrome, drug therapy induced neuralgia, cancer chemotherapy induced neuralgia, anti-retroviral therapy induced neuralgia, post spinal cord injury pain, small fiber neuropathy, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute post-operative pain.

In another aspect, the invention features a compound of the invention, or a pharmaceutically acceptable salt or pharmaceutical composition thereof, for use in a method of treating or lessening the severity in a subject of postsurgical pain (e.g., joint replacement pain, soft tissue surgery pain, herniorrhaphy pain, bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of herniorrhaphy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method of treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers-Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain, non-malignant chronic bone pain, rheumatoid arthritis, osteoarthritis, spinal stenosis, neuropathic low back pain, myofascial pain syndrome, fibromyalgia, temporomandibular joint pain, chronic visceral pain, abdominal pain, pancreatic pain, IBS pain, chronic and acute headache pain, migraine, tension headache, cluster headaches, chronic and acute neuropathic pain, post-herpetic neuralgia, diabetic neuropathy, HIV-associated neuropathy, trigeminal neuralgia, Charcot-Marie-Tooth neuropathy, hereditary sensory neuropathy, peripheral nerve injury, painful neuromas, ectopic proximal and distal discharges, radiculopathy, chemotherapy induced neuropathic pain, radiotherapy-induced neuropathic pain, persistent/chronic post-surgical pain (e.g., post amputation, post-thoracotomy, post-cardiac surgery), post-mastectomy pain, central pain, spinal cord injury pain, post-stroke pain, thalamic pain, phantom pain (e.g., following removal of lower extremity, upper extremity, breast), intractable pain, acute pain, acute post-operative pain, acute musculoskeletal pain, joint pain, mechanical low back pain, neck pain, tendonitis, injury pain, exercise pain, acute visceral pain, pyelonephritis, appendicitis, cholecystitis, intestinal obstruction, hernias, chest pain, cardiac pain, pelvic pain, renal colic pain, acute obstetric pain, labor pain, cesarean section pain, acute inflammatory pain, burn pain, trauma pain, acute intermittent pain, endometriosis, acute herpes zoster pain, sickle cell anemia, acute pancreatitis, breakthrough pain, orofacial pain, sinusitis pain, dental pain, multiple sclerosis (MS) pain, pain in depression, leprosy pain, Behcet's disease pain, adiposis dolorosa, phlebitic pain, Guillain-Barre pain, painful legs and moving toes, Haglund syndrome, erythromelalgia pain, Fabry's disease pain, bladder and urogenital disease, urinary incontinence, pathological cough, hyperactive bladder, painful bladder syndrome, interstitial cystitis (IC), prostatitis, complex regional pain syndrome (CRPS), type I, complex regional pain syndrome (CRPS) type II, widespread pain, paroxysmal extreme pain, pruritus, tinnitus, or angina-induced pain.

In another aspect, the invention features a compound of the invention, or a pharmaceutically acceptable salt or pharmaceutical composition thereof, for use in a method of treating or lessening the severity in a subject of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or post-amputation pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy).

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion injury, complex regional pain syndrome, drug therapy induced neuralgia, cancer chemotherapy induced neuralgia, anti-retroviral therapy induced neuralgia, post spinal cord injury pain, small fiber neuropathy, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., joint replacement pain, soft tissue surgery pain, herniorrhaphy pain, bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of herniorrhaphy pain.

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for the manufacture of a medicament for use in treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers- Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporomandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain, non-malignant chronic bone pain, rheumatoid arthritis, osteoarthritis, spinal stenosis, neuropathic low back pain, myofascial pain syndrome, fibromyalgia, temporomandibular joint pain, chronic visceral pain, abdominal pain, pancreatic pain, IBS pain, chronic and acute headache pain, migraine, tension headache, cluster headaches, chronic and acute neuropathic pain, post-herpetic neuralgia, diabetic neuropathy, HIV-associated neuropathy, trigeminal neuralgia, Charcot-Marie-Tooth neuropathy, hereditary sensory neuropathy, peripheral nerve injury, painful neuromas, ectopic proximal and distal discharges, radiculopathy, chemotherapy induced neuropathic pain, radiotherapy-induced neuropathic pain, persistent/chronic post-surgical pain (e.g., post amputation, post-thoracotomy, post-cardiac surgery), post-mastectomy pain, central pain, spinal cord injury pain, post-stroke pain, thalamic pain, phantom pain (e.g., following removal of lower extremity, upper extremity, breast), intractable pain, acute pain, acute post-operative pain, acute musculoskeletal pain, joint pain, mechanical low back pain, neck pain, tendonitis, injury pain, exercise pain, acute visceral pain, pyelonephritis, appendicitis, cholecystitis, intestinal obstruction, hernias, chest pain, cardiac pain, pelvic pain, renal colic pain, acute obstetric pain, labor pain, cesarean section pain, acute inflammatory pain, burn pain, trauma pain, acute intermittent pain, endometriosis, acute herpes zoster pain, sickle cell anemia, acute pancreatitis, breakthrough pain, orofacial pain, sinusitis pain, dental pain, multiple sclerosis (MS) pain, pain in depression, leprosy pain, Behcet's disease pain, adiposis dolorosa, phlebitic pain, Guillain-Barre pain, painful legs and moving toes, Haglund syndrome, erythromelalgia pain, Fabry's disease pain, bladder and urogenital disease, urinary incontinence, pathological cough, hyperactive bladder, painful bladder syndrome, interstitial cystitis (IC), prostatitis, complex regional pain syndrome (CRPS), type I, complex regional pain syndrome (CRPS) type II, widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

In another aspect, the invention provides the use of a compound of the invention, a pharmaceutically acceptable salt thereof, or a pharmaceutical composition thereof for the manufacture of a medicament for use in treating or lessening the severity of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or postamputation pain.

Administration of Compounds, Pharmaceutically Acceptable Salts, and Compositions In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are optionally formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder, the activity of the specific compound or salt employed, the specific composition employed, the age, body weight, general health, sex and diet of the subject, the time of administration, route of administration, and rate of excretion of the specific compound or salt employed, the duration of the treatment, drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 1000 mg/kg, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: non-opioid analgesics (indoles such as Etodolac, Indomethacin, Sulindac, Tolmetin, naphthylalkanones such as Nabumetone, oxicams such as Piroxicam, para-aminophenol derivatives, such as Acetaminophen, propionic acids such as Fenoprofen, Flurbiprofen, Ibuprofen, Ketoprofen, Naproxen, Naproxen sodium, Oxaprozin, salicylates such as Aspirin, Choline magnesium trisalicylate, Diflunisal, fenamates such as meclofenamic acid, Mefenamic acid, and pyrazoles such as Phenylbutazone), or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp &Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, IV meloxicam (e.g., Anjeso®), nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anesthetic such as mexiletine;

(20) a corticosteroid such as dexamethasone;

(21) a 5-HT receptor agonist or antagonist, particularly a 5-$HT_{1B/1D}$ agonist such as eletriptan, sumatriptan, naratriptan, zolmitriptan or rizatriptan;

(22) a 5-$HT_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinyl-methoxy)-2-chloropyridine (ABT-594) or nicotine;

(24) Tramadol®, Tramadol ER (Ultram ER®), IV Tramadol, Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(15)-1-({[5-chloro-2-(3-fluorophenoxy)pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) a $Na_V1.7$ blocker, such as XEN-402, XEN403, TV-45070, PF-05089771, CNV1014802, GDC-0276, RG7893 BIIB-074 (Vixotrigine), BIIB-095, ASP-1807, DSP-3905, OLP-1002, RQ-00432979, FX-301, DWP- 1706, DWP-17061, IMB-110, IMB-111, IMB-112 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, WO2013/109521 (US2015005304), WO2020/117626, and CN111217776, the entire contents of each application hereby incorporated by reference;

(38a) a $Na_V1.7$ blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) a $Na_V1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), WO2015/089361 (US20150166589), WO2019/014352 (US20190016671), WO2018/213426, WO2020/146682, WO2020/146612, WO2020/014243, WO2020/014246, WO2020/092187, WO2020/092667 (US2020140411), WO2020/261114, WO2020/140959, WO2020/151728, WO2021/032074, CN112390745, CN111808019, CN112225695, CN112457294, CN112300051, CN112300069, CN112441969, and CN112479996 (WO2021/047622), the entire contents of each application hereby incorporated by reference;

(39a) a $Na_V1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, 2-(4-fluoro-2-methyl-phenoxy)-N-(2-oxo-1H-pyridin-4-yl)-4-(trifluoromethyl)benzamide, [4-[[2-(4-fluoro-2-methyl-phenoxy)-4-(trifluoromethyl)benzoyl]amino]-2-oxo-1-pyridyl]methyl dihydrogen phosphate, 2-(4-fluoro-2-(methyl-$d_3$)phenoxy)-N-(2-oxo-1,2-dihydropyridin-4-yl)-4-(trifluoromethyl)benzamide, (4-(2-(4-fluoro-2-(methyl-$d_3$)phenoxy)-4-(trifluoromethyl)benzamido)-2-oxopyridin-1(2H)-yl)methyl dihydrogen phosphate, 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido)benzoic acid, 5-(4,5-dichloro-2-(2,4-difluorophenoxy)benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide, N-(3-sulfamoylphenyl)-2-(4-(trifluoromethoxy)phenoxy)-4-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethyl)benzamide, N-(3-carbamoyl-4-fluoro-phenyl)-2-fluoro-6-[2-methoxy-4-(trifluoromethoxy)phenoxy]-3-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethoxy)benzamide, 4-[[2-fluoro-6-[2-methoxy-4-(trifluoromethoxy)phenoxy]-3-(trifluoromethyl)benzoyl]amino]pyridine-2-carboxamide, 4-[[3-chloro-2-fluoro-6-[2-methoxy-4-(trifluoromethoxy)phenoxy]benzoyl]amino]pyridine-2-carboxamide, 4-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-3-(difluoromethyl)-2-fluoro-6-[2-methoxy-4-(trifluoromethoxy)phenoxy]benzamide, 4-[[2-fluoro-6-[2-(trideuteriomethoxy)-4-(trifluoromethoxy)phenoxy]-3-(trifluoromethoxy)benzoyl]amino]pyridine-2-carboxamide, N-(3-carbamoyl-4-fluoro-phenyl)-6-[2-chloro-4-(trifluoromethoxy)phenoxy]-2-fluoro-3-(trifluoromethyl)benzamide, N-(3-carbamoyl-4-fluoro-phenyl)-2-fluoro-6-[2-methyl-4-(trifluoromethoxy)phenoxy]-3-(trifluoromethyl)benzamide, N-(3-carbamoyl-4-fluoro-phenyl)-2,3,4-trifluoro-6-[2-methoxy-4-(trifluoromethoxy)phenoxy]benzamide, N-(2-carbamoyl-4-pyridyl)-3-fluoro-5-[2-methoxy-4-(trifluoromethoxy)phenoxy]-2-(trifluoromethyl)pyridine-4-carboxamide, 4-[[6-[2-(difluoromethoxy)-4-(trifluoromethoxy)phenoxy]-2-fluoro-3-(trifluoromethyl)benzoyl]amino]pyridine-2-carboxamide, N-(3-carbamoyl-4-fluoro-phenyl)-6-[3-chloro-4-(trifluoromethoxy)phenoxy]-2-fluoro-3-(trifluoromethyl)benzamide, N-(3-carbamoyl-4-fluoro-phenyl)-2-fluoro-6-[4-(trifluoromethoxy)phenoxy]-3-

(trifluoromethyl)benzamide, N-(4-carbamoyl-3-fluoro-phenyl)-2-fluoro-6-[2-methoxy-4-(trifluoromethoxy) phenoxy]-3-(trifluoromethyl)benzamide, 4-[[2-fluoro-6-[2-(trideuteriomethoxy)-4-(trifluoromethoxy) phenoxy]-4-(trifluoromethyl)benzoyl]amino]pyridine-2-carboxamide, N-(3-carbamoyl-4-fluoro-phenyl)-2-fluoro-6-[3-fluoro-4-(trifluoromethoxy)phenoxy]-3-(trifluoromethyl)benzamide, N-(3-carbamoyl-4-fluoro-phenyl)-2-[2-methoxy-4-(trifluoromethoxy)phenoxy]-5-(1,1,2,2,2-pentafluoroethyl)benzamide, 4-[[4-(difluoromethoxy)-2-fluoro-6-[2-methoxy-4-(trifluoromethoxy)phenoxy]benzoyl]amino]pyridine-2-carboxamide, N-(3-carbamoyl-4-fluoro-phenyl)-2-fluoro-6-[2-fluoro-4-(trifluoromethoxy)phenoxy]-3-(trifluoromethyl)benzamide, 4-[[4-cyclopropyl-2-fluoro-6-[2-methoxy-4-(trifluoromethoxy)phenoxy] benzoyl]amino]pyridine-2-carboxamide, N-(3-carbamoyl-4-fluoro-phenyl)-5-fluoro-2-[2-methoxy-4-(trifluoromethoxy)phenoxy]-4-(trifluoromethyl) benzamide, 5-[[2-fluoro-6-[2-(trideuteriomethoxy)-4-(trifluoromethoxy)phenoxy]-3-(trifluoromethyl) benzoyl]amino]pyridine-2-carboxamide, N-(3-carbamoyl-4-fluoro-phenyl)-2-fluoro-6-(4-fluorophenoxy)-3-(trifluoromethyl)benzamide, 4-(2-fluoro-6-(2-methoxy-4-(trifluoromethoxy)phenoxy)-3-(trifluoromethyl)benzamido)picolinamide, or 4-[[2-fluoro-6-[3-fluoro-2-methoxy-4-(trifluoromethoxy) phenoxy]-3-(trifluoromethyl)benzoyl]amino]pyridine-2-carboxamide;

(40) a combined $Na_V1.7$ and $Na_V1.8$ blocker, such as DSP-2230, Lohocla201 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®) bupivacaine ER (Posimir), bupivacaine collagen (Xaracoll) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is selected from a GlyT2/5HT2 inhibitor, such as Operanserin (VVZ149), a TRPV modulator such as CA008, CMX-020, NEO6860, FTABS, CNTX4975, MCP101, MDR16523, or MDR652, a EGRI inhibitor such as Brivoglide (AYX1), an NGF inhibitor such as Tanezumab, Fasinumab, ASP6294, MEDI7352, a Mu opioid agonist such as Cebranopadol, NKTR181 (oxycodegol), a CB-1 agonist such as NEO1940 (AZN1940), an imidazoline 12 agonist such as CR4056 or a p75NTR-Fc modulator such as LEVI-04.

In another embodiment, the additional therapeutic agent is oliceridine or ropivacaine (TLC590).

In another embodiment, the additional therapeutic agent is a $Na_V1.7$ blocker such as ST-2427 or ST-2578 and those disclosed in WO2010129864, WO2015157559, WO2017059385, WO2018183781, WO2018183782, WO2020072835, and WO2022036297 the entire contents of each application hereby incorporated by reference. In some embodiments, the additional therapeutic agent is a $Na_V1.7$ blocker disclosed in WO2020072835. In some embodiments, the additional therapeutic agent is a $Na_V1.7$ blocker disclosed in WO2022036297.

In another embodiment, the additional therapeutic agent is ASP18071, CC-8464, ANP-230, ANP-231, NOC-100, NTX-1175, ASN008, NW3509, AM-6120, AM-8145, AM-0422, BL-017881, NTM-006, Opiranserin (Unafra™), brivoligide, SR419, NRD.E1, LX9211, LY3016859, ISC-17536, NFX-88, LAT-8881, AP-235, NYX 2925, CNTX-6016, S-600918, S-637880, RQ-00434739, KLS-2031, MEDI 7352, or XT-150.

In another embodiment, the additional therapeutic agent is Olinvyk, Zynrelef, Seglentis, Neumentum, Nevakar, HTX-034, CPL-01, ACP-044, HRS-4800, Tarlige, BAY2395840, LY3526318, Eliapixant, TRVO45, RTA901, NRD1355-E1, MT-8554, LY3556050, AP-325, tetrodotoxin, Otenaproxesul, CFTX-1554, Funapide, iN1011-N17, JMKX000623, ETX-801, or ACD440.

In another embodiment, the additional therapeutic agent is a compound disclosed in WO2021257490, WO2021257420, WO2021257418, WO2020014246, WO2020092187, WO2020092667, WO2020261114, CN112457294, CN112225695, CN111808019, WO2021032074, WO2020151728, WO2020140959, WO2022037641, WO2022037647, CN112300051, CN112300069, WO2014120808, WO2015089361, WO2019014352, WO2021113627, WO2013086229, WO2013134518, WO2014211173, WO2014201206, WO2016141035, WO2021252818, WO2021252822, and WO2021252820.

In some embodiments, the additional therapeutic agent is a compound disclosed in WO2013086229. In some embodiments, the additional therapeutic agent is a compound disclosed in WO2013134518. In some embodiments, the additional therapeutic agent is a compound disclosed in WO2014211173. In some embodiments, the additional therapeutic agent is a compound disclosed in WO2014201206. In some embodiments, the additional therapeutic agent is a compound disclosed in WO2016141035. In some embodiments, the additional therapeutic agent is a compound disclosed in WO2021252818. In some embodiments, the additional therapeutic agent is a compound disclosed in WO2021252822. In some embodiments, the additional therapeutic agent is a compound disclosed in WO2021252820. In some embodiments, the additional therapeutic agent is a compound disclosed in WO2020072835. In some embodiments, the additional therapeutic agent is a compound disclosed in WO2022036297.

In another embodiment, the additional therapeutic agent is a sodium channel inhibitor (also known as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562, 5,886,026, and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena, and the comparative evaluation of new sodium channel inhibitors.

Synthesis of the Compounds of the Invention

The compounds of the invention can be prepared from known materials by the methods described in the Examples, other similar methods, and other methods known to one skilled in the art. As one skilled in the art would appreciate, the functional groups of the intermediate compounds in the methods described below may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, as described herein, including all embodiments thereof, except that one or more atoms has been replaced with a radioisotope of the atom present in the compounds of the invention.

As used herein, the term "radioisotope" refers to an isotope of an element that is known to undergo spontaneous radioactive decay. Examples of radioisotopes include $^{3}H$, $^{14}C$, $^{2}P$, $^{3}S$, $^{18}F$, $^{36}Cl$, and the like, as well as the isotopes for which a decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium ($^{3}H$)- and/or carbon-14 ($^{14}C$)-labeled compounds may be useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

ENUMERATED EMBODIMENTS

Additional embodiments, features, and advantages of the disclosure will be apparent from the following detailed description and through practice of the disclosure. The compounds and methods of the present disclosure can be described as embodiments in any of the following enumerated clauses. It will be understood that any of the embodiments described herein can be used in connection with any other embodiments described herein to the extent that the embodiments do not contradict one another.

1. A compound of formula (I)

I

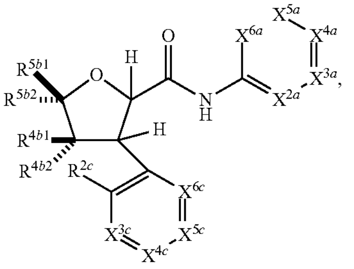

or a pharmaceutically acceptable salt thereof, wherein:

$X^{2a}$ is N, $N^+$—$O^-$, or C—$R^{2a}$;

$X^{3a}$ is N, $N^+$—$O^-$, C—$R^{3a}$, C—$CONR_2$, or C—$CH_{1-n}(R^A)(OH)(CH_2OH)_n$;

$X^{4a}$ is N, $N^+$—$O^-$, C—$R^{4a}$, C—$CONR_2$, or C—$CH_{1-n}(R^A)(OH)(CH_2OH)_n$;

$X^{5a}$ is N, $N^+$—$O^-$, or C—$R^{5a}$;

$X^{6a}$ is N, $N^+$—$O^-$, or C—$R^{6a}$;

each R is independently H or $C_1$-$C_6$ alkyl;

n is 0 or 1;

$R^A$ is H or $CH_3$;

$R^{2a}$, $R^{3a}$, $R^{4a}$, $R^{5a}$, and $R^{6a}$ are each independently H, halo, $C_1$-$C_6$ alkyl, or $C_1$-$C_6$ haloalkyl; one of $R^{4b1}$ and $R^{4b2}$ is OH, $C_1$-$C_6$ alkoxy, or $C_1$-$C_6$ haloalkoxy, and the other is H;

$R^{5b1}$ and $R^{5b2}$ are each independently H, $C_1$-$C_6$ alkyl, $C_3$-$C_6$ cycloalkyl, or $C_1$-$C_6$ haloalkyl;

$X^{3c}$ is N or C—$R^{3c}$;

$X^{4c}$ is N or C—$R^{4c}$;

$X^{5c}$ is N or C—$R^{5c}$;

$X^{6c}$ is N or C—$R^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;

$L^1$ is a bond or O;

$L^2$ is a bond or $C_1$-$C_6$ alkylene;

$R^{3c}$ is H, halo, $C_1$-$C_6$ alkyl, or $C_1$-$C_6$ haloalkyl;

$R^{4c}$ is H, halo, $C_1$-$C_6$ alkyl, or $C_1$-$C_6$ haloalkyl;

$R^{5c}$ is H, halo, $C_1$-$C_6$ alkyl, or $C_1$-$C_6$ haloalkyl; and $R^{6c}$ is H, halo, $C_1$-$C_6$ alkyl, or $C_1$-$C_6$ haloalkyl;

provided that no more than two of $X^{2a}$, $X^{3a}$, $X^{4a}$, $X^{5a}$, and $X^{6a}$ are N or $N^+$—$O^-$;

provided that at least one of $X^{3a}$ and $X^{4a}$ is N, $N^+$—$O^-$, C—$R^{3a}$, or C—$R^{4a}$; and provided that no more than one of $X^3$, $X^{4c}$, $X^{5c}$, and $X^{6c}$ is N.

2. The compound of clause 1, wherein the compound has formula (I-A)

I-A

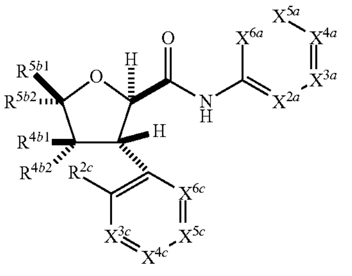

or a pharmaceutically acceptable salt thereof.

3. The compound of clause 1, wherein the compound has formula (I-A-1)

I-A-1

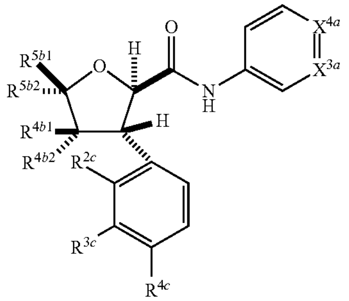

or a pharmaceutically acceptable salt thereof.

4. The compound of clause 1, wherein the compound has formula (I-B)

I-B

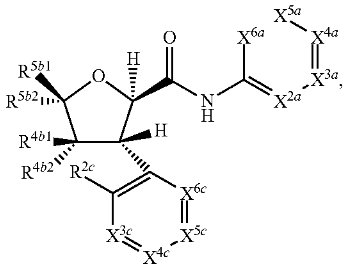

or a pharmaceutically acceptable salt thereof.

5. The compound of clause 1, wherein the compound has formula (I-B-1)

I-B-1

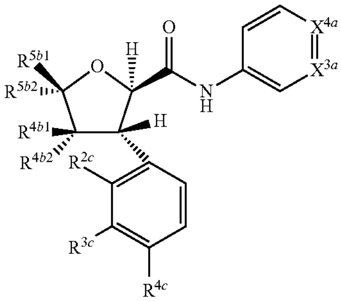

or a pharmaceutically acceptable salt thereof.

6. The compound of any one of clauses 1, 2, or 4, or the pharmaceutically acceptable salt thereof, wherein $X^{2a}$ is C—$R^{2a}$, and $R^{2a}$ is H.

7. The compound of any one of clauses 1-6, or the pharmaceutically acceptable salt thereof, wherein $X^{3a}$ is N, C—$CONR_2$, or C—$CH_{1-n}(R^A)(OH)(CH_2OH)_n$.

8. The compound of clause 7, or the pharmaceutically acceptable salt thereof, wherein $X^{3a}$ is N.

9. The compound of clause 7, or the pharmaceutically acceptable salt thereof, wherein $X^{3a}$ is C—$CH_{1-n}(R^A)(OH)(CH_2OH)_n$, and n is 0.

10. The compound of clause 7, or the pharmaceutically acceptable salt thereof, wherein $X^{3a}$ is C—$CH_{1-n}(R^A)(OH)(CH_2OH)_n$, and n is 1.

11. The compound of any one of clauses 1-8, or the pharmaceutically acceptable salt thereof, wherein $X^{4a}$ is N, C—$CONR_2$, or C—$CH_{1-n}(R^A)(OH)(CH_2OH)_n$.

12. The compound of clause 11, or the pharmaceutically acceptable salt thereof, wherein $X^{4a}$ is N.

13. The compound of clause 11, or the pharmaceutically acceptable salt thereof, wherein $X^{4a}$ is C—$CH_{1-n}(R^A)(OH)(CH_2OH)_n$, and n is 0.

14. The compound of clause 11, or the pharmaceutically acceptable salt thereof, wherein $X^{4a}$ is C—$CH_{1-n}(R^A)(OH)(CH_2OH)_n$, and n is 1.

15. The compound of any one of clauses 1-14, or the pharmaceutically acceptable salt thereof, wherein one of $X^{3a}$ and $X^{4a}$ is N and the other is C—$CONR_2$, or C—$CH_{1-n}(R^A)(OH)(CH_2OH)_n$.

16. The compound of any one of clauses 1-15, or the pharmaceutically acceptable salt thereof, wherein $R^{5b1}$ is $C_1$-$C_6$ alkyl or $C_1$-$C_6$ haloalkyl.

17. The compound of clause 16, or a pharmaceutically acceptable salt thereof, wherein $R^{5b1}$ is $CH_3$ or $CF_3$.

18. The compound of any one of clauses 1-17, or a pharmaceutically acceptable salt thereof, wherein $R^{5b2}$ is $C_1$-$C_6$ alkyl or $C_1$-$C_6$ haloalkyl.

19. The compound of clause 18, or a pharmaceutically acceptable salt thereof, wherein $R^{5b2}$ is $CH_3$ or $CF_3$.

20. The compound of any one of clauses 1-19, or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy.

21. The compound of clause 20, or a pharmaceutically acceptable salt thereof, wherein $R^{2c}$ is OH, Cl, $CH_3$, $OCH_3$, $OCD_3$, $OCH_2CH_3$, $OCH(CH_3)_2$, $OCH_2CH_2F$, or $OCH_2CHF_2$.

22. The compound of clause 21, or a pharmaceutically acceptable salt thereof, wherein $R^{2c}$ is $CH_3$ or $OCH_3$.

23. The compound of any one of clauses 1-22, or a pharmaceutically acceptable salt thereof, wherein $R^{3c}$ is halo or $C_1$-$C_6$ alkyl.

24. The compound of clause 23, or a pharmaceutically acceptable salt thereof, wherein $R^{30}$ is F.

25. The compound of clause 23, or a pharmaceutically acceptable salt thereof, wherein $R^{30}$ is $CH_3$.

26. The compound of any one of clauses 1-25, or a pharmaceutically acceptable salt thereof, wherein $R^{4c}$ is halo.

27. The compound of clause 26, or a pharmaceutically acceptable salt thereof, wherein $R^{4c}$ is F.

28. The compound of any one of clauses 1-27, or a pharmaceutically acceptable salt thereof, wherein $R^{5c}$ is H.

29. The compound of any one of clauses 1-28, or a pharmaceutically acceptable salt thereof, wherein $R^{6c}$ is H.

30. The compound of any one of clauses 1-29, or a pharmaceutically acceptable salt thereof, wherein $R^{4b2}$ is $C_1$-$C_6$ alkoxy.

31. The compound of clause 30, or a pharmaceutically acceptable salt thereof, wherein $R^{4b2}$ is $OCH_2CH_3$ or $OCH_3$.

32. The compound of clause 31, or a pharmaceutically acceptable salt thereof, wherein $R^{4b2}$ is $OCH_3$.

33. The compound of any one of clauses 1-29, or a pharmaceutically acceptable salt thereof, wherein $R^{4b1}$ is $C_1$-$C_6$ alkoxy.

34. The compound of clause 33, or a pharmaceutically acceptable salt thereof, wherein $R^{4b1}$ is $OCH_2CH_3$ or $OCH_3$.

35. The compound of clause 34, or a pharmaceutically acceptable salt thereof, wherein $R^{4b1}$ is $OCH_3$.

36. A compound selected from Table A, or a pharmaceutically acceptable salt thereof.

37. The compound of any one of clauses 1-36 in non-salt form.

38. A pharmaceutical composition comprising a therapeutically effective amount of the compound of any one of clauses 1-36, or a pharmaceutically acceptable salt thereof, or the compound of clause 37 and one or more pharmaceutically acceptable carriers or vehicles.

39. A pharmaceutical composition comprising the compound of any one of clauses 1-32, or a pharmaceutically acceptable salt thereof, or the compound of clause 37 and one or more pharmaceutically acceptable carriers or vehicles.

40. A method of inhibiting a voltage-gated sodium channel in a subject comprising administering to the subject the compound of any one of clauses 1-36, or a pharmaceutically acceptable salt thereof, the compound of clause 37, or the pharmaceutical composition of clause 38 or 39.

41. The method of clause 40, wherein the voltage-gated sodium channel is $Na_V1.8$.

42. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of any one of clauses 1-36, or a pharmaceutically acceptable salt thereof, the compound of clause 37, or the pharmaceutical composition of clause 38 or 39.

43. The method of clause 42, where the method comprises treating or lessening the severity in the subject of neuropathic pain.

44. The method of clause 43, wherein the neuropathic pain comprises post-herpetic neuralgia.

45. The method of clause 43, wherein the neuropathic pain comprises small-fiber neuropathy.

46. The method of clause 43, wherein the neuropathic pain comprises idiopathic small-fiber neuropathy.

47. The method of clause 43, wherein the neuropathic pain comprises diabetic neuropathy.

48. The method of clause 42, wherein the diabetic neuropathy comprises diabetic peripheral neuropathy.

49. The method of clause 42, wherein the method comprises treating or lessening the severity in the subject of musculoskeletal pain.

50. The method of clause 49, wherein the musculoskeletal pain comprises osteoarthritis pain.

51. The method of clause 42, wherein the method comprises treating or lessening the severity in the subject of acute pain.

52. The method of clause 51, wherein the acute pain comprises acute post-operative pain.

53. The method of clause 42, wherein the method comprises treating or lessening the severity in the subject of postsurgical pain.

54. The method of clause 53, wherein the postsurgical pain comprises bunionectomy pain.

55. The method of clause 53, wherein the postsurgical pain comprises abdominoplasty pain.

56. The method of clause 53, wherein the postsurgical pain comprises herniorrhaphy pain.

57. The method of clause 42, wherein the method comprises treating or lessening the severity in the subject of visceral pain.

58. The method of any one of clauses 40-57, wherein said subject is treated with one or more additional therapeutic agents administered concurrently with, prior to, or subsequent to treatment with the compound, pharmaceutically acceptable salt, or pharmaceutical composition.

59. Use of the compound of any one of clauses 1-36, or a pharmaceutically acceptable salt thereof, the compound of clause 33, or the pharmaceutical composition of clause 38 or 39, as a medicament.

EXAMPLES

General methods. $^1$H NMR spectra were obtained as solutions in an appropriate deuterated solvent such as dimethyl sulfoxide-$d_6$ (DMSO-d6).

Compound purity, retention time, and electrospray mass spectrometry (ESI-MS) data were determined by LC/MS analysis. LC/MS analysis was conducted using an Acquity UPLC BEH $C_8$ column (50×2.1 mm, 1.7 m particle) made by Waters (pn: 186002877) with a (2.1×5 mm, 1.7 m particle) guard column (pn: 186003978), and a dual gradient run from 2-98% mobile phase B over 4.45 minutes. Mobile phase A=$H_2O$ (10 mM ammonium formate with 0.05% ammonium hydroxide). Mobile phase B=acetonitrile. Flow rate=0.6 mL/min, injection volume=2 μL, and column temperature=45° C.

X-ray powder diffraction analysis method: X-ray powder diffraction (XRPD) analysis was performed at room temperature in transmission mode using a PANalytical Empyrean system equipped with a sealed tube source and a PIXcel 3D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

Abbreviations

Unless otherwise noted, or where the context dictates otherwise, the following abbreviations shall be understood to have the following meanings:

| Abbreviation | Meaning |
|---|---|
| NMR | Nuclear magnetic resonance |
| ESI-MS | Electrospray mass spectrometry |
| LC/MS | Liquid chromatography-mass spectrometry |
| HPLC | High performance liquid chromatography |
| SFC | Supercritical fluid chromatography |
| ESI | Electrospray ionization |
| g | Grams |
| mg | Milligrams |
| L | Liter(s) |
| mL | Milliliters |
| μL | Microliters |
| nL | Nanoliters |
| mmol | Millimoles |

-continued

| Abbreviation | Meaning |
|---|---|
| hr, h | Hours |
| min | Minutes |
| mm | Millimeters |
| μm | Micrometers |
| nm | Nanometer |
| MHz | Megahertz |
| Hz | Hertz |
| N | Normal (concentration) |
| M | Molar (concentration) |
| mM | Millimolar (concentration) |
| μM | Micromolar (concentration) |
| ppm | Parts per million |
| % w/v | Weight-volume concentration |
| CBS | Corey-Bakshi-Shibata |
| DCC | N,N'-Dicyclohexylcarbodiimide |
| DCM | Dichloromethane |
| DIBAL | Diisobutylaluminium hydride |
| DIEA, DIPEA | N,N-Diisopropyl ethyl amine |
| DMAP | 4-Dimethylaminopyridine |
| DME | Dimethoxyethane |
| DMF | N,N-Dimethylformamide |
| DMSO | Dimethyl sulfoxide |
| DRG | Dorsal root ganglia |
| EtOH | Ethanol |
| EtOAc | Ethyl acetate |
| T3P | Propylphosphonic anhydride, i.e., 2,4,6-tripropyl-1,3,5,2,4,6-trioxatriphosphinane 2,4,6-trioxide |
| LiHMDS | Lithium bis(trimethylsilyl)amide; Lithium hexamethyldisilazane |
| 2-MeTHF | 2-Methyltetrahydrofuran |
| MeCN | Methyl cyanide |
| MeOH | Methanol |
| MTBE | Methyl tert-butyl ether |
| NBS | N-Bromosuccinimide |
| NIS | N-Iodosuccinimide |
| NMP | N-Methylpyrrolidone |
| NMO | N-Methylmorpholine-N-oxide |
| TCFH | N,N,N',N'-Tetramethylchloroformamidinium hexafluorophosphate |
| TFA | Trifluoroacetic acid |
| THF | Tetrahydrofuran |
| TMSCN | Trimethylsilyl cyanide |
| TPPO | Triphenylphosphine oxide |
| p-TsOH | p-Toluenesulfonic acid |
| RT | Room temperature |
| EVIPR/E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-Hydroxyethyl)piperazin-1-yl]ethanesulfonic acid |
| $DiSBAC_6(3)$ | Bis-(1,3-dihexyl-thiobarbituric acid) trimethine oxonol |
| CC2-DMPE | Chlorocoumarin-2-dimyristoyl phosphatidylethanolamine |
| VABSC-1 | Voltage Assay Background Suppression Compound |
| HS | Human serum |
| BSA | Bovine serum albumin |
| SCX | Strong cation exchange |
| wt % | Percentage by weight |
| w/w | Weight-weight concentration |

Example 1

4-((2R,3R,4S,5R)-3-(3,4-difluoro-2-methoxyphenyl)-4-methoxy-5-methyl-5-(trifluoromethyl)tetrahydrofuran-2-carboxamido)picolinamide (1)

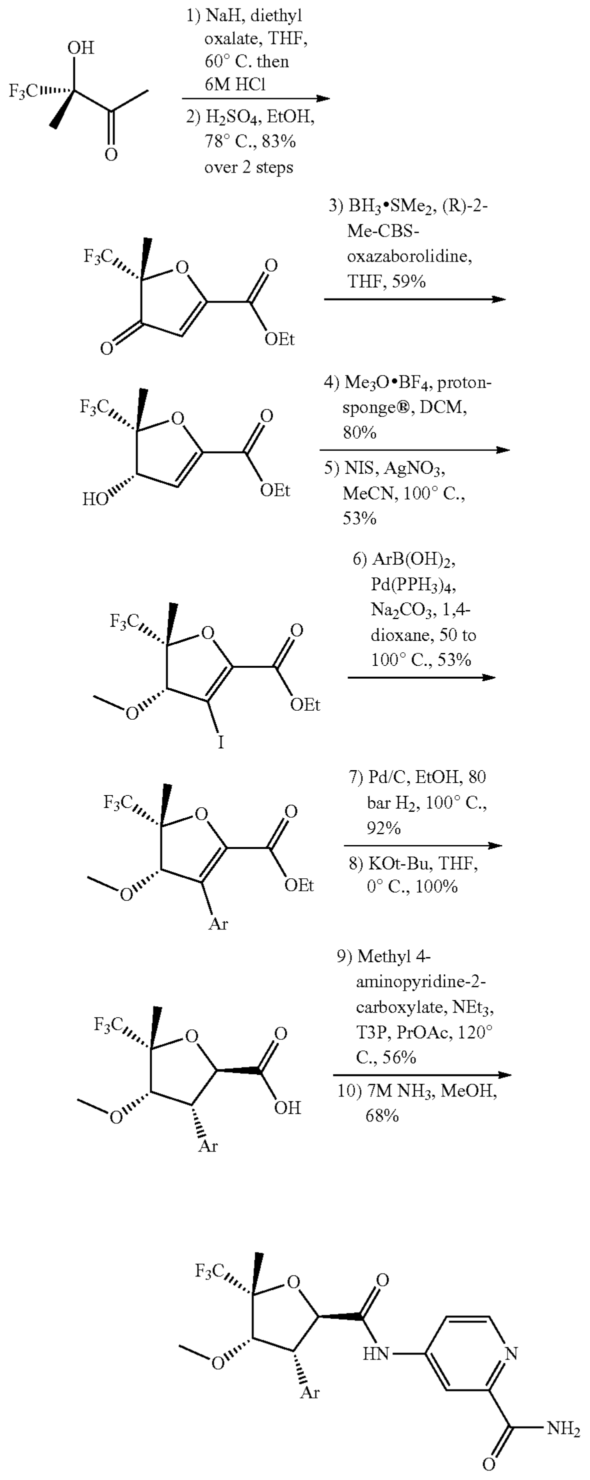

1

-continued

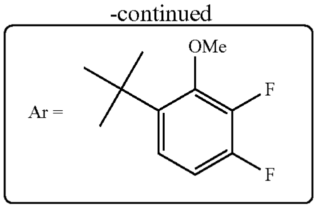

Step 1 and 2:

A solution of diethyl oxalate (17.40 mL, 128.1 mmol) and (R)-4,4,4-trifluoro-3-hydroxy-3-methylbutan-2-one (Intermediate H) (20.0 g, 128.1 mmol) in THF (80.00 mL) was added to a stirred suspension of NaH (10.8 g, 270.0 mmol) in dry THF (140.0 mL) over 1 h at such a speed to keep the gas evolution at a steady rate and the internal temperature below 40° C. After complete addition, the mixture was heated overnight at 60° C. The reaction mixture was cooled down to ambient temperature and poured into ice/water (400 ml, 20 vol). The measured pH of the solution was 11-12. The mixture was extracted twice with MTBE (5 vol, 100 ml). The resulting aqueous solution was poured into a 6 M HCl (25 vol, 500 ml) solution ensuring that the pH was 1. The mixture was extracted with MTBE (3×100 mL, 5 vol). The combined extracts were dried ($MgSO_4$), filtered and concentrated in vacuo to give a brown oil, which was used as is in the next step. The oil was solubilized in absolute EtOH (160 mL) and $H_2SO_4$ (1.4 mL, 26.26 mmol) was added. The reaction mixture was heated to reflux temperature for 3 h. A further amount of $H_2SO_4$ (5.5 mL, 103.2 mmol) was added and the heating was continued overnight. The reaction mixture was cooled down to ambient temperature and concentrated in vacuo (30 mbar and 35° C.) to give a brown oil. The crude oil was partitioned between $NaHCO_3$ and DCM. The aqueous phase was further extracted with DCM. The combined organic layers were dried ($MgSO_4$), filtered and concentrated in vacuo (250 mbar, 32° C.) to give ethyl (R)-5-methyl-4-oxo-5-(trifluoromethyl)-4,5-dihydrofuran-2-carboxylate (30.3 g, 83%) as a brown oil containing 15.5 wt % DCM. $^1H$ NMR (400 MHz, DMSO-$d_6$) δ 6.70 (s, 1H), 4.38 (q, J=7.1 Hz, 2H), 1.66 (d, J=0.9 Hz, 3H), 1.31 (t, J=7.1 Hz, 3H) ppm.

Step 3:

Borane dimethyl sulfide (20 mL of 2 M, 40.00 mmol) was added dropwise over 3 min to a solution of ethyl (R)-5-methyl-4-oxo-5-(trifluoromethyl)-4,5-dihydrofuran-2-carboxylate (7.92 g, 33.25 mmol) and (R)-(+)-2-methyl-CBS-oxazaborolidine (3.3 mL of 1 M solution in toluene, 3.30 mmol) in THF (150 mL). The reaction mixture was stirred at ambient temperature for 2 h. The reaction was quenched by addition of 1M HCl solution and diluted with MTBE (150 mL). The layers were separated and the aqueous phase was extracted with MTBE (50 mL). The combined organic layers were dried ($MgSO_4$) and concentrated in vacuo. The residue was passed through a plug of silica (50 g), washing with MTBE (250 mL), and the filtrate purified by flash chromatography (120 g $SiO_2$, 0 to 100% MTBE in hexanes) to give ethyl (4S,5R)-4-hydroxy-5-methyl-5-(trifluoromethyl)-4,5-dihydrofuran-2-carboxylate (4.7 g, 59%). $^1H$ NMR (500 MHz, Chloroform-d) δ 6.00 (dd, J=2.8, 0.7 Hz, 1H), 4.85 (d, J=2.8 Hz, 1H), 4.32 (q, J=7.1 Hz, 2H), 1.54 (q, J=1.0 Hz, 3H), 1.35 (t, J=7.1 Hz, 3H) ppm; alcohol OH not observed. ESI-MS m/z calc. 240.06094, found 242.8 $(M+1)^+$; Retention time: 0.74 minutes.

Step 4:

Proton-Sponge® (1,8-bis(dimethylamino)naphthalene; 42 g, 196.0 mmol) and trimethyloxonium tetrafluoroborate (30 g, 202.8 mmol) were successively added to a solution of ethyl (4S,5R)-4-hydroxy-5-methyl-5-(trifluoromethyl)-4,5-dihydrofuran-2-carboxylate (16.2 g, 67.45 mmol) in DCM (300 mL). The reaction mixture was stirred in the dark at ambient temperature for 3 days, then passed through a SCX-2 cartridge, washing with MTBE (500 mL). The combined organic layers were washed with 1M HCl (10×50 mL). The combined aqueous extracts were back-extracted with MTBE (2×100 mL). The combined organic extracts were washed with brine. Purification by flash chromatography ($SiO_2$, 0 to 50% MTBE in hexanes) gave ethyl (4S,5R)-4-methoxy-5-methyl-5-(trifluoromethyl)-4,5-dihydrofuran-2-carboxylate (16.6 g, 80%). $^1$H NMR (500 MHz, Chloroform-d) δ 6.06 (t, J=2.1 Hz, 1H), 4.46 (t, J=2.1 Hz, 1H), 4.30 (qd, J=7.1, 1.7 Hz, 2H), 3.43 (d, J=1.7 Hz, 3H), 1.66-1.49 (m, 3H), 1.33 (td, J=7.1, 1.7 Hz, 3H) ppm.

Step 5:

Silver nitrate (10.9 g, 64.17 mmol) and NIS (15.9 g, 70.67 mmol) were added to a stirred solution of ethyl (4S,5R)-4-methoxy-5-methyl-5-(trifluoromethyl)-4,5-dihydrofuran-2-carboxylate (19.6 g, 64.00 mmol) in MeCN (200 mL) under nitrogen. The reaction was heated to 100° C. for 24 h. The reaction mixture was cooled down to ambient temperature and quenched by addition of saturated aqueous $Na_2S_2O_3$ (100 mL). The mixture was filtered and the filtrate diluted in MTBE (200 mL). The layers were separated. The aqueous layer was extracted with MTBE (100 mL). The combined organic layers were washed with a saturated $NaHCO_3$ solution (8×100 mL), water (20 mL), brine (20 mL), dried ($MgSO_4$), filtered and concentrated in vacuo. The residue was recrystallised from EtOAc to give ethyl (4R,5R)-3-iodo-4-methoxy-5-methyl-5-(trifluoromethyl)-4,5-dihydrofuran-2-carboxylate (6 g), as pale yellow needles. The mother liquors, still containing product, were purified by flash chromatography (220 g $SiO_2$, 0 to 30% MTBE in hexanes) to give a further 6.8 g of product. A total of 12.8 g (53%) of ethyl (4R,5R)-3-iodo-4-methoxy-5-methyl-5-(trifluoromethyl)-4,5-dihydrofuran-2-carboxylate was obtained. $^1$H NMR (500 MHz, Chloroform-d) δ 4.42-4.27 (m, 3H), 3.64 (s, 3H), 1.63 (d, J=1.0 Hz, 3H), 1.39 (t, J=7.1, 7.1 Hz, 3H) ppm. ESI-MS m/z calc. 379.97324, found 381.4 $(M+1)^+$; Retention time: 0.93 minutes.

Step 6:

A mixture of ethyl (4R,5R)-3-iodo-4-methoxy-5-methyl-5-(trifluoromethyl)-4,5-dihydrofuran-2-carboxylate (6 g, 15.79 mmol), (3,4-difluoro-2-methoxyphenyl)boronic acid (3.9 g, 20.75 mmol), $Pd(PPh_3)_4$ (990 mg, 0.8567 mmol) and sodium carbonate (25 mL of 2 M aqueous solution, 50.00 mmol) in 1,4-dioxane (150 mL) was heated at 50° C. for 2 h, 70° C. for 2 h and then 100° C. (reflux) for 16 h. The reaction mixture was cooled to ambient temperature, acidified to pH 1 and partitioned between water (150 mL) and EtOAc (300 mL). The layers were separated. The aqueous layer extracted with EtOAc. The combined organic layers were washed with water and brine, dried ($MgSO_4$), filtered and concentrated in vacuo. The residue was diluted in EtOH (100 mL) and $H_2SO_4$ (900 µL, 16.88 mmol) was added. The mixture was heated at reflux for 3 h. Purification by flash chromatography ($SiO_2$, 0 to 35% EtOAc in heptane) gave ethyl (4S,5R)-3-(3,4-difluoro-2-methoxyphenyl)-4-methoxy-5-methyl-5-(trifluoromethyl)-4,5-dihydrofuran-2-carboxylate (3.3 g, 53%). ESI-MS m/z calc. 396.0996, found 395.5 (M−1); Retention time: 1.03 minutes.

Step 7:

A solution of ethyl (4S,5R)-3-(3,4-difluoro-2-methoxyphenyl)-4-methoxy-5-methyl-5-(trifluoromethyl)-4,5-dihydrofuran-2-carboxylate (330 mg, 0.83 mmol) in EtOH (15 mL) was cycled through an H-cube fitted with a Pd/C cartridge for 3.5 h. The reaction was carried out at 100° C. and 80 bar of hydrogen with a flow rate of 0.5 m/min. The resultant solution was concentrated in vacuo to give ethyl (2S,3R,4S,5R)-3-(3,4-difluoro-2-methoxyphenyl)-4-methoxy-5-methyl-5-(trifluoromethyl)tetrahydrofuran-2-carboxylate (304 mg, 92%) as a crystalline solid. $^1$H NMR (500 MHz, Chloroform-d) δ 7.25-7.22 (m, 1H), 6.85-6.78 (m, 1H), 4.79 (d, J=8.0 Hz, 1H), 4.49 (t, J=7.6, 7.6 Hz, 1H), 4.01-3.92 (m, 6H), 3.16 (s, 3H), 1.54 (s, 3H), 0.96 (t, J=7.1, 7.1 Hz, 3H) ppm. ESI-MS m/z calc. 398.11526, found 399.6 $(M+1)^+$; Retention time: 0.99 minutes.

Step 8:

KOt-Bu (3.0 g, 26.74 mmol) was added to a solution of ethyl (2S,3R,4S,5R)-3-(3,4-difluoro-2-methoxyphenyl)-4-methoxy-5-methyl-5-(trifluoromethyl)tetrahydrofuran-2-carboxylate (3.4 g, 7.60 mmol) in THF (30 mL) at 0° C. The reaction mixture was stirred at 0° C. for 5 min. The solution was acidified to pH 1 by addition of 1M HCl (50 mL). The mixture was extracted with EtOAc (3×50 mL). The combined organic extracts were washed with brine (20 mL), dried ($MgSO_4$), filtered and concentrated in vacuo to give (2R,3R,4S,5R)-3-(3,4-difluoro-2-methoxyphenyl)-4-methoxy-5-methyl-5-(trifluoromethyl)tetrahydrofuran-2-carboxylic acid (2.81 g, 100%) as a pale yellow oil, which was used in the next step without any further purification. ESI-MS m/z calc. 370.08395, found 369.7 $(M-1)^-$; Retention time: 0.49 minutes.

Step 9:

A solution of (2R,3R,4S,5R)-3-(3,4-difluoro-2-methoxyphenyl)-4-methoxy-5-methyl-5-(trifluoromethyl)tetrahydrofuran-2-carboxylic acid (130 mg, 0.35 mmol), methyl 4-aminopyridine-2-carboxylate (60 mg, 0.39 mmol), $NEt_3$ (100 µL, 0.72 mmol) and T3P (50% wt. % solution in EtOAc, 180 µL, 0.80 mmol) in isopropyl acetate (2 mL) was stirred in a sealed vessel at 120° C. for 1 h. The reaction mixture was cooled down to ambient temperature. The suspension was diluted with EtOAc, washed with water and brine. The organic layer was dried ($MgSO_4$), filtered and concentrated in vacuo to give methyl 4-((2R,3R,4S,5R)-3-(3,4-difluoro-2-methoxyphenyl)-4-methoxy-5-methyl-5-(trifluoromethyl)tetrahydrofuran-2-carboxamido)picolinate (100 mg, 56%). ESI-MS m/z calc. 504.132, found 505.7 $(M+1)^+$; Retention time: 0.92 minutes.

Step 10:

A solution of methyl 4-((2R,3R,4S,5R)-3-(3,4-difluoro-2-methoxyphenyl)-4-methoxy-5-methyl-5-(trifluoromethyl)tetrahydrofuran-2-carboxamido)picolinate (714 mg, 1.42 mmol) in methanolic ammonia (10 mL of 7 M, 70.00 mmol) and MeOH (10 mL) was stirred at ambient temperature for 2.5 days. A further amount of methanolic ammonia (10 mL of 7 M, 70.00 mmol) was added and the reaction was stirred at ambient temperature for a further 24 h. The mixture was concentrated in vacuo. Purification by chiral SFC using a (R,R)-Whelk-O1 column, 5 m particle size, 25 cm×21.1 mm from Daicel on a Minigram SFC instrument from Berger Instruments (gradient 15% to 22% MeOH in 6 min, 85 mg/ml, 35 mg, then ramp to 40% MeOH; 20 mM ammonia) gave 4-((2R,3R,4S,5R)-3-(3,4-difluoro-2-methoxyphenyl)-4-methoxy-5-methyl-5-(trifluoromethyl)tetrahydrofuran-2-carboxamido)picolinamide (1, 470 mg, 68%) as a yellow solid. $^1$H NMR (500 MHz, Chloroform-d) δ 8.58 (s, 1H), 8.48 (d, J=5.6 Hz, 1H), 8.17 (dd, J=5.5, 2.1 Hz, 1H), 7.94 (d, J=2.1 Hz, 1H), 7.91 (s, 1H), 7.31-7.27 (m, 1H), 6.97 (td, J=9.3, 7.6 Hz, 1H), 5.58 (s, 1H), 5.08 (d, J=11.6 Hz, 1H), 4.02 (d, J=2.5 Hz, 3H), 3.95 (dd, J=11.8, 4.9 Hz, 1H), 3.87 (d, J=4.9 Hz, 1H), 3.02 (s, 3H), 1.67 (s, 3H) ppm. ESI-MS m/z calc. 489.13232, found 490.5 $(M+1)^+$; 488.7 $(M-1)^-$; Retention time: 3.08 minutes.

The following compounds were made using the method described in Example 1, except that step 4 was not required. In the case of compound 2, the conditions used for the amide coupling step 9 were those used in Example 2 step 11. In the case of compound 3, pyridazin-4-amine was used as the amide coupling partner in place of methyl 4-aminopyridine-2-carboxylate in step 9 and step 10 was not required:

| Cmpd No. | Compound Name | LC/MS | NMR (shifts in ppm) |
|---|---|---|---|
| 2 | 4-((2R,3R,4S,5R)-3-(3,4-difluoro-2-methoxyphenyl)-4-hydroxy-5-methyl-5-(trifluoromethyl)tetrahydrofuran-2-carboxamido)picolinamide | ESI-MS m/z calc. 475.11667, found 476.6 $(M + 1)^+$; 474.7 $(M - 1)^-$; Retention time: 2.53 minutes | $^1$H NMR (500 MHz, Chloroform-d) δ 8.58 (s, 1H), 8.46 (d, J = 5.6 Hz, 1H), 8.13 (dd, J = 5.5, 2.2 Hz, 1H), 7.93 (d, J = 2.2 Hz, 1H), 7.83 (s, 1H), 7.19 (ddd, J = 8.2, 5.4, 2.1 Hz, 1H), 6.98-6.89 (m, 1H), 5.56 (s, 1H), 5.18 (d, J = 11.6 Hz, 1H), 4.41 (t, J = 5.1 Hz, 1H), 4.02 (d, J = 2.7 Hz, 3H), 3.92 (dd, J = 11.7, 5.0 Hz, 1H), 2.08 (d, J = 5.1 Hz, 1H), 1.65 (s, 3H) ppm. |
| 3 | (2R,3R,4S,5R)-3-(3,4-difluoro-2-methoxyphenyl)-4-hydroxy-5-methyl-N-(pyridazin-4-yl)-5-(trifluoromethyl)tetrahydrofuran-2-carboxamide | ESI-MS m/z calc. 433.1061, found 434.5 $(M + 1)^+$; 432.5 $(M - 1)^-$; Retention time: 2.42 minutes | $^1$H NMR (500 MHz, Chloroform-d) δ 9.36 (s, 1H), 9.19 (s, 1H), 9.05 (d, J = 6.1 Hz, 1H), 8.23 (d, J = 5.2 Hz, 1H), 7.19 (t, J = 7.3 Hz, 1H), 6.94 (q, J = 8.7 Hz, 1H), 5.25 (d, J = 11.6 Hz, 1H), 4.43 (d, J = 5.0 Hz, 1H), 4.04 (d, J = 2.7 Hz, 3H), 4.00 (dd, J = 8.3, 4.0 Hz, 1H), 2.01 (s, 1H), 1.67 (s, 3H) ppm. |

The following compound was made using the method described in Example 1, except that (4-fluoro-2-methoxy-3-methylphenyl)boronic acid was used as the coupling partner in the Suzuki coupling step 6 in place of (3,4-difluoro-2-methoxyphenyl)boronic acid. In the amide coupling step 9, pyridazin-4-amine was used as the coupling partner. Step 10 was not required:

| Cmpd No. | Compound Name | LC/MS | NMR (shifts in ppm) |
|---|---|---|---|
| 4 | (2R,3R,4S,5R)-3-(4-fluoro-2-methoxy-3-methylphenyl)-4-methoxy-5-methyl-N-(pyridazin-4-yl)-5-(trifluoromethyl)tetrahydrofuran-2-carboxamide | ESI-MS m/z calc. 443.14682, found 444.2 $(M + 1)^+$; 442.1 $(M - 1)^-$; Retention time: 3.0 minutes | $^1$H NMR (400 MHz, Chloroform-d) δ 9.18 (dd, J = 2.8, 1.0 Hz, 1H), 9.02 (dd, J = 5.9, 1.0 Hz, 1H), 8.62 (s, 1H), 8.01 (dd, J = 5.9, 2.8 Hz, 1H), 7.35 (dd, J = 8.8, 6.4 Hz, 1H), 6.90 (t, J = 8.7 Hz, 1H), 5.07 (d, J = 11.7 Hz, 1H), 3.98 (dd, J = 11.7, 4.8 Hz, 1H), 3.81 (d, J = 4.8 Hz, 1H), 3.72 (s, 3H), 2.94 (s, 3H), 2.23 (d, J = 2.1 Hz, 3H), 1.64 (d, J = 1.0 Hz, 3H) ppm. |

Compound 4 was analyzed by X-ray powder diffraction and determined to be amorphous (see FIG. 1).

The following compound was made using the method described in Example 1, except that (4-fluoro-2-methoxy-3-methylphenyl)boronic acid was used as the coupling partner in the Suzuki coupling step 6. The amide coupling step 9 was carried out at ambient temperature over 2 h, using an excess of methyl 4-aminopicolinate as the coupling partner, in situ generation of the highly reactive acyl imidazolium ion from the combination of an excess of TCFH and 1-methylimidazole in acetonitrile as the solvent, conditions well known in the art:

| Cmpd No. | Compound Name | LC/MS | NMR (shifts in ppm) |
|---|---|---|---|
| 5 | 4-((2R,3R,4S,5R)-3-(4-fluoro-2-methoxy-3-methylphenyl)-4-methoxy-5-methyl-5-(trifluoromethyl)tetrahydrofuran-2-carboxamido)picolinamide | ESI-MS m/z calc. 485.15738, found 486.2 $(M + 1)^+$; 484.1 $(M - 1)^-$; Retention time: 3.05 minutes | $^1H$ NMR (400 MHz, Chloroform-d) δ 8.67 (t, J = 1.6 Hz, 1H), 8.41 (s, 1H), 8.15 (d, J = 1.6 Hz, 2H), 7.68 (s, 1H), 7.42-7.36 (m, 1H), 6.91 (t, J = 8.8 Hz, 1H), 5.07 (d, J = 11.7 Hz, 1H), 3.97 (dd, J = 11.7, 4.8 Hz, 1H), 3.81 (d, J = 4.8 Hz, 1H), 3.72 (s, 3H), 2.95 (s, 3H), 2.23 (d, J = 2.1 Hz, 3H), 1.65 (s, 3H) ppm; amide NH not observed. |

The following compound was made using the method described in Example 1, except that (4-fluoro-2-methoxy-3-methylphenyl)boronic acid was used as the coupling partner in the Suzuki coupling step 6. (R)-6-(2,2-dimethyl-1,3-dioxolan-4-yl)pyridin-3-amine (Intermediate C) was used as the coupling partner in the amide coupling step 9 and ethyl acetate was used as the solvent in place of isopropyl acetate. Step 10 was replaced by a deprotection step carried out at 50 (C overnight, using an excess of TFA in a 4 to 1 mixture of THF and water as the solvent:

| Cmpd No. | Compound Name | LC/MS | NMR (shifts in ppm) |
|---|---|---|---|
| 6 | (2R,3R,4S,5R)-N-(6-((R)-1,2-dihydroxyethyl)pyridin-3-yl)-3-(4-fluoro-2-methoxy-3-methylphenyl)-4-methoxy-5-methyl-5-(trifluoromethyl)tetrahydrofuran-2-carboxamide | ESI-MS m/z calc. 502.1727, found 503.2 $(M + 1)^+$; 501.2 $(M - 1)^-$; Retention time: 2.82 minutes | $^1H$ NMR (400 MHz, Methanol-$d_4$) δ 8.64 (dd, J = 2.5, 0.7 Hz, 1H), 8.01 (dd, J = 8.6, 2.5 Hz, 1H), 7.50 (dt, J = 8.6, 0.7 Hz, 1H), 7.38 (dd, J = 8.8, 6.5 Hz, 1H), 6.89 (t, J = 8.9 Hz, 1H), 5.01 (d, J = 11.4 Hz, 1H), 4.70 (dd, J = 6.6, 4.2 Hz, 1H), 4.16 (dd, J = 11.4, 4.9 Hz, 1H), 3.93 (d, J = 4.9 Hz, 1H), 3.81-3.77 (m, 1H), 3.76 (s, 3H), 3.64 (dd, J = 11.3, 6.7 Hz, 1H), 2.94 (s, 3H), 2.20 (d, J = 2.1 Hz, 3H), 1.62 (d, J = 1.1 Hz, 3H) ppm; alcohols OH and amide NH not observed. |

The following compound was made using the method described in Example 1, except that the Suzuki coupling step 6 was carried out over 50 min at 50° C. using (3,4-difluoro-2-methylphenyl)boronic acid as the coupling partner, Pd(dppf)$Cl_2$·DCM as the catalyst, $K_3PO_4$ as the base in a 10:1 mixture of 1,4-dioxane and water as the solvent. The hydrogenation step 7 was carried out over 48 h with 19 bar of hydrogen in the presence of Pearlman's catalyst in ethanol as the solvent. The conditions used for the amide coupling step 9 were those used in Example 2 step 11 using NMP as the solvent in the second part of the reaction:

| Cmpd No. | Compound Name | LC/MS | NMR (shifts in ppm) |
|---|---|---|---|
| 7 | 4-((2R,3R,4S,5R)-3-(3,4-difluoro-2-methylphenyl)-4-methoxy-5-methyl-5-(trifluoromethyl)tetrahydrofuran-2-carboxamido)picolinamide | ESI-MS m/z calc. 473.1374, found 474.1.2 $(M + 1)^+$; Retention time: 2.19 minutes | $^1$H NMR (400 MHz, Methanol-$d_4$) δ 8.54 (d, J = 6.0 Hz, 1H), 8.44 (d, J = 2.2 Hz, 1H), 8.01 (dd, J = 6.1, 2.2 Hz, 1H), 7.30 (ddd, J = 8.9, 4.9, 1.7 Hz, 1H), 7.10 (q, J = 9.0 Hz, 1H), 5.14 (d, J = 10.7 Hz, 1H), 4.14-4.02 (m, 2H), 2.93 (s, 3H), 2.38 (d, J = 2.4 Hz, 3H), 1.62 (s, 3H) ppm; amides NH not observed. |

-continued

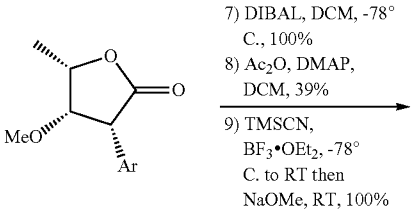

Example 2

4-((2R,3R,4S,5S)-3-(3,4-difluoro-2-methoxyphenyl)-4-methoxy-5-methyltetrahydrofuran-2-carboxamido)picolinamide (8)

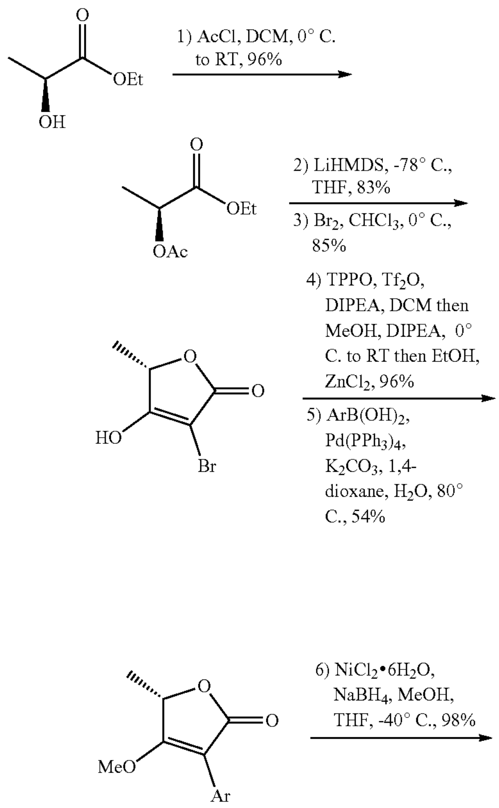

-continued

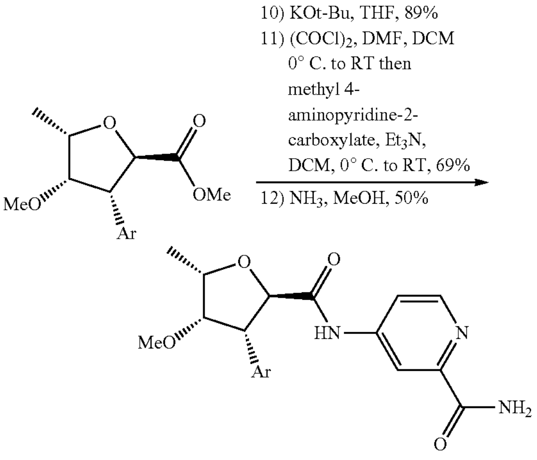

8

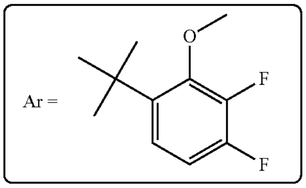

Step 1:

Acetyl chloride (9.4 mL, 132.2 mmol) was added to a stirred solution of ethyl (S)-2-hydroxypropanoate (10 mL, 88.2 mmol) in DCM (45 mL) at 0° C. The mixture was warmed up to ambient temperature and stirred for 20 h. The mixture was quenched with a saturated $NaHCO_3$ solution (40 mL) and extracted with DCM. The organic extract was dried ($Na_2SO_4$), filtered and concentrated in vacuo. Purification by flash chromatography gave ethyl (S)-2-acetoxy-propanoate (13.6 g, 96%). $^1$H NMR (400 MHz, Chloroform-d) δ 5.06 (q, J=7.1 Hz, 1H), 4.20 (q, J=7.1 Hz, 2H), 2.13 (s, 3H), 1.48 (d, J=7.1 Hz, 3H), 1.28 (t, J=7.1 Hz, 3H) ppm.

Step 2:

A solution of ethyl (S)-2-acetoxypropanoate (13.6 g, 84.91 mmol) in THF (400 mL) was added over 30 min to a stirred solution of LiHMDS (204 mL of 1 M in THF, 204.0 mmol) in THF (400 mL) at −78° C. The mixture was stirred at this temperature for 90 min before being poured onto 2 M aqueous HCl (30 mL). The layers were separated. The aqueous phase was extracted with EtOAc and the combined organic layers washed with brine. The organic layer was concentrated in vacuo, redissolved in DCM, dried ($Na_2SO_4$), filtered and concentrated in vacuo to give (S)-4-hydroxy-5-methylfuran-2(5H)-one (8 g, 83%), as a solid which was used without further purification in the next step. $^1H$ NMR (500 MHz, DMSO-$d_6$) δ 12.57 (s, 1H), 4.88 (s, 1H), 4.85 (dq, J=6.7, 0.9 Hz, 1H), 1.34 (d, J=6.7 Hz, 3H) ppm.

Step 3:

A solution of bromine (3.7 mL, 71.82 mmol) in $CHCl_3$ (450 mL) was added dropwise at 0° C. to a solution of (S)-4-hydroxy-5-methylfuran-2(5H)-one (7.8 g, 68.4 mmol) in $CHCl_3$ (280 mL). The stirring was continued at this temperature until the reaction was complete. The formed precipitate was collected by filtration to give (S)-3-bromo-4-hydroxy-5-methylfuran-2(5H)-one (11.15 g, 85%). $^1H$ NMR (500 MHz, DMSO-$d_6$) δ 4.99 (q, J=6.8 Hz, 1H), 1.40 (d, J=6.8 Hz, 3H) ppm; alcohol OH not observed.

Step 4:

Triflic anhydride (7.8 mL of 1 M in DCM, 7.80 mmol) was added to a stirred solution of TPPO (4.5 g, 16.2 mmol) in DCM (27 mL) at 0° C. After stirring for 15 min, a precipitate had formed. A solution of (S)-3-bromo-4-hydroxy-5-methylfuran-2(5H)-one (1.5 g, 7.77 mmol) and DIPEA (1.4 mL, 8.04 mmol) in DCM (40 mL) was added to the suspension. After the colourless precipitate had dissolved, MeOH (380 µL, 9.38 mmol) was added dropwise, followed by DIPEA (1.7 mL, 9.76 mmol). The reaction was warmed to ambient temperature and stirred for 20 h. The reaction mixture was concentrated in vacuo. The residue was dissolved in EtOH (50 mL) and dichlorozinc (3.6 mL, 38.81 mmol) was added. The mixture was stirred for 2 h. A precipitate was filtered off and the filtrate was concentrated in vacuo to give (S)-3-bromo-4-methoxy-5-methylfuran-2(5H)-one (1.55 g, 96%). $^1H$ NMR (500 MHz, Chloroform-d) δ 4.78 (q, J=6.7 Hz, 1H), 4.34 (s, 3H), 1.47 (d, J=6.8 Hz, 3H) ppm.

Step 5:

$K_2CO_3$ (2.8 g, 20.26 mmol), (3,4-difluoro-2-methoxyphenyl)boronic acid (926 mg, 4.93 mmol) and tetrakis(triphenylphosphine)palladium (715 mg, 0.62 mmol) were successively added to a degassed solution of (S)-3-bromo-4-methoxy-5-methylfuran-2(5H)-one (850 mg, 4.11 mmol) in 1,4-dioxane (20 mL) and water (4.2 mL). The mixture was flushed with nitrogen and heated to 80° C. for 2 h. The reaction mixture was cooled down to ambient temperature, quenched with a saturated $NH_4Cl$ solution (20 mL) and diluted with EtOAc (20 mL). The layers were separated and the aqueous phase was extracted with EtOAc (20 mL). The combined organic layers were dried ($MgSO_4$), filtered and concentrated in vacuo. Purification by flash chromatography gave (S)-3-(3,4-difluoro-2-methoxyphenyl)-4-methoxy-5-methylfuran-2(5H)-one (600 mg, 54%). $^1H$ NMR (500 MHz, Chloroform-d) δ 6.98 (ddd, J=8.7, 5.8, 2.1 Hz, 1H), 6.91 (ddd, J=9.5, 8.7, 7.2 Hz, 1H), 4.86 (q, J=6.7 Hz, 1H), 3.94 (d, J=2.0 Hz, 3H), 3.73 (s, 3H), 1.54 (d, J=6.7 Hz, 3H) ppm. ESI-MS m/z calc. 270.07037, found 271.4 $(M+1)^+$; Retention time: 2.58 minutes.

Step 6:

Nickel dichloride hexahydrate (510 mg, 2.15 mmol) and $NaBH_4$ (406 mg, 10.73 mmol) were successively added to a stirred solution of (S)-3-(3,4-difluoro-2-methoxyphenyl)-4-methoxy-5-methylfuran-2(5H)-one (580 mg, 2.146 mmol) in a mixture of MeOH (24 mL) and THF (4.6 mL) at −40° C. The resulting mixture was stirred for 15 min. The mixture was quenched by addition of a saturated aqueous $NH_4Cl$ solution (20 mL). The layers were separated and the aqueous phase was extracted with DCM (20 mL). The combined organic extracts were dried ($MgSO_4$), filtered and concentrated in vacuo to give (3R,4S,5S)-3-(3,4-difluoro-2-methoxyphenyl)-4-methoxy-5-methyldihydrofuran-2(3H)-one (575 mg, 98%). $^1H$ NMR (500 MHz, Chloroform-d) δ 7.12-7.07 (m, 1H), 6.90 (ddd, J=9.6, 8.9, 7.5 Hz, 1H), 4.67 (qd, J=6.5, 3.5 Hz, 1H), 4.30 (d, J=5.2 Hz, 1H), 4.03 (d, J=2.7 Hz, 3H), 3.93 (dd, J=5.2, 3.6 Hz, 1H), 2.98 (s, 3H), 1.47 (d, J=6.5 Hz, 3H) ppm. ESI-MS m/z calc. 272.08603, found 273.5 $(M+1)^+$; Retention time: 2.66 minutes.

Step 7:

DIBAL (2.5 mL of 1 M, 2.500 mmol) was added to a stirred solution of (3R,4S,5S)-3-(3,4-difluoro-2-methoxyphenyl)-4-methoxy-5-methyldihydrofuran-2(3H)-one (575 mg, 2.112 mmol) in DCM (8.5 mL) at −78° C. After stirring for 1 h at −78° C., a further quantity of DIBAL (2.5 mL of 1 M, 2.500 mmol) was added. Upon reaction completion, the mixture was quenched by addition of a saturated aqueous ammonium chloride solution (4 mL) and a Rochelle's salt solution (30% w/w, 4 mL). This mixture was stirred for 1 h. The layers were separated and the aqueous phase was extracted with DCM (10 mL). The combined organic layers were dried ($MgSO_4$), filtered and concentrated in vacuo to give (3R,4S,5S)-3-(3,4-difluoro-2-methoxyphenyl)-4-methoxy-5-methyltetrahydrofuran-2-ol (580 mg, 100%), which was used as is in the next step. ESI-MS m/z calc. 274.10165, found 258.5 $(M-OH)^+$; Retention time: 2.34 minutes.

Step 8:

DMAP (130 mg, 1.06 mmol) and acetic anhydride (880 mg, 8.62 mmol) were successively added to a stirred solution of (3R,4S,5S)-3-(3,4-difluoro-2-methoxyphenyl)-4-methoxy-5-methyltetrahydrofuran-2-ol (580 mg, 2.12 mmol) in DCM (6 mL) at ambient temperature. Upon reaction completion, the mixture was quenched by addition of a saturated aqueous sodium bicarbonate solution (6 mL). The mixture was stirred at ambient temperature for 30 min. The layers were separated and the aqueous phase was extracted with DCM (2×10 mL). The combined organic layers were dried ($MgSO_4$), filtered and concentrated in vacuo. Purification by flash chromatography gave (3R,4S,5S)-3-(3,4-difluoro-2-methoxyphenyl)-4-methoxy-5-methyltetrahydrofuran-2-yl acetate (260 mg, 39%) as a mixture of epimers at the $C_2$ position. ESI-MS m/z calc. 316.11224, found 258.5 $(M-OAc)^+$; Retention time: 2.94 minutes.

Step 9:

TMSCN (280 µL, 2.10 mmol) and $BF_3 \cdot OEt_2$ (330 µL of 46.5% w/w, 1.24 mmol) were successively added dropwise to a stirred solution of (3R,4S,5S)-3-(3,4-difluoro-2-methoxyphenyl)-4-methoxy-5-methyltetrahydrofuran-2-yl acetate (260 mg, 0.82 mmol) in DCM (8 mL) at −78° C. The reaction mixture was stirred at −78° C. for 30 min and then warmed up to ambient temperature. The mixture was quenched with a saturated aqueous sodium bicarbonate solution. The aqueous layer was separated and extracted with DCM (3×10 mL). The combined organic extracts were dried ($Na_2SO_4$), filtered and concentrated in vacuo. The resulting oil was dissolved in DCM and filtered through a pad of Celite. The liquors were concentrated in vacuo. The residue was dissolved in a sodium methoxide solution (2.5 mL of 0.5 M in MeOH, 1.250 mmol) and stirred at ambient temperature overnight. The reaction was quenched by addition of a saturated aqueous citric acid solution. The mixture was stirred for 30 min. After complete hydrolysis, the reaction mixture was concentrated in vacuo and the residue dissolved in DCM. The solution was washed with water (10 mL) and brine (10 mL). The combined organic extracts were dried ($MgSO_4$), filtered and concentrated in vacuo to give methyl (2R,3R,4S,5S)-3-(3,4-difluoro-2-methoxyphenyl)-4-methoxy-5-methyltetrahydrofuran-2-carboxylate (260 mg, 100%) as the main stereoisomer. $^1$H NMR (500 MHz, Chloroform-d) δ 7.20 (ddd, J=8.2, 5.8, 2.3 Hz, 1H), 6.89 (ddd, J=9.6, 8.8, 7.4 Hz, 1H), 4.74 (d, J=9.8 Hz, 1H), 4.45 (qd, J=6.4, 3.1 Hz, 1H), 4.06-4.00 (m, 1H), 3.96 (d, J=1.9 Hz, 3H), 3.68 (s, 3H), 3.67 (dd, J=4.5, 2.8 Hz, 1H), 3.02 (s, 3H), 1.35 (d, J=6.3 Hz, 3H) ppm. ESI-MS m/z calc. 316.11224, found 317.4 $(M+1)^+$; Retention time: 2.8 minutes.

Step 10:

Potassium tert-butoxide (370 mg, 3.30 mmol) was added to a stirred solution of methyl (2R,3R,4S,5S)-3-(3,4-difluoro-2-methoxyphenyl)-4-methoxy-5-methyltetrahydrofuran-2-carboxylate (260 mg, 0.82 mmol) in THF (3.2 mL) at ambient temperature. Upon reaction completion, the reaction was quenched by addition of a saturated aqueous ammonium chloride solution (3 mL) and diluted with DCM (3 mL). The layers were separated and the aqueous phase extracted with DCM (5 mL). The aqueous phase was acidified with 1M HCl until pH 0 and extracted with DCM (2×10 mL). The combined organic extracts were dried ($MgSO_4$), filtered and concentrated in vacuo to give (2R,3R,4S,5S)-3-(3,4-difluoro-2-methoxyphenyl)-4-methoxy-5-methyltetrahydrofuran-2-carboxylic acid (220 mg, 89%) as a single enantiomer. $^1$H NMR (500 MHz, Chloroform-d) δ 7.14 (ddd, J=8.5, 5.8, 2.3 Hz, 1H), 6.83 (td, J=9.3, 7.5 Hz, 1H), 4.70 (d, J=10.3 Hz, 1H), 4.37 (qd, J=6.3, 3.0 Hz, 1H), 3.92 (dd, J=10.3, 4.3 Hz, 1H), 3.90 (d, J=2.0 Hz, 3H), 3.62 (dd, J=4.3, 3.0 Hz, 1H), 2.96 (s, 3H), 1.29 (d, J=6.3 Hz, 3H) ppm; acid OH not observed. ESI-MS m/z calc. 302.0966, found 301.4 $(M-1)^-$; Retention time: 1.51 minutes.

Step 11 and 12:

Oxalyl chloride (35 μL, 0.40 mmol) was added to a stirred solution of (2R,3R,4S,5S)-3-(3,4-difluoro-2-methoxyphenyl)-4-methoxy-5-methyltetrahydrofuran-2-carboxylic acid (55 mg, 0.18 mmol) and DMF (1.5 μL, 0.019 mmol) in DCM (600 μL) at 0° C. The reaction mixture was warmed to ambient temperature over 30 min and concentrated in vacuo. The residue, re-dissolved in DCM (300 μL), was added to a stirred solution of methyl 4-aminopyridine-2-carboxylate (35 mg, 0.23 mmol) and $NEt_3$ (35 μL, 0.25 mmol) in DCM (300 μL) at 0° C. The reaction mixture was warmed to ambient temperature over 2 h. The mixture was quenched by addition of a drop of water and MeOH (2 mL) and concentrated in vacuo. Purification by flash chromatography gave methyl 4-((2R,3R,4S,5S)-3-(3,4-difluoro-2-methoxyphenyl)-4-methoxy-5-methyltetrahydrofuran-2-carboxamido)picolinate (55 mg, 69%). ESI-MS m/z calc. 436.1446, found 437.3 $(M+1)^+$; 435.4 $(M-1)^-$; Retention time: 2.77 minutes.

Methyl 4-((2R,3R,4S,5S)-3-(3,4-difluoro-2-methoxyphenyl)-4-methoxy-5-methyltetrahydrofuran-2-carboxamido)picolinate (55 mg, 0.126 mmol) was dissolved in methanolic ammonia (5 mL of 7 M, 35.00 mmol) and stirred at ambient temperature overnight. The reaction mixture was concentrated in vacuo to give 4-((2R,3R,4S,5S)-3-(3,4-difluoro-2-methoxyphenyl)-4-methoxy-5-methyltetrahydrofuran-2-carboxamido)picolinamide (8, 140 mg, 50%). $^1$H NMR (500 MHz, DMSO-$d_6$) δ 10.41 (s, 1H), 8.47 (d, J=5.5 Hz, 1H), 8.31 (d, J=1.9 Hz, 1H), 8.04 (d, J=3.0 Hz, 1H), 7.87 (dd, J=5.5, 2.2 Hz, 1H), 7.58 (d, J=3.0 Hz, 1H), 7.30 (ddd, J=8.5, 6.0, 2.2 Hz, 1H), 7.17 (ddd, J=10.1, 9.1, 7.8 Hz, 1H), 4.74 (d, J=10.1 Hz, 1H), 4.50 (qd, J=6.3, 3.0 Hz, 1H), 4.03 (dd, J=10.1, 4.4 Hz, 1H), 3.88 (d, J=1.6 Hz, 3H), 3.81 (dt, J=4.7, 3.2 Hz, 1H), 2.98 (s, 3H), 1.28 (d, J=6.3 Hz, 3H) ppm. ESI-MS m/z calc. 421.14493, found 422.5 $(M+1)^+$; 420.5 (M−1); Retention time: 2.62 minutes.

The following compounds were made using the method described in Example 2, except that different coupling partners were used in the amide coupling step 11, in the case of compound 9, rel-2-(2,2-dimethyl-1,3-dioxolan-4-yl)pyridin-4-amine (Intermediate D, first eluting peak from chiral SFC separation) was used as the coupling partner in the amide coupling step 11. In the case of compound 10, rel-2-(2,2-dimethyl-1,3-dioxolan-4-yl)pyridin-4-amine (Intermediate E, second eluting peak from chiral SFC separation) was used as the coupling partner in the amide coupling step 11. Step 12 was replaced by a deprotection step using an excess of TFA in DCM as the solvent:

| Cmpd No. | Compound Name | LC/MS | NMR (shifts in ppm) |
|---|---|---|---|
| 9 | rel-(2R*,3R*,4S*,5S*)-3-(3,4-difluoro-2-methoxyphenyl)-N-(2-(1,2-dihydroxyethyl)pyridin-4-yl)-4-methoxy-5-methyltetrahydrofuran-2-carboxamide | ESI-MS m/z calc. 438.16025, found 439.3 $(M + 1)^+$; 437.5 $(M - 1)^-$; Retention time: 2.37 minutes | $^1$H NMR (500 MHz, DMSO-$d_6$) δ 10.22 (s, 1H), 8.32 (d, J = 5.5 Hz, 1H), 7.74 (d, J = 2.2 Hz, 1H), 7.56 (dd, J = 5.6, 2.1 Hz, 1H), 7.29 (ddd, J = 8.5, 6.1, 2.2 Hz, 1H), 7.24-7.12 (m, 1H), 5.35 (d, J = 4.6 Hz, 1H), 4.73 (d, J = 10.1 Hz, 1H), 4.66 (t, J = 5.9 Hz, 1H), 4.55-4.45 (m, 2H), 4.03 (dd, J = 10.1, 4.3 Hz, 1H), 3.89 (d, J = 1.6 Hz, 3H), 3.82 (dd, J = 4.7, 3.1 Hz, 1H), 3.65 (ddd, J = 10.1, 6.1, 4.0 Hz, 1H), 3.43 (ddd, J = 11.0, 6.9, 5.8 Hz, 1H), 2.98 (s, 3H), 1.27 (d, J = 6.3 Hz, 3H) ppm. |
| 10 | rel-(2R*,3R*,4S*,5S*)-3-(3,4-difluoro-2-methoxyphenyl)-N-(2-(1,2-dihydroxyethyl)pyridin- | ESI-MS m/z calc. 438.16025, found 439.3 $(M + 1)^+$; | $^1$H NMR (500 MHz, DMSO-$d_6$) δ 10.23 (s, 1H), 8.32 (d, J = 5.5 Hz, |

-continued

| Cmpd No. | Compound Name | LC/MS | NMR (shifts in ppm) |
|---|---|---|---|
| | 4-yl)-4-methoxy-5-methyltetrahydrofuran-2-carboxamide | 437.5 $(M-1)^-$; Retention time: 2.37 minutes | 1H), 7.74 (d, J = 2.2 Hz, 1H), 7.56 (dd, J = 5.5, 2.2 Hz, 1H), 7.29 (ddd, J = 8.4, 6.0, 2.2 Hz, 1H), 7.18 (ddd, J = 10.1, 9.0, 7.7 Hz, 1H), 5.35 (d, J = 4.7 Hz, 1H), 4.73 (d, J = 10.1 Hz, 1H) 4.69-4.61 (m, 1H), 4.56-4.43 (m, 2H), 4.04 (dd, J = 10.1, 4.4 Hz, 1H), 3.89 (d, J = 1.6 Hz, 3H), 3.82 (dd, J = 4.7, 3.1 Hz, 1H), 3.65 (ddd, J = 9.8, 5.9, 3.9 Hz, 1H), 3.48-3.39 (m, 1H), 2.98 (s, 3H), 1.27 (d, J = 6.5 Hz, 3H) ppm. |

The following compounds were made using the method described in Example 2, except that rac-2-(2,2,4-trimethyl-1,3-dioxolan-4-yl)pyridin-4-amine was used as the coupling partner in the amide coupling Step 11. Step 12 was not required. The diastereoisomers from step 11 were separated by chiral SFC separation using a Chiralpak AS-H column, 5 μm particle size, 25 cm×10 mm from Daicel on a Minigram instrument from Berger Instruments (10% MeOH, 20 mM $NH_3$, 245 nm, 100 bar). A final deprotection step was carried out using an excess of TFA in DCM as the solvent:

| Cmpd No. | Compound Name | LC/MS | NMR (shifts in ppm) |
|---|---|---|---|
| 11 | rel-(2R*,3R*,4S*,5S*)-3-(3,4-difluoro-2-methoxyphenyl)-N-(2-(1,2-dihydroxypropan-2-yl)pyridin-4-yl)-4-methoxy-5-methyltetrahydrofuran-2-carboxamide (Precursor was the first eluting peak by SFC on Chiralpak AS-H column, rt = 3.46 min) | ESI-MS m/z calc. 452.1759, found 453.6 $(M+1)^+$; 451.5 $(M-1)^-$; Retention time: 2.52 minutes | $^1H$ NMR (500 MHz, DMSO-$d_6$) δ 10.21 (s, 1H), 8.32 (d, J = 5.5 Hz, 1H), 7.84 (d, J = 2.1 Hz, 1H), 7.56 (dd, J = 5.6, 2.1 Hz, 1H), 7.28 (ddd, J = 8.3, 5.9, 2.0 Hz, 1H), 7.23-7.13 (m, 1H), 5.01 (s, 1H), 4.73 (d, J = 10.0 Hz, 1H), 4.58 (t, J = 6.0 Hz, 1H), 4.48 (qd, J = 6.3, 3.1 Hz, 1H), 4.03 (dd, J = 10.0, 4.4 Hz, 1H), 3.88 (d, J = 1.4 Hz, 3H), 3.81 (dd, J = 4.4, 2.9 Hz, 1H), 3.49 (d, J = 6.0 Hz, 2H), 2.97 (s, 3H), 1.33 (s, 3H), 1.26 (d, J = 6.3 Hz, 3H) ppm. |
| 12 | rel-(2R*,3R*,4S*,5S*)-3-(3,4-difluoro-2-methoxyphenyl)-N-(2-(1,2-dihydroxypropan-2-yl)pyridin-4-yl)-4-methoxy-5-methyltetrahydrofuran-2-carboxamide (Precursor was the second eluting peak by SFC on Chiralpak AS-H column, rt = 3.91 min) | ESI-MS m/z calc. 452.1759, found 453.6 $(M+1)^+$; 451.5 $(M-1)^-$; Retention time: 2.52 minutes | $^1H$ NMR (500 MHz, DMSO-$d_6$) δ 10.21 (s, 1H), 8.32 (d, J = 5.5 Hz, 1H), 7.84 (dd, J = 2.0, 0.6 Hz, 1H), 7.56 (dd, J = 5.6, 2.1 Hz, 1H), 7.28 (ddd, J = 8.4, 6.0, 2.0 Hz, 1H), 7.22-7.12 (m, 1H), 5.01 (s, 1H), 4.73 (d, J = 10.0 Hz, 1H), 4.57 (t, J = 6.0 Hz, 1H), 4.49 (qd, J = 6.3, 3.0 Hz, 1H), 4.03 (dd, J = 10.1, 4.3 Hz, 1H), 3.88 (d, J = 1.5 Hz, 3H), 3.81 (dd, J = 4.4, 3.1 Hz, 1H), 3.49 (d, J = 5.9 Hz, 2H), 2.97 (s, 3H), 1.33 (s, 3H), 1.26 (d, J = 6.3 Hz, 3H) ppm. |

The following compound was made using the method described in Example 2, except that ethanol was used in place of methanol in the Hendrickson's O-alkylation step 4 and the second part of the step using $ZnCl_2$ in EtOH was not needed:

| Cmpd No. | Compound Name | LC/MS | NMR (shifts in ppm) |
|---|---|---|---|
| 13 | 4-((2R,3R,4S,5S)-3-(3,4-difluoro-2-methoxyphenyl)-4-ethoxy-5-methyltetrahydrofuran-2-carboxamido)picolinamide | ESI-MS m/z calc. 435.16058, found 436.0 $(M + 1)^+$; 434.0 $(M - 1)^-$; Retention time: 2.84 minutes | $^1H$ NMR (500 MHz, DMSO-$d_6$) δ 10.41 (s, 1H), 8.47 (d, J = 5.5 Hz, 1H), 8.32 (d, J = 2.2 Hz, 1H), 8.04 (d, J = 2.8 Hz, 1H), 7.88 (dd, J = 5.5, 2.2 Hz, 1H), 7.59 (s, 1H), 7.32 (ddd, J = 8.4, 5.9, 2.0 Hz, 1H), 7.19 (q, J = 9.0 Hz, 1H), 4.75 (d, J = 10.1 Hz, 1H), 4.50 (qd, J = 6.3, 2.9 Hz, 1H), 4.04 (dd, J = 10.2, 4.2 Hz, 1H), 3.88 (dd, J = 7.8, 2.7 Hz, 4H), 3.24 (dq, J = 9.6, 6.9 Hz, 1H), 2.95 (dq, J = 9.6, 7.0 Hz, 1H), 1.28 (d, J = 6.2 Hz, 3H), 0.87 (t, J = 7.0 Hz, 3H) ppm. |

The following compounds were made using the method described in Example 2, except that isopropanol was used in place of methanol in the Hendrickson's O-alkylation step 4 and the second part of the step using $ZnCl_2$ in EtOH was not needed. In the case of compound 15, methyl 5-aminopicolinate was used as the coupling partner in the amide coupling step 11:

| Cmpd No. | Compound Name | LC/MS | NMR (shifts in ppm) |
|---|---|---|---|
| 14 | 4-((2R,3R,4S,5S)-3-(3,4-difluoro-2-methoxyphenyl)-4-isopropoxy-5-methyltetrahydrofuran-2-carboxamido)picolinamide | ESI-MS m/z calc. 449.17624, found 450.0 $(M + 1)^+$; 448.1 $(M - 1)^-$; Retention time: 3.00 minutes | $^1H$ NMR (500 MHz, DMSO-$d_6$) δ 10.42 (s, 1H), 8.46 (d, J = 5.5 Hz, 1H), 8.31 (d, J = 2.4 Hz, 1H), 8.04 (d, J = 2.7 Hz, 1H), 7.86 (dd, J = 5.5, 2.2 Hz, 1H), 7.58 (d, J = 2.8 Hz, 1H), 7.28 (ddd, J = 8.2, 6.0, 2.2 Hz, 1H), 7.18 (ddd, J = 10.1, 9.0, 7.6 Hz, 1H), 4.75 (d, J = 10.1 Hz, 1H), 4.48 (qd, J = 6.2, 2.8 Hz, 1H), 4.02 (dd, J = 10.2, 4.3 Hz, 1H), 3.98 (dd, J = 4.3, 2.9 Hz, 1H), 3.88 (d, J = 1.4 Hz, 3H), 3.07 (hept, J = 6.0 Hz, 1H), 1.25 (d, J = 6.3 Hz, 3H), 0.98 (d, J = 6.0 Hz, 3H), 0.60 (d, J = 6.0 Hz, 3H) ppm. |
| 15 | 5-((2R,3R,4S,5S)-3-(3,4-difluoro-2-methoxyphenyl)-4-isopropoxy-5-methyltetrahydrofuran-2-carboxamido)picolinamide | ESI-MS m/z calc. 449.17624, found 450.0 $(M + 1)^+$; 448.1 $(M - 1)^-$; Retention time: 2.96 minutes | $^1H$ NMR (500 MHz, DMSO-$d_6$) δ 10.34 (s, 1H), 8.86 (d, J = 2.4 Hz, 1H), 8.24-8.17 (m, 1H), 7.97 (d, J = 8.5 Hz, 2H), 7.49 (s, 1H), 7.29 (ddd, J = 8.2, 6.1, 2.2 Hz, 1H), 7.23-7.12 (m, 1H), 4.78 (d, J = 10.2 Hz, 1H), 4.47 (dp, J = 6.3, 3.2 Hz, 1H), 4.04 (dd, J = 10.2, 4.4 Hz, 1H), 4.00-3.95 (m, 1H), 3.89 (d, J = 1.6 Hz, 3H), |

-continued

| Cmpd No. | Compound Name | LC/MS | NMR (shifts in ppm) |
|---|---|---|---|
| | | | 3.07 (hept, J = 6.2 Hz, 1H), 1.26 (d, J = 6.3 Hz, 3H), 0.98 (d, J = 6.1 Hz, 3H), 0.61 (d, J = 6.1 Hz, 3H) ppm. |

The following compounds were made using the method described in Example 2, except that isopropanol was used in place of methanol in the Hendrickson's O-alkylation step 4 and the second part of the step using $ZnCl_2$ in EtOH was not needed. In the case of compound 16, (R)-6-(2,2-dimethyl-1,3-dioxolan-4-yl)pyridin-3-amine (Intermediate C) was used as the coupling partner in the amide coupling step 11. In the case of compound 17, 6-(((tert-butyldimethylsilyl)oxy)methyl)pyridin-3-amine was used as the coupling partner in the amide coupling step 11. In both cases, step 12 was replaced by a deprotection step carried out at 40-45° C., using an excess of TFA in a 9 to 1 mixture of DCM and water as the solvent:

| Cmpd No. | Compound Name | LC/MS | NMR (shifts in ppm) |
|---|---|---|---|
| 16 | (2R,3R,4S,5S)-3-(3,4-difluoro-2-methoxyphenyl)-N-(6-((R)-1,2-dihydroxyethyl)pyridine-3-yl)-4-isopropoxy-5-methyltetrahydrofuran-2-carboxamide | ESI-MS m/z calc. 466.19153, found 467.0 $(M + 1)^+$; 465.1 $(M - 1)^-$; Retention time: 2.72 minutes | $^1H$ NMR (500 MHz, DMSO-$d_6$) δ 10.06 (s, 1H), 8.67 (d, J = 2.7 Hz, 1H), 7.99 (dd, J = 8.5, 2.5 Hz, 1H), 7.39 (d, J = 8.7 Hz, 1H), 7.32-7.24 (m, 1H), 7.22-7.13 (m, 1H), 5.29 (d, J = 5.0 Hz, 1H), 4.73 (d, J = 9.9 Hz, 1H), 4.61 (t, J = 5.9 Hz, 1H), 4.52 (dt, J = 6.8, 4.5 Hz, 1H), 4.50-4.41 (m, 1H), 4.01 (dd, J = 10.0, 4.2 Hz, 1H), 3.99-3.94 (m, 1H), 3.88 (d, J = 1.4 Hz, 3H), 3.62 (ddd, J = 10.2, 6.1, 4.0 Hz, 1H), 3.43 (dt, J = 10.9, 6.4 Hz, 1H), 3.06 (hept, J = 6.2 Hz, 1H), 1.25 (d, J = 6.3 Hz, 3H), 0.98 (d, J = 6.0 Hz, 3H), 0.60 (d, J = 6.0 Hz, 3H) ppm. |
| 17 | (2R,3R,4S,5S)-3-(3,4-difluoro-2-methoxyphenyl)-N-(6-(hydroxymethyl)pyridin-3-yl)-4-isopropoxy-5-methyltetrahydrofuran-2-carboxamide | ESI-MS m/z calc. 436.18097, found 437.0 $(M + 1)^+$; 435.1 $(M - 1)^-$; Retention time: 2.83 minutes | $^1H$ NMR (500 MHz, DMSO-$d_6$) δ 10.20 (s, 1H), 8.78 (d, J = 2.5 Hz, 1H), 8.15 (dd, J = 8.6, 2.4 Hz, 1H), 7.50 (d, J = 8.6 Hz, 1H), 7.29 (ddd, J = 8.4, 5.9, 2.0 Hz, 1H), 7.18 (td, J = 9.5, 7.6 Hz, 1H), 4.76 (d, J = 10.1 Hz, 1H), 4.57 (s, 2H), 4.47 (qd, J = 6.2, 2.8 Hz, 1H), 4.02 (dd, J = 10.1, 4.2 Hz, 1H), 3.98 (dd, J = 4.3, 2.9 Hz, 1H), 3.89 (d, J = 1.4 Hz, 3H), 3.07 (hept, J = 6.0 Hz, 1H), 1.27 (d, J = 6.2 Hz, 3H), 0.99 (d, J = 6.0 Hz, 3H), 0.61 (d, J = 6.0 Hz, 3H) ppm; alcohol OH not observed. |

Example 3 rel-4-((2R,3R,4S)-3-(3,4-difluoro-2-methoxyphenyl)-4-methoxy-5,5-dimethyltetrahydrofuran-2-carboxamido)picolinamide (18) and rel-4-((2S,3S,4R)-3-(3,4-difluoro-2-methoxyphenyl)-4-methoxy-5,5-dimethyltetrahydrofuran-2-carboxamido) picolinamide (19)

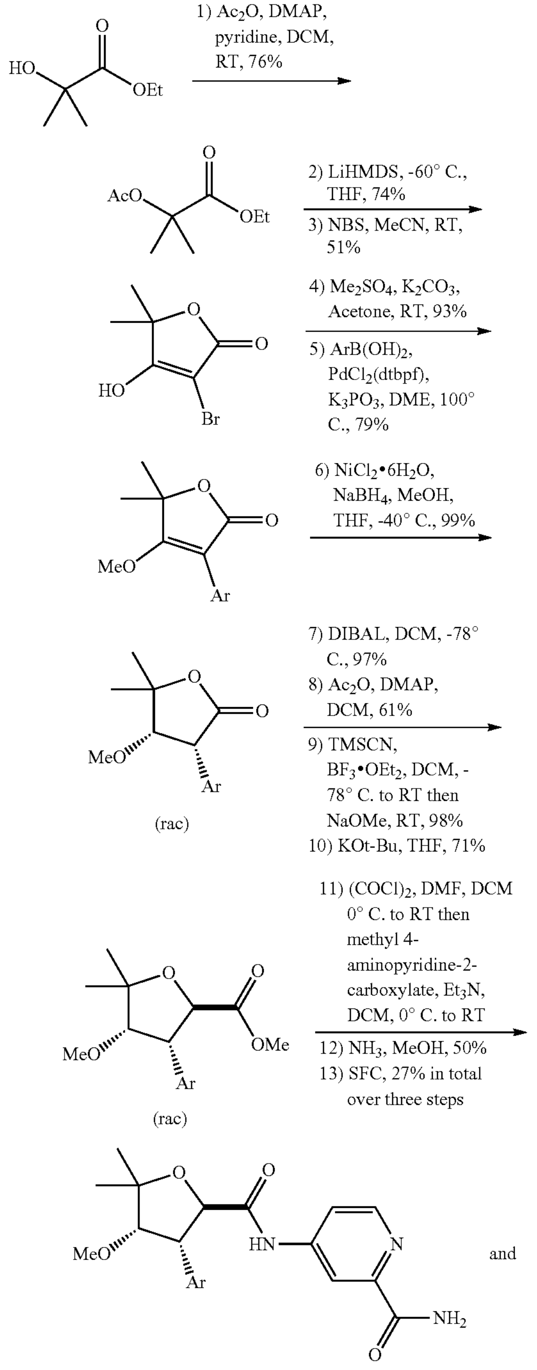

and 18, first eluting isomer

-continued

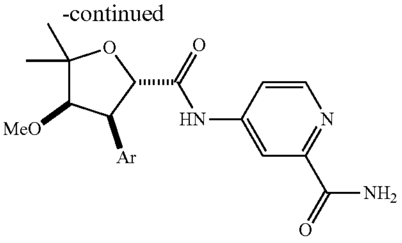

19, second eluting isomer

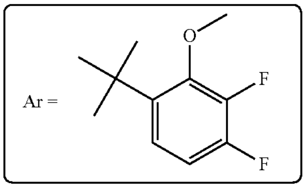

Step 1:

DMAP (3.5 g, 28.649 mmol), pyridine (22.005 g, 22.5 mL, 278.19 mmol) and acetic anhydride (32.460 g, 30 mL, 317.96 mmol) were successively added to a stirred solution of ethyl 2-hydroxy-2-methylpropanoate (25 g, 189.17 mmol) in DCM (125 mL) at ambient temperature. The reaction mixture was stirred for 16 h at ambient temperature. The reaction was quenched by addition of a saturated $Na_2CO_3$ solution (150 mL). The phases were separated and the aqueous layer was extracted with DCM (500 mL). The combined organic extracts were washed with an aqueous $CuSO_4$ solution (200 mL) and water (250 mL), dried ($MgSO_4$), filtered and concentrated in vacuo to give ethyl 2-acetoxy-2-methylpropanoate (25 g, 76%) as light green oil. $^1H$ NMR (400 MHz, DMSO-$d_6$) δ 4.08 (q, J=7.04 Hz, 2H), 2.00 (s, 3H), 1.46 (s, 6H), 1.22-1.15 (t, J=7.00 Hz, 3H) ppm.

Step 2:

A solution of ethyl 2-acetoxy-2-methylpropanoate (20 g, 114.81 mmol) in THF (100 mL) was cooled down to −60° C. A solution of LiHMDS (200 mL of 1 M in THF, 200.00 mmol) was added dropwise over 20 min at such a rate that the mixture was kept below −60° C. The mixture was stirred at 0° C. for 30 min. The reaction was quenched by addition of water (250 mL) and the mixture was allowed to warm up to ambient temperature. The mixture was acidified to pH~1 by addition of a 1N HCl solution. DCM (500 mL) was added and the layers were separated. The organic phase was dried ($Na_2SO_4$), filtered and concentrated in vacuo to give 4-hydroxy-5,5-dimethylfuran-2(5H)-one (12 g, 74%) as an orange solid. $^1H$ NMR (400 MHz, DMSO-$d_6$) δ 12.65 (s, 1H), 4.79 (s, 1H), 1.37 (s, 6H) ppm. ESI-MS m/z calc. 128.0473, found 129.1 $(M+1)^+$; Retention time: 0.70 minutes.

Step 3:

NBS (25 g, 140.46 mmol) was added to a stirred solution of 4-hydroxy-5,5-dimethylfuran-2(5H)-one (12 g, 85.47 mmol) in acetonitrile (480 mL) at ambient temperature. The reaction mixture was stirred for 16 h. The reaction mixture was concentrated in vacuo. Purification by flash chromatography ($SiO_2$, 20% EtOAc in hexanes) gave 3-bromo-4-hydroxy-5,5-dimethylfuran-2(5H)-one (9 g, 51%) as an off-white solid. $^1H$ NMR (400 MHz, Chloroform-d) δ 1.48 (s, 6H) ppm; alcohol OH not observed.

Step 4:

$K_2CO_3$ (18.5 g, 133.86 mmol) and $Me_2SO_4$ (15.295 g, 11.5 mL, 121.26 mmol) were successively added to a stirred solution of 3-bromo-4-hydroxy-5,5-dimethylfuran-2(5H)-one (11 g, 53.13 mmol) in acetone (530 mL). The resultant mixture was stirred at ambient temperature under argon for 16 h. The mixture was partitioned between water (100 mL) and EtOAc (500 mL). The organic layer was collected and concentrated in vacuo. Purification by flash chromatography ($SiO_2$, 4% EtOAc in hexanes) gave 3-bromo-4-methoxy-5,5-dimethylfuran-2(5H)-one (11 g, 93%) as a white solid. $^1$H NMR (400 MHz, DMSO-$d_6$) δ 4.31 (s, 3H), 1.42 (s, 6H) ppm.

Step 5:

$K_3PO_4$ (20 g, 94.22 mmol) was added to a stirred solution of (3,4-difluoro-2-methoxyphenyl)boronic acid (11.9 g, 63.32 mmol) and 3-bromo-4-methoxy-5,5-dimethylfuran-2(5H)-one (7 g, 31.67 mmol) in DME (150 mL). The mixture was degassed with nitrogen gas for 20 min. $PdCl_2$(dtbpf) (2 g, 3.07 mmol) was added and the reaction mixture was heated at 100° C. for 16 h. The mixture was filtered through a pad of celite. The filtrate was partitioned with water (200 mL). The layers were separated and the aqueous phase was extracted with EtOAc (500 mL). The combined organic layers were dried ($MgSO_4$), filtered and concentrated in vacuo. Purification by flash chromatography ($SiO_2$, 0 to 4% EtOAc in hexanes) gave 3-(3,4-difluoro-2-methoxyphenyl)-4-methoxy-5,5-dimethylfuran-2(5H)-one (7.13 g, 79%) as an off-white solid. $^1$H NMR (400 MHz, DMSO-$d_6$) δ 7.24-7.15 (m, 2H), 3.83 (d, J=1.32 Hz, 3H), 3.67 (s, 3H), 1.49 (s, 6H) ppm. ESI-MS m/z calc. 284.086, found 285.1 $(M+1)^+$; Retention time: 2.08 minutes.

Step 6:

Nickel dichloride hexahydrate (3.7 g, 15.57 mmol) and $NaBH_4$ (3 g, 79.30 mmol) were successively added to a stirred solution of 3-(3,4-difluoro-2-methoxyphenyl)-4-methoxy-5,5-dimethylfuran-2(5H)-one (4.4 g, 15.48 mmol) in a mixture of MeOH (175 mL) and THF (35 mL) at −40° C. The resulting mixture was stirred for 5 min before adding additional amounts of both nickel dichloride hexahydrate (3.7 g, 15.57 mmol) and $NaBH_4$ (3 g, 79.30 mmol). Upon reaction completion, the mixture was quenched by addition of a saturated aqueous $NH_4Cl$ solution (50 mL). The layers were separated and the aqueous phase was extracted with DCM (2×50 mL). The combined organic extracts were dried ($MgSO_4$), filtered and concentrated in vacuo to give a mixture of stereoisomers with rac-(3R,4S)-3-(3,4-difluoro-2-methoxyphenyl)-4-methoxy-5,5-dimethyldihydrofuran-2(3H)-one (4.4 g, 99%) as the main diastereoisomer, which was used without further purification in the next step. $^1$H NMR (500 MHz, Chloroform-d) δ 7.04 (ddd, J=9.1, 5.8, 2.3 Hz, 1H), 6.89 (ddd, J=9.6, 8.9, 7.4 Hz, 1H), 4.47 (d, J=5.8 Hz, 1H), 4.04 (d, J=2.6 Hz, 3H), 4.00-3.97 (m, 1H), 2.96 (s, 3H), 1.50 (s, 3H), 1.49 (s, 3H) ppm. ESI-MS m/z calc. 286.10165, found 287.5 $(M+1)^+$; Retention time: 2.79 minutes.

Step 7:

DIBAL (18 mL, 1 M in toluene solution, 18.00 mmol) was added dropwise to a stirred solution of a mixture of stereoisomers of rac-(3R,4S)-3-(3,4-difluoro-2-methoxyphenyl)-4-methoxy-5,5-dimethyldihydrofuran-2(3H)-one (4.4 g, 15.37 mmol) in DCM (60 mL) at −78° C. Upon reaction completion, the mixture was quenched by addition of a saturated aqueous ammonium chloride solution and a Rochelle's salt solution (30% w/w) (30 mL each). The mixture was stirred for 1 h. The layers were separated and the aqueous phase was extracted with DCM (2×30 mL). The combined organic extracts were dried ($MgSO_4$), filtered and concentrated in vacuo to give rac-(3R,4S)-3-(3,4-difluoro-2-methoxyphenyl)-4-methoxy-5,5-dimethyltetrahydrofuran-2-ol (4.3 g, 97%) as a crystalline solid and as a mixture of stereoisomers, which was used without further purification in the next step. ESI-MS m/z calc. 288.1173, found 271.4 $(M-OH)^+$; Retention time: 2.54 minutes.

Step 8:

DMAP (910 mg, 7.45 mmol) and acetic anhydride (5.6 mL, 59.35 mmol) were successively added to a stirred solution of a mixture of stereoisomers of rac-(3R,4S)-3-(3,4-difluoro-2-methoxyphenyl)-4-methoxy-5,5-dimethyltetrahydrofuran-2-ol (4.3 g, 14.92 mmol) in DCM (45 mL) at ambient temperature. The reaction mixture was stirred for 16 h before being quenched by addition of a saturated aqueous sodium bicarbonate solution (30 mL). The mixture was stirred at ambient temperature for 30 min. The layers were separated and the aqueous phase was extracted with DCM (20 mL). The combined organic layers were dried ($MgSO_4$), filtered and concentrated in vacuo. Purification by flash chromatography gave a mixture of stereoisomers of rac-(3R,4S)-3-(3,4-difluoro-2-methoxyphenyl)-4-methoxy-5,5-dimethyltetrahydrofuran-2-yl acetate (3 g, 61%), which was used as such in the next step. ESI-MS m/z calc. 330.12787, found 271.4 $(M-OAc)^+$; Retention time: 3.14 minutes.

Step 9:

TMSCN (3.15 mL, 23.62 mmol) and $BF_3{\cdot}OEt_2$ (3.62 mL of 46.5% w/w, 29.33 mmol) were successively added dropwise to a stirred solution of a mixture of stereoisomers of rac-(3R,4S)-3-(3,4-difluoro-2-methoxyphenyl)-4-methoxy-5,5-dimethyltetrahydrofuran-2-yl acetate (3 g, 9.08 mmol) in DCM (90 mL) at −78° C. The reaction was stirred at −78° C. for 30 min and then warmed up to ambient temperature. The mixture was quenched by addition of a saturated aqueous sodium bicarbonate solution (10 mL). The aqueous layer was separated and extracted with DCM (10 mL). The combined organic extracts were dried ($MgSO_4$), filtered and concentrated in vacuo. The residue was dissolved in EtOAc (30 mL). The solution was dried ($MgSO_4$), filtered concentrated in vacuo. The residue was dissolved in a sodium methoxide solution (27.5 mL of 0.5 M in methanol, 13.75 mmol) and stirred at ambient temperature for 16 h. The reaction was quenched by addition of a saturated aqueous citric acid solution (1 mL). The mixture was concentrated in vacuo and the residue dissolved in EtOAc (10 mL) and brine (30 mL). The organic phase was separated, dried ($MgSO_4$), filtered and concentrated in vacuo to give a mixture of stereoisomers with methyl rac-(2R,3R,4S)-3-(3,4-difluoro-2-methoxyphenyl)-4-methoxy-5,5-dimethyltetrahydrofuran-2-carboxylate (2.95 g, 98%) as the main diastereoisomer. ESI-MS m/z calc. 330.12787, found 330.4 $(M+1)^+$; Retention time: 3.02 minutes.

Step 10:

Potassium tert-butoxide (4 g, 35.65 mmol) was added to a stirred solution of a mixture of stereoisomers of methyl rac-(2R,3R,4S)-3-(3,4-difluoro-2-methoxyphenyl)-4-methoxy-5,5-dimethyltetrahydrofuran-2-carboxylate (2.95 g, 8.93 mmol) in THF (35 mL) at ambient temperature. Upon reaction completion, the mixture was quenched by addition of water (20 mL) and diluted with DCM. The layers were separated and the aqueous phase extracted with DCM (20 mL). The aqueous phase was acidified to pH 0 with 1M HCl and extracted with DCM (2×20 mL). The combined organic extracts were dried ($MgSO_4$), filtered and concentrated in vacuo to give rac-(2R,3R,4S)-3-(3,4-difluoro-2-methoxyphenyl)-4-methoxy-5,5-dimethyltetrahydrofuran-2-carboxylic acid (2 g, 71%), as a mixture of stereoisomers, which was used as is in the next step. ESI-MS m/z calc. 316.11224, found 315.4 $(M-1)^-$; Retention time: 1.68 minutes.

Step 11, 12 and 13:

Oxalyl chloride (60 μL, 0.69 mmol) was added to a stirred solution of a mixture of stereoisomers of rac-(2R,3R,4S)-3-(3,4-difluoro-2-methoxyphenyl)-4-methoxy-5,5-dimethyl-tetrahydrofuran-2-carboxylic acid (100 mg, 0.32 mmol) and DMF (2.5 μL, 0.032 mmol) in DCM (1.2 mL) at 0° C. The reaction mixture was warmed to ambient temperature over 30 min and concentrated in vacuo. The residue, re-dissolved in DCM (600 μL), was added to a stirred solution of methyl 4-aminopyridine-2-carboxylate (60 mg, 0.39 mmol) and $NEt_3$ (60 μL, 0.43 mmol) in DCM (600 μL) at 0° C. The reaction mixture was warmed to ambient temperature over 2 h. The mixture was quenched by addition of a saturated aqueous $NH_4Cl$ solution. The aqueous layer was separated and extracted with DCM (2×5 mL). The combined organic phases were dried ($MgSO_4$), filtered and concentrated in vacuo. Purification by flash chromatography gave a mixture of stereoisomers of methyl rac-4-((2R,3R,4S)-3-(3,4-difluoro-2-methoxyphenyl)-4-methoxy-5,5-dimethyltetrahydrofuran-2-carboxamido)picolinate, which was used directly in the next step. ESI-MS m/z calc. 450.16025, found 451.4 $(M+1)^+$; 449.5 $(M-1)^-$; Retention time: 2.97 minutes.

A mixture of stereoisomers of methyl rac-4-((2R,3R,4S)-3-(3,4-difluoro-2-methoxyphenyl)-4-methoxy-5,5-dimethyltetrahydrofuran-2-carboxamido)picolinate was dissolved in methanolic ammonia (5 mL of 7 M, 35.00 mmol) and stirred at ambient temperature overnight. The reaction mixture was concentrated in vacuo to give a mixture of stereoisomers of rac-4-((2R,3R,4S)-3-(3,4-difluoro-2-methoxyphenyl)-4-methoxy-5,5-dimethyltetrahydrofuran-2-carboxamido)picolinamide.

The enantiomers of rac-4-((2R,3R,4S)-3-(3,4-difluoro-2-methoxyphenyl)-4-methoxy-5,5-dimethyltetrahydrofuran-2-carboxamido)picolinamide were separated by chiral SFC using a Lux i-Cellulose-5 column, 5 m particle size, 25 cm×10 mm from Phenomenex, Inc. on a Minigram SFC instrument from Berger Instruments (25% MeOH, 20 mM $NH_3$, 245 nm, 100 bar):

First Eluting Isomer (rt=4.93 min): rel-4-((2R,3R,4S)-3-(3,4-difluoro-2-methoxyphenyl)-4-methoxy-5,5-dimethyl-tetrahydrofuran-2-carboxamido)picolinamide (18, 10 mg, 13%). $^1H$ NMR (500 MHz, DMSO-$d_6$) δ 10.48 (s, 1H), 8.46 (dd, J=5.5, 0.6 Hz, 1H), 8.29 (dd, J=2.2, 0.6 Hz, 1H), 8.04 (d, J=2.8 Hz, 1H), 7.82 (dd, J=5.5, 2.2 Hz, 1H), 7.59 (d, J=2.9 Hz, 1H), 7.27-7.10 (m, 2H), 4.80 (d, J=10.4 Hz, 1H), 4.21 (dd, J=10.4, 4.9 Hz, 1H), 3.92 (d, J=1.4 Hz, 3H), 3.61 (d, J=5.0 Hz, 1H), 2.97 (s, 3H), 1.38 (s, 3H), 1.33 (s, 3H) ppm. ESI-MS m/z calc. 435.16058, found 436.3 $(M+1)^+$; 434.3 (M−1); Retention time: 2.80 minutes.

Second Eluting Isomer (rt=5.37 min): rel-4-((2S,3S,4R)-3-(3,4-difluoro-2-methoxyphenyl)-4-methoxy-5,5-dimethyltetrahydrofuran-2-carboxamido)picolinamide (19, 10 mg, 14%). $^1H$ NMR (500 MHz, DMSO-$d_6$) δ 10.48 (s, 1H), 8.46 (dd, J=5.5, 0.6 Hz, 1H), 8.28 (dd, J=2.2, 0.6 Hz, 1H), 8.03 (d, J=2.8 Hz, 1H), 7.81 (dd, J=5.5, 2.2 Hz, 1H), 7.63-7.54 (m, 1H), 7.27-7.09 (m, 2H), 4.80 (d, J=10.4 Hz, 1H), 4.21 (dd, J=10.4, 5.0 Hz, 1H), 3.92 (d, J=1.6 Hz, 3H), 3.60 (d, J=5.0 Hz, 1H), 2.97 (s, 3H), 1.38 (s, 3H), 1.32 (s, 3H) ppm. ESI-MS m/z calc. 435.16058, found 436.3 $(M+1)^+$; 434.3 (M−1); Retention time: 2.80 minutes.

The following compounds were made using the method described in Example 3, except that rel-2-(2,2-dimethyl-1,3-dioxolan-4-yl)pyridin-4-amine (Intermediate D, first eluting peak from chiral SFC separation) was used as the coupling partner in the amide coupling Step 11. Step 12 was not required. The chiral SFC separation step 13 was carried out using a Chiralpak IC column, 5 m particle size, 25 cm×20 mm from Daicel on a Prep-100 SFC instrument from Waters (50% MeOH, 20 mM $NH_3$). A final deprotection step was carried out using an excess of TFA in DCM as the solvent:

| Cmpd No. | Compound Name | LC/MS | NMR (shifts in ppm) |
|---|---|---|---|
| 20 | rel-(2R,3R,4S)-3-(3,4-difluoro-2-methoxyphenyl)-N-(2-((R)-1,2-dihydroxyethyl)pyridin-4-yl)-4-methoxy-5,5-dimethyltetrahydrofuran-2-carboxamide (Precursor was the first eluting peak by SFC on Chiralpak IC column, rt = 1.13 min) | ESI-MS m/z calc. 452.1759, found 453.6 $(M + 1)^+$; 451.5 $(M - 1)^-$; Retention time: 2.57 minutes | $^1H$ NMR (500 MHz, DMSO-$d_6$) δ 10.29 (s, 1H), 8.32 (d, J = 5.5 Hz, 1H), 7.73 (d, J = 2.4 Hz, 1H), 7.50 (dd, J = 5.5, 2.2 Hz, 1H), 7.27-7.08 (m, 2H), 5.35 (d, J = 4.7 Hz, 1H), 4.80 (d, J = 10.4 Hz, 1H), 4.70-4.61 (m, 1H), 4.52 (dt, J = 6.9, 4.2 Hz, 1H), 4.20 (dd, J = 10.5, 5.0 Hz, 1H), 3.93 (d, J = 1.6 Hz, 3H), 3.65 (ddd, J = 9.9, 5.9, 3.9 Hz, 1H), 3.61 (d, J = 5.0 Hz, 1H), 3.48-3.39 (m, 1H), 2.97 (s, 3H), 1.38 (s, 3H), 1.32 (s, 3H) ppm. |
| 21 | rel-(2S,3S,4R)-3-(3,4-difluoro-2-methoxyphenyl)-N-(2-((R)-1,2-dihydroxyethyl)pyridin-4-yl)-4-methoxy-5,5-dimethyltetrahydrofuran-2-carboxamide (Precursor was the second eluting peak by SFC on Chiralpak IC column, rt = 1.27 min) | ESI-MS m/z calc. 452.1759, found 453.6 $(M + 1)^+$; 451.5 $(M - 1)^-$; Retention time: 2.57 minutes | $^1H$ NMR (500 MHz, DMSO-$d_6$) δ 10.30 (s, 1H), 8.31 (d, J = 5.5 Hz, 1H), 7.75-7.69 (m, 1H), 7.51 (dd, J = 5.7, 2.0 Hz, 1H), 7.25-7.11 (m, 2H), 5.37 (s, 1H), 4.79 (d, J = 10.4 Hz, 1H), 4.65 (s, 1H), 4.51 (d, J = 9.1 Hz, 1H), 4.20 (dd, J = 10.5, 4.8 Hz, 1H), 3.92 (d, J = 1.6 Hz, 3H), 3.67-3.61 |

-continued

| Cmpd No. | Compound Name | LC/MS | NMR (shifts in ppm) |
|---|---|---|---|
| | | | (m, 1H), 3.60 (d, J = 5.0 Hz, 1H), 3.43 (s, 1H), 2.97 (s, 3H), 1.37 (s, 3H), 1.31 (s, 3H) ppm. |

Figure 2:
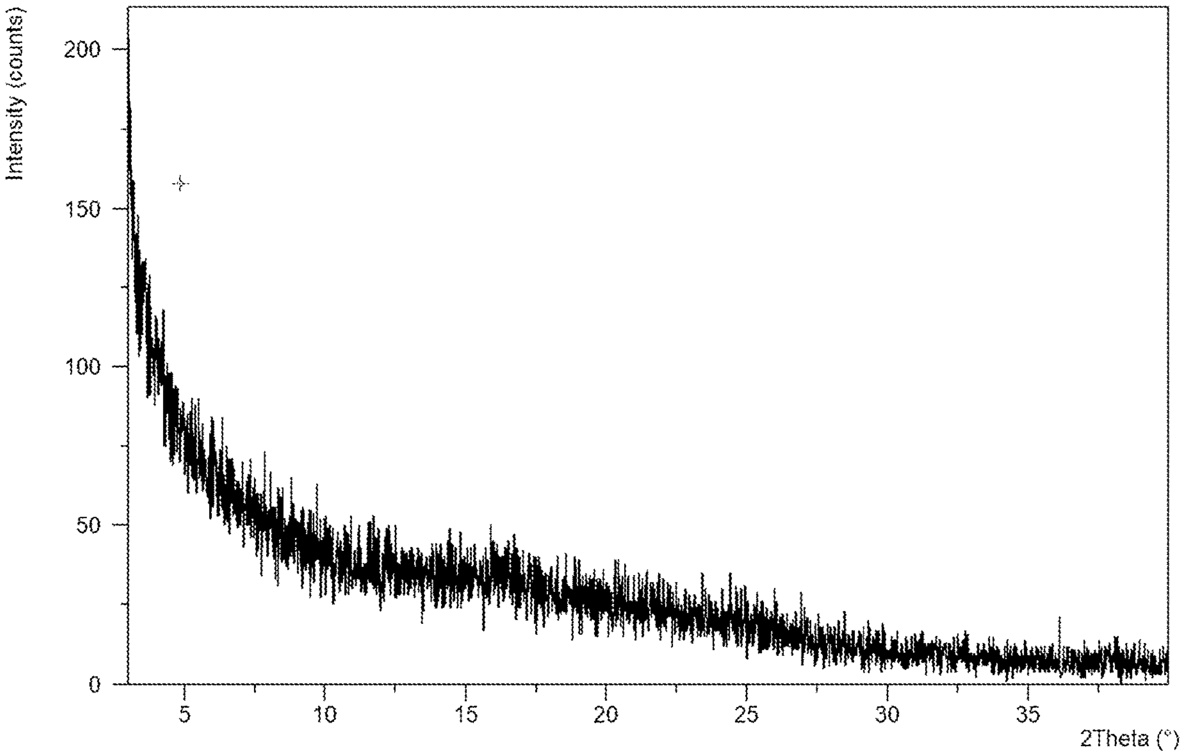
FIG. 2 depicts an XRPD pattern characteristic of amorphous Compound 21.
Figure 3:
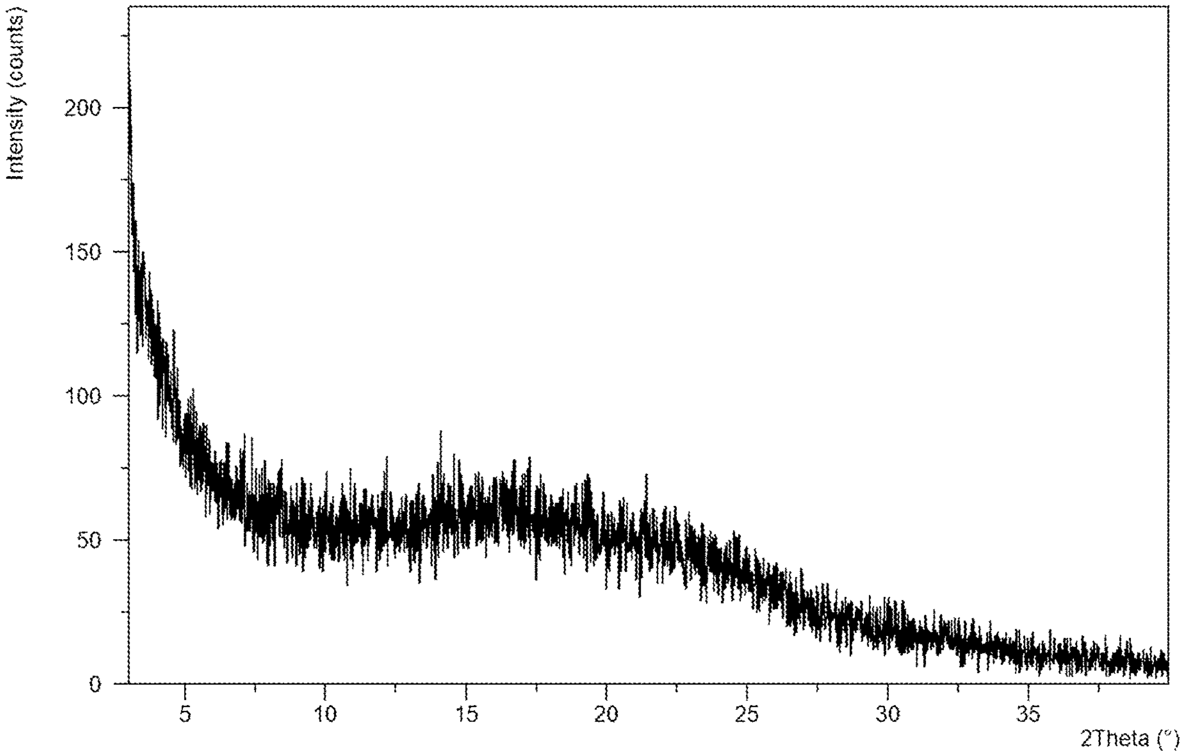
FIG. 3 depicts an XRPD pattern characteristic of amorphous Compound 23.

Compound 21 was analyzed by X-ray powder diffraction and determined to be amorphous (see FIG. 2).

The following compounds were made using the method described in Example 3, except that rel-2-(2,2-dimethyl-1,3-dioxolan-4-yl)pyridin-4-amine (second eluting peak from chiral SFC separation) was used as the coupling partner in the amide coupling Step 11. Step 12 was not required. The chiral SFC separation step 13 was carried out using a Chiralpak ID column, 5 μm particle size, 25 cm×10 mm from Daicel on a Minigram SFC instrument from Berger Instruments (12% MeOH, 20 mM $NH_3$, 245 nm, 100 bar). A final deprotection step was carried out using an excess of TFA in DCM as the solvent:

| Cmpd No. | Compound Name | LC/MS | NMR (shifts in ppm) |
|---|---|---|---|
| 22 | rel-(2R,3R,4S)-3-(3,4-difluoro-2-methoxyphenyl)-N-(2-((S)-1,2-dihydroxyethyl)pyridin-4-yl)-4-methoxy-5,5-dimethyltetrahydrofuran-2-carboxamide (Precursor was the first eluting peak by SFC on Chiralpak ID column, rt = 4.76 min) | ESI-MS m/z calc. 452.1759, found 453.6 $(M + 1)^+$; 451.6 $(M - 1)^-$; Retention time: 2.57 minutes | $^1H$ NMR (500 MHz, DMSO-$d_6$) δ 10.28 (s, 1H), 8.31 (d, J = 5.6 Hz, 1H), 7.72 (d, J = 2.1 Hz, 1H), 7.50 (dd, J = 5.6, 2.1 Hz, 1H), 7.25-7.09 (m, 2H), 5.34 (d, J = 4.7 Hz, 1H), 4.79 (d, J = 10.5 Hz, 1H), 4.64 (t, J = 5.9 Hz, 1H), 4.51 (dt, J = 6.8, 4.3 Hz, 1H), 4.20 (dd, J = 10.5, 4.9 Hz, 1H), 3.92 (d, J = 1.5 Hz, 3H), 3.64 (ddd, J = 10.9, 5.9, 4.0 Hz, 1H), 3.60 (d, J = 4.9 Hz, 1H), 3.46-3.39 (m, 1H), 2.97 (s, 3H), 1.37 (s, 3H), 1.31 (s, 3H) ppm. |
| 23 | rel-(2S,3S,4R)-3-(3,4-difluoro-2-methoxyphenyl)-N-(2-((S)-1,2-dihydroxyethyl)pyridin-4-yl)-4-methoxy-5,5-dimethyltetrahydrofuran-2-carboxamide (Precursor was the second eluting peak by SFC on Chiralpak ID column, rt = 5.60 min) | ESI-MS m/z calc. 452.1759, found 453.6 $(M + 1)^+$; 451.5 $(M - 1)^-$; Retention time: 2.57 minutes | $^1H$ NMR (500 MHz, DMSO-$d_6$) δ 10.29 (s, 1H), 8.32 (d, J = 5.6 Hz, 1H), 7.73 (d, J = 2.2 Hz, 1H), 7.50 (dd, J = 5.6, 2.1 Hz, 1H), 7.26-7.03 (m, 2H), 5.35 (d, J = 4.7 Hz, 1H), 4.80 (d, J = 10.4 Hz, 1H), 4.65 (t, J = 5.9 Hz, 1H), 4.52 (dt, J = 6.8, 4.3 Hz, 1H), 4.20 (dd, J = 10.4, 4.9 Hz, 1H), 3.93 (d, J = 1.5 Hz, 3H), 3.64 (ddd, J = 10.9, 5.9, 4.0 Hz, 1H), 3.61 (d, J = 5.0 Hz, 1H), 3.43 (ddd, J = 11.0, 6.9, 5.8 Hz, 1H), 2.97 (s, 3H), 1.38 (s, 3H), 1.32 (s, 3H) ppm. |

Example 4

4-((2R,3R,4S,5S)-3-(3,4-difluoro-2-methoxyphenyl)-5-isopropyl-4-methoxytetrahydrofuran-2-carboxamido)picolinamide (24)

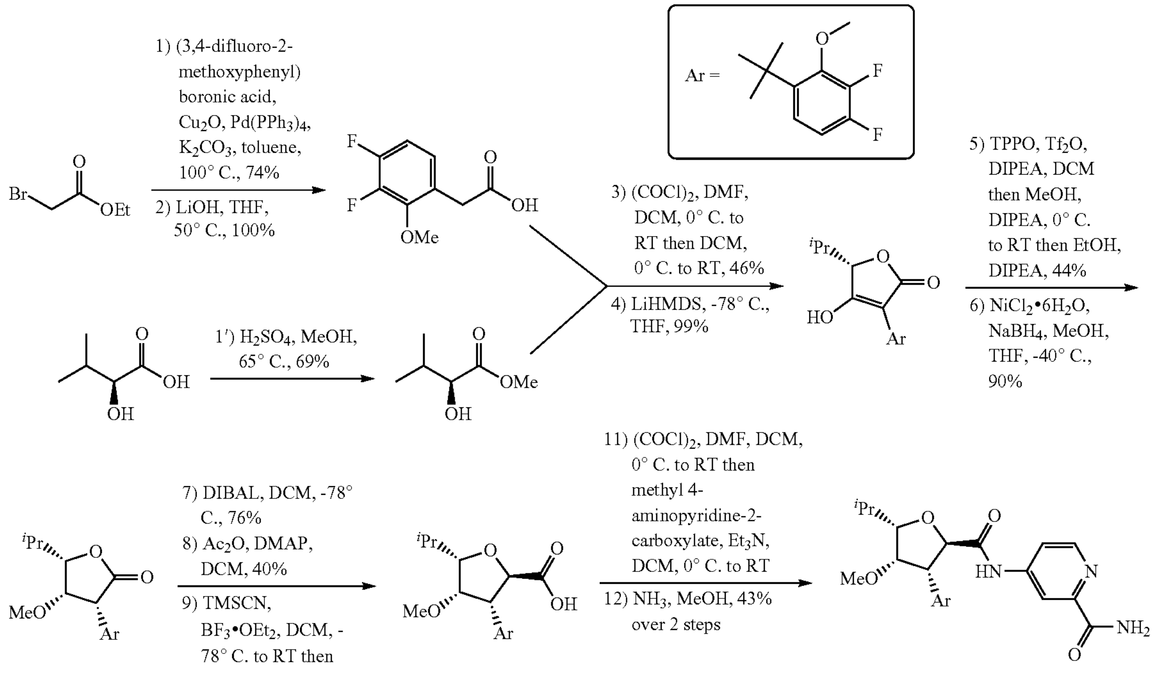

24

Step 1:

A mixture of (3,4-difluoro-2-methoxyphenyl)boronic acid (12.5 g, 66.51 mmol), ethyl 2-bromoacetate (10 g, 58.68 mmol), $K_2CO_3$ (28 g, 200.6 mmol) and $Cu_2O$ (260 mg, 1.763 mmol) in toluene (200 mL) was flushed with nitrogen. $Pd(PPh_3)_4$ (2.2 g, 1.866 mmol) was added, and the reaction mixture was heated to 100° C. for 20 h. The reaction was quenched by addition of water (50 mL). The mixture was diluted with EtOAc (50 mL). The phases were separated. The organic layer was dried ($MgSO_4$), filtered and concentrated in vacuo. Purification by flash chromatography gave ethyl 2-(3,4-difluoro-2-methoxyphenyl)acetate (10 g, 74%) with ~75% purity. ESI-MS m/z calc. 230.07545, found 230.8 $(M+1)^+$; Retention time: 2.89 minutes.

Step 2:

LiOH (20 mL of 2 M, 40.00 mmol) was added at room temperature to a stirred solution of ethyl 2-(3,4-difluoro-2-methoxyphenyl)acetate (4 g, 17.38 mmol) in THF (50 mL). The reaction mixture was stirred at 50° C. Upon reaction completion, the mixture was diluted with DCM (30 mL). The aqueous phase was collected, acidified to pH 0 with 1N HCl and extracted with DCM (2×20 mL). The combined organic extracts were dried ($MgSO_4$) and concentrated in vacuo to give 2-(3,4-difluoro-2-methoxyphenyl)acetic acid (3.5 g, 100%) as a white solid. $^1H$ NMR (500 MHz, Chloroform-d) δ 6.90 (ddd, J=8.7, 5.8, 2.1 Hz, 1H), 6.83 (ddd, J=9.6, 8.7, 7.1 Hz, 1H), 3.99 (d, J=2.4 Hz, 3H), 3.64 (s, 2H) ppm; acid OH not observed. ESI-MS m/z calc. 202.04414, found 200.8 $(M-1)^-$; Retention time: 1.04 minutes.

Step 1':

$H_2SO_4$ (3 mL, 56.28 mmol) was added to a stirred solution of (S)-2-hydroxy-3-methylbutanoic acid (15 g, 127.0 mmol) in MeOH (150 mL). The reaction mixture was heated to reflux for 3 h. The mixture was concentrated in vacuo. The residue was dissolved with $Et_2O$. The mixture was washed with a saturated $NaHCO_3$ solution (100 mL) and brine (100 mL), dried ($MgSO_4$), filtered and concentrated in vacuo to give methyl (S)-2-hydroxy-3-methylbutanoate (11.6 g, 69%). $^1H$ NMR (500 MHz, Chloroform-d) δ 4.05 (d, J=3.6 Hz, 1H), 3.79 (s, 3H), 2.66 (br s, 1H), 2.07 (heptd, J=6.9, 3.6 Hz, 1H), 1.02 (d, J=6.9 Hz, 3H), 0.86 (d, J=6.9 Hz, 3H) ppm.

Step 3:

Oxalyl chloride (3.75 mL, 42.99 mmol) was added dropwise at 0° C. to a stirred solution of 2-(3,4-difluoro-2-methoxyphenyl)acetic acid (3.75 g, 18.55 mmol) and DMF (80 µL, 1.033 mmol) in DCM (80 mL). The reaction mixture was warmed up to ambient temperature and stirred for 1 h. The mixture was concentrated in vacuo. The residue was taken in DCM (10 mL) and added to an ice-cold solution of methyl (S)-2-hydroxy-3-methylbutanoate (4.9 g, 37.08 mmol) in DCM (10 mL). The mixture was allowed to warm to ambient temperature overnight. The reaction was quenched by addition of a saturated $NaHCO_3$ solution (10 mL) and diluted with DCM (10 mL). The aqueous phase was separated and extracted with DCM (10 mL). The combined organic extracts were dried ($MgSO_4$), filtered and concentrated in vacuo. Purification by flash chromatography gave methyl (S)-2-(2-(3,4-difluoro-2-methoxyphenyl)acetoxy)-3- methylbutanoate (2.7 g, 46%). $^1$H NMR (500 MHz, Chloroform-d) δ 6.94 (ddd, J=8.2, 5.7, 2.2 Hz, 1H), 6.86-6.79 (m, 1H), 4.86 (d, J=4.6 Hz, 1H), 3.97 (d, J=2.3 Hz, 2H), 3.73 (s, 3H), 3.71 (s, 3H), 2.22 (pd, J=6.9, 4.6 Hz, 1H), 0.97 (d, J=6.9 Hz, 3H), 0.93 (d, J=6.9 Hz, 3H) ppm.

Step 4:

A solution of methyl (S)-2-(2-(3,4-difluoro-2-methoxyphenyl)acetoxy)-3-methylbutanoate (2.7 g, 8.536 mmol) in THF (75 mL) was added over 30 min to a stirred solution of LiHMDS (22 mL of 1 M in THF, 22.00 mmol) in THF (75 mL) at −78° C. The mixture was stirred at −78° C. for 90 min. The reaction was quenched by pouring the contents of the flask into a 2N HCl solution (30 mL). The layers were separated. The aqueous phase was extracted with EtOAc. The combined organic extracts were dried ($Na_2SO_4$), filtered and concentrated in vacuo to give (S)-3-(3,4-difluoro-2-methoxyphenyl)-4-hydroxy-5-isopropylfuran-2(5H)-one (2.4 g, 99%), which was used in the next step without further purification. ESI-MS m/z calc. 284.08603, found 284.8 $(M+1)^+$; 283.0 $(M-1)^-$; Retention time: 1.20 minutes.

Step 5:

Triflic anhydride (8.5 mL, 1 M solution in DCM, 8.500 mmol) was added dropwise to a stirred solution of TPPO (4.9 g, 17.61 mmol) in DCM (40 mL) at 0° C. After stirring for 15 min, a precipitate had formed. A solution of (S)-3-(3,4-difluoro-2-methoxyphenyl)-4-hydroxy-5-isopropyl-furan-2(5H)-one (2.4 g, 8.443 mmol) and DIPEA (1.5 mL, 8.612 mmol) in DCM (60 mL) was added to the suspension. After the colourless precipitate had dissolved, methanol (750 μL, 18.51 mmol) was added dropwise, followed by DIPEA (1.9 mL, 10.91 mmol). The reaction was warmed up to ambient temperature and stirred for 20 h. The reaction mixture was concentrated in vacuo. Purification by flash chromatography gave (S)-3-(3,4-difluoro-2-methoxyphenyl)-5-isopropyl-4-methoxyfuran-2(5H)-one (1.1 g, 44%). ESI-MS m/z calc. 298.10165, found 298.9 $(M+1)^+$; 296.8 $(M-1)^-$; Retention time: 3.05 minutes.

Step 6:

Nickel dichloride hexahydrate (530 mg, 2.230 mmol) and $NaBH_4$ (420 mg, 11.10 mmol) were successively added to a stirred solution of (S)-3-(3,4-difluoro-2-methoxyphenyl)-5-isopropyl-4-methoxyfuran-2(5H)-one (660 mg, 2.213 mmol) in a mixture of MeOH (25 mL) and THF (5 mL) at −40° C. The procedure was repeated until complete consumption of the starting material. In total, 3 eq. of $NiCl_2 \cdot 6H_2O$ were added. Upon completion, the reaction mixture was quenched by addition of a saturated ammonium chloride solution. The mixture was diluted with DCM and the phases were separated. The organic layer was dried ($MgSO_4$), filtered and concentrated in vacuo to give (3R,4S,5S)-3-(3,4-difluoro-2-methoxyphenyl)-5-isopropyl-4-methoxydihydrofuran-2(3H)-one (600 mg, 90%), which was used in the next step without further purification. $^1$H NMR (500 MHz, Chloroform-d) δ 7.11 (ddd, J=8.4, 5.7, 2.3 Hz, 1H), 6.91 (td, J=9.2, 7.4 Hz, 1H), 4.29 (d, J=4.5 Hz, 1H), 4.04 (d, J=2.6 Hz, 3H), 4.03-3.96 (m, 2H), 2.85 (s, 3H), 2.22 (dq, J=10.0, 6.7 Hz, 1H), 1.14 (d, J=6.7 Hz, 3H), 0.94 (d, J=6.7 Hz, 3H) ppm.

Step 7:

DIBAL (2.4 mL, 1 M solution in toluene, 2.400 mmol) was added dropwise under nitrogen to a stirred solution of (3R,4S,5S)-3-(3,4-difluoro-2-methoxyphenyl)-5-isopropyl-4-methoxydihydrofuran-2(3H)-one (600 mg, 1.998 mmol) in DCM (10 mL) at −78° C. Upon reaction completion, the mixture was quenched by addition of a saturated ammonium chloride solution and a Rochelle's salt solution (30% w/w). The resulting mixture was vigorously stirred at ambient temperature until a clear phase separation was observed. The organic phase was separated, dried ($MgSO_4$), filtered and concentrated in vacuo to give (3R,4S,5S)-3-(3,4-difluoro-2-methoxyphenyl)-5-isopropyl-4-methoxytetrahydrofuran-2-ol (460 mg, 76%), which was used in the next step without further purification. ESI-MS m/z calc. 302.13297, found 285.9 $(M-OH)^+$; Retention time: 2.88 minutes.

Step 8:

Acetic anhydride (500 μL, 5.299 mmol) was added to a stirred solution of (3R,4S,5S)-3-(3,4-difluoro-2-methoxyphenyl)-5-isopropyl-4-methoxytetrahydrofuran-2-ol (400 mg, 1.323 mmol) and DMAP (120 mg, 0.9823 mmol) in DCM (4 mL) under nitrogen at room temperature. Upon reaction completion, the mixture was quenched by addition of a saturated sodium bicarbonate solution (30 mL). The mixture was diluted with DCM (20 mL). The aqueous phase was separated and extracted with DCM (10 mL). The combined organic extracts were dried ($MgSO_4$) and concentrated in vacuo. Purification by flash chromatography gave (3R,4S,5S)-3-(3,4-difluoro-2-methoxyphenyl)-5-isopropyl-4-methoxytetrahydrofuran-2-yl acetate (180 mg, 40%). ESI-MS m/z calc. 344.14352, found 285.9 $(M-OAc)^+$; Retention time: 3.43 minutes.

Step 9:

TMSCN (180 μL, 1.350 mmol) and $BF_3 \cdot OEt_2$ (200 μL, 1.621 mmol) were successively added dropwise to a stirred solution of (3R,4S,5S)-3-(3,4-difluoro-2-methoxyphenyl)-5-isopropyl-4-methoxytetrahydrofuran-2-yl acetate (180 mg, 0.5227 mmol) in DCM (5.5 mL) at −78° C. The mixture was stirred at −78° C. for 30 min and warmed up to ambient temperature. The reaction mixture was quenched by addition of a saturated sodium bicarbonate solution. The aqueous layer was separated and extracted with DCM (3×30 mL). The combined organic extracts were dried ($Na_2SO_4$), filtered and concentrated in vacuo. The residue was taken in DCM and filtered through a pad of Celite. The liquors were concentrated in vacuo. The residue was dissolved in a sodium methoxide solution (1.6 mL, 0.5 M solution in MeOH, 0.8000 mmol) and stirred overnight under nitrogen at ambient temperature. The reaction mixture was quenched by addition of a saturated citric acid solution. The mixture was stirred at room temperature. After complete hydrolysis, the mixture was extracted with DCM (2×30 mL). The organic extracts were combined, dried ($MgSO_4$), filtered and concentrated in vacuo to give methyl (2R,3R,4S,5S)-3-(3,4-difluoro-2-methoxyphenyl)-5-isopropyl-4-methoxytetrahydrofuran-2-carboxylate (150 mg, 83%) which was used without further purification in the next step. ESI-MS m/z calc. 344.14352, found 334.9 $(M+1)^+$; Retention time: 3.35 minutes.

Step 10:

Potassium tert-butoxide (200 mg, 1.782 mmol) was added to a stirred solution of methyl (2R,3R,4S,5S)-3-(3,4-difluoro-2-methoxyphenyl)-5-isopropyl-4-methoxytetrahydrofuran-2-carboxylate (150 mg, 0.4356 mmol) in THF (2 mL) at ambient temperature. The mixture was stirred at ambient temperature. Upon reaction completion, the mixture was quenched by addition of a saturated ammonium chloride solution (3 mL) and diluted with DCM (3 mL). The aqueous layer was separated and extracted with DCM (5 mL). The aqueous extracts were acidified to pH 0 with 1N HCl and extracted with DCM (2×10 mL). The combined organic layers were dried ($MgSO_4$), filtered and concentrated in vacuo to give (2R,3R,4S,5S)-3-(3,4-difluoro-2-methoxyphenyl)-5-isopropyl-4-methoxytetrahydrofuran-2-carboxylic acid (121 mg, 84%). ESI-MS m/z calc. 330.12787, found 330.9 $(M+1)^+$; 329.0 $(M-1)^-$; Retention time: 1.89 minutes.

Step 11 and 12:

Oxalyl chloride (70 μL, 0.802 mmol) was added to a stirred solution of (2R,3R,4S,5S)-3-(3,4-difluoro-2-methoxyphenyl)-5-isopropyl-4-methoxytetrahydrofuran-2-carboxylic acid (120 mg, 0.363 mmol) and DMF (4 μL, 0.052 mmol) in DCM (1.2 mL) cooled down with an ice bath. The mixture was stirred and warmed up to ambient temperature over 30 min. The reaction mixture was concentrated in vacuo. The solids were dissolved in DCM (700 μL) and the new solution was added to an ice cold solution of methyl 4-aminopyridine-2-carboxylate (70 mg, 0.4601 mmol) and $Et_3N$ (75 μL, 0.538 mmol) in DCM (700 μL). The mixture was stirred and warmed up to ambient temperature over 2 h. The reaction mixture was quenched by addition of a saturated ammonium chloride solution (2 mL) and extracted with DCM (2×5 mL). The combined organic extracts were dried ($MgSO_4$), filtered and concentrated in vacuo. Purification by flash chromatography gave methyl 4-((2R,3R,4S,5S)-3-(3,4-difluoro-2-methoxyphenyl)-5-isopropyl-4-methoxytetrahydrofuran-2-carboxamido)picolinate. ESI-MS m/z calc. 464.1759, found 465.1 $(M+1)^+$; 463.1 $(M-1)^-$; Retention time: 3.24 minutes.

Methyl 4-((2R,3R,4S,5S)-3-(3,4-difluoro-2-methoxyphenyl)-5-isopropyl-4-methoxytetrahydrofuran-2-carboxamido)picolinate was dissolved in methanolic ammonia (12 mL, 7 M solution in MeOH, 84.00 mmol) and stirred overnight at ambient temperature. The reaction mixture was concentrated in vacuo to give 4-((2R,3R,4S,5S)-3-(3,4-difluoro-2-methoxyphenyl)-5-isopropyl-4-methoxytetrahydrofuran-2-carboxamido)picolinamide (24, 78 mg, 43%). $^1H$ NMR (500 MHz, DMSO-$d_6$) δ 10.45 (s, 1H), 8.47 (d, J=5.5 Hz, 1H), 8.23 (d, J=2.1 Hz, 1H), 8.07 (d, J=2.8 Hz, 1H), 7.83 (dd, J=5.5, 2.1 Hz, 1H), 7.63 (d, J=2.8 Hz, 1H), 7.30 (ddd, J=8.5, 6.0, 1.9 Hz, 1H), 7.25-7.15 (m, 1H), 4.79 (d, J=10.2 Hz, 1H), 4.05 (dd, J=10.2, 3.8 Hz, 1H), 3.90 (d, J=1.5 Hz, 5H), 2.85 (s, 3H), 2.04-1.90 (m, 1H), 1.03 (d, J=6.6 Hz, 3H), 0.87 (d, J=6.6 Hz, 3H) ppm. ESI-MS m/z calc. 449.17624, found 450.0 $(M+1)^+$; 448.1 $(M-1)^-$; Retention time: 3.07 minutes.

Example 5

4-((2R,3R,4S,5R)-3-(3,4-difluoro-2-methoxyphenyl)-4-ethoxy-5-methyl-5-(trifluoromethyl)tetrahydrofuran-2-carboxamido)picolinamide (25)

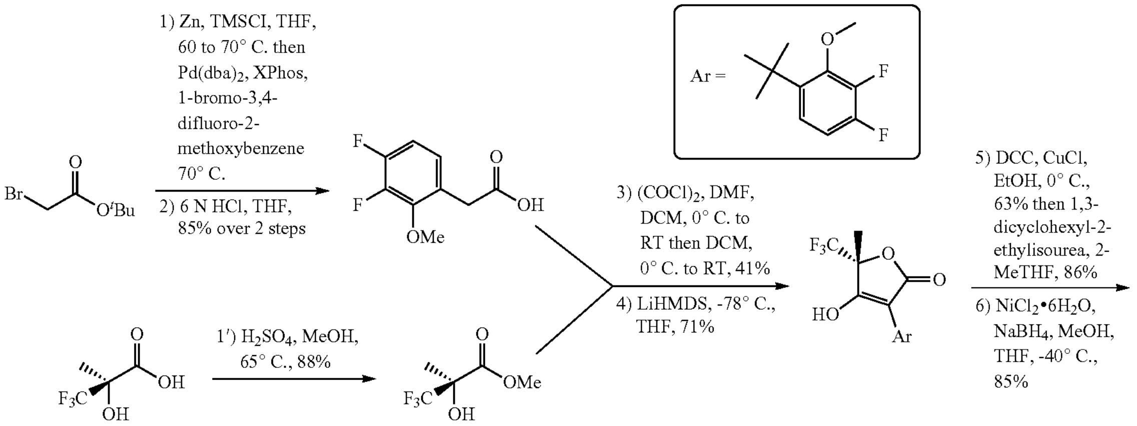

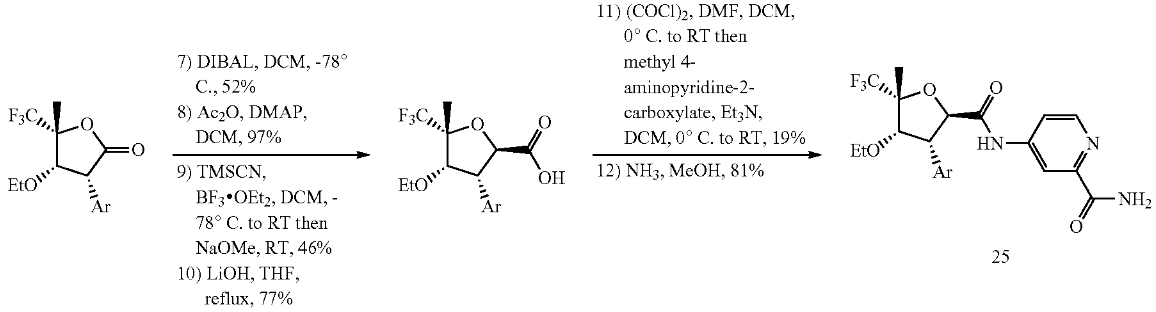

25

Step 1 and 2:

A 1 L three necked round bottom flask, equipped with a condenser and a mechanical stirrer, was charged with tetrahydrofuran (330 mL) and zinc dust (29.5 g, <10 μm, 4.136 mL, 451.14 mmol) under nitrogen. Trimethylsilyl chloride (3.681 g, 4.3 mL, 33.880 mmol) was added in one portion and the reaction mixture was heated to 60° C. for 1 h after which time the zinc powder was mostly in the lower third part of the solution. A solution of tert-butyl 2-bromoacetate (65.68 g, 49.720 mL, 336.73 mmol) in tetrahydrofuran (30 mL) was added dropwise over 20 min, keeping the internal temperature between 65 and 68° C. The temperature was maintained at 67-68° C. for 1 h. The reaction mixture was cooled down to 40° C. and sparged with nitrogen for 10 min. During sparging, the temperature decreased to 31.5° C. The reaction mixture was warmed up to 40° C. and additional degassed tetrahydrofuran (125 mL) was added. $Pd(dba)_2$ (4.57 g, 7.948 mmol) and XPhos (3.8 g, 7.971 mmol) were added. The reaction mixture was heated to 62° C. and a solution of 1-bromo-3,4-difluoro-2-methoxybenzene (50.14 g, 31.337 mL, 224.83 mmol) in tetrahydrofuran (20 mL) was added over 12 min, keeping the internal temperature below 70.5° C. The internal temperature was maintained at 68° C. After 90 min, the reaction mixture was cooled down to 15° C. and stirred overnight.

The reaction mixture was cooled down to 0° C. and a 6N HCl solution (500 mL, 10 vol) was added, keeping the internal temperature below 15° C. The reaction mixture was heated to 55° C. and stirred for 80 min. The reaction mixture was then cooled down to ambient temperature. Heptane (500 mL) was added and the mixture was filtered on a pad of Celite, rinsing with heptane (300 mL, 6 vol) and MTBE (300 mL, 6 vol). The aqueous phase was extracted with MTBE (3×500 mL, 30 vol). The organic extracts were combined, washed with 1M sulfuric acid (500 mL, 10 vol) and brine (250 mL, 5 vol), dried ($Na_2SO_4$), filtered, and concentrated in vacuo. The residue was dissolved in MTBE (300 mL, 6 vol) and washed with 1.5 N sodium hydroxide (400 mL then 150 mL). The basic aqueous layer was cooled down in an ice bath and acidified to pH 1 with 12M hydrochloric acid (150 mL, 3 vol). The aqueous layer was extracted with MTBE (250 mL then 150 mL). The organic extracts were combined, washed with 15% aqueous sodium chloride (200 mL, 4 vol), dried ($Na_2SO_4$) and filtered. Activated charcoal (5 g) was added to the solution which was refluxed for 3 h. The mixture was cooled down to ambient temperature overnight. The mixture was filtered and concentrated in vacuo to give 2-(3,4-difluoro-2-methoxyphenyl)acetic acid (39.55 g, 85%) as a beige solid, which was used in the next step without further purification. $^1H$ NMR (400 MHz, DMSO-$d_6$) δ 12.39 (s, 1H), 7.15-7.03 (m, 2H), 3.87 (d, J=1.7 Hz, 3H), 3.56 (s, 2H) ppm. ESI-MS m/z calc. 202.0442, found 201.1 $(M-1)^-$; Retention time: 2.33 minutes.

Step 1':

(R)-3,3,3-trifluoro-2-hydroxy-2-methylpropanoic acid (30 g, 189.8 mmol) was dissolved in MeOH (50 mL). Sulfuric acid (6 mL, 112.6 mmol) was added via syringe. The mixture was refluxed for 18 h. The MeOH was distilled off. The remaining mixture was poured onto ice-cold water and extracted twice with DCM. The combined organic extracts were washed with a saturated $NaHCO_3$ solution, dried ($MgSO_4$), filtered and concentrated in vacuo to give methyl (R)-3,3,3-trifluoro-2-hydroxy-2-methylpropanoate (28.7 g, 88%). $^1H$ NMR (400 MHz, Chloroform-d) δ 3.91 (s, 3H), 3.78 (s, 1H), 1.64-1.54 (m, 3H) ppm.

Step 3:

Oxalyl chloride (6 mL, 68.78 mmol) was added dropwise at 0° C. to a stirred solution of 2-(3,4-difluoro-2-methoxyphenyl)acetic acid (6 g, 29.68 mmol) and DMF (100 μL, 1.291 mmol) in DCM (100 mL). The solution was warmed to ambient temperature and stirred for 1 h. The mixture was concentrated in vacuo. The residue was taken in DCM (10 mL) and added into an ice-cold solution of methyl (R)-3,3,3-trifluoro-2-hydroxy-2-methylpropanoate (4.4 g, 25.57 mmol) and triethylamine (7.8 mL, 55.96 mmol) in DCM (10 mL). The mixture was allowed to warm to ambient temperature overnight. The reaction was quenched by addition of a saturated solution of ammonium chloride (50 mL) and dilute with DCM (50 mL). The aqueous phase was separated and extracted with DCM (20 mL). The combined organic extracts were dried ($MgSO_4$), filtered and concentrated in vacuo. Purification by flash chromatography gave methyl (R)-2-(2-(3,4-difluoro-2-methoxyphenyl)acetoxy)-3,3,3-trifluoro-2-methylpropanoate (4.3 g, 41%). $^1H$ NMR (500 MHz, Chloroform-d) δ 6.91 (ddd, J=8.1, 5.7, 2.2 Hz, 1H), 6.83 (ddd, J=9.6, 8.7, 7.1 Hz, 1H), 3.98 (d, J=2.5 Hz, 3H), 3.79 (s, 3H), 3.70 (s, 2H), 1.81 (q, J=1.0 Hz, 3H) ppm. ESI-MS m/z calc. 356.06833, Retention time: 3.44 minutes.

Step 4:

A solution of methyl (R)-2-(2-(3,4-difluoro-2-methoxyphenyl)acetoxy)-3,3,3-trifluoro-2-methylpropanoate (1.48 g, 4.154 mmol) in THF (20 mL) was added to a solution of LiHMDS (10 mL of 1 M in THF, 10.00 mmol) in THF (20 mL) at −78° C. The reaction mixture was stirred at −78° C. for 5 h. The solution was quenched by pouring the contents into a 2 M HCl solution. The mixture was diluted with EtOAc. The aqueous layer was separated and extracted twice with EtOAc. The combined organic extracts were dried ($MgSO_4$), filtered and concentrated in vacuo. Purification by flash chromatography ($SiO_2$, 0 to 100% EtOAc in heptane) gave (R)-3-(3,4-difluoro-2-methoxyphenyl)-4-hydroxy-5-methyl-5-(trifluoromethyl)furan-2(5H)-one (950 mg, 71%) as a yellow oil. $^1H$ NMR (400 MHz, Chloroform-d) δ 9.62 (s, 1H), 7.82 (ddd, J=9.2, 5.7, 2.5 Hz, 1H), 7.11 (td, J=9.2, 7.5 Hz, 1H), 4.00 (d, J=1.0 Hz, 3H), 1.79 (q, J=1.1 Hz, 3H) ppm. ESI-MS m/z calc. 324.0421, found 325.1 $(M+1)^+$; 323.1 $(M-1)^-$; Retention time: 0.93 minutes.

Step 5:

Ethanol (4 mL, 68.51 mmol) was added dropwise over 10 min, under nitrogen, to a mixture of DCC (2.71 g, 13.13 mmol) and CuCl (42 mg, 0.4242 mmol) cooled down to 0° C. The reaction mixture was stirred for 1 h at 0° C. The ice bath was removed and the reaction mixture was stirred at ambient temperature for an additional 23 h. The reaction mixture was concentrated in vacuo. Purification by flash chromatography ($SiO_2$, 0 to 100% EtOAc in heptane) gave 1,3-dicyclohexyl-2-ethylisourea (2.1 g, 63%) as a colourless oil. $^1H$ NMR (400 MHz, DMSO-$d_6$) δ 4.78 (d, J=8.2 Hz, 1H), 3.94 (q, J=7.0 Hz, 2H), 3.28-3.17 (m, 1H), 3.00 (tt, J=9.6, 3.8 Hz, 1H), 1.86-1.47 (m, 9H), 1.36-0.98 (m, 11H), 1.12 (t, J=7.0 Hz, 3H) ppm. ESI-MS m/z calc. 252.22017, found 253.3 $(M+1)^+$; Retention time: 0.70 minutes.

A solution of 1,3-dicyclohexyl-2-ethyl-isourea (440 mg, 1.743 mmol) in 2-MeTHF (3 mL) was added to a degassed solution of (R)-3-(3,4-difluoro-2-methoxyphenyl)-4-hydroxy-5-methyl-5-(trifluoromethyl)furan-2(5H)-one (279 mg, 0.861 mmol) in 2-MeTHF (3 mL). The reaction mixture was heated at 85° C. overnight. A white precipitate was filtered off. The mother liquors were concentrated in vacuo. Purification by flash chromatography ($SiO_2$, 0 to 40% EtOAc in heptane) gave (R)-3-(3,4-difluoro-2-methoxyphenyl)-4-ethoxy-5-methyl-5-(trifluoromethyl)furan-2(5H)-one (262 mg, 86%). $^1H$ NMR (400 MHz, Chloroform-d) δ

7.02-6.88 (m, 2H), 4.16-3.89 (m, 2H), 3.92 (d, J=2.0 Hz, 3H), 1.76 (q, J=1.0 Hz, 3H), 1.23 (t, J=7.0 Hz, 3H) ppm. ESI-MS m/z calc. 352.0734, found 353.1 $(M+1)^+$; Retention time: 1.02 minutes.

Step 6:

Nickel dichloride hexahydrate (65 mg, 0.274 mmol) and $NaBH_4$ (53 mg, 1.401 mmol) were successively added to a stirred solution of (R)-3-(3,4-difluoro-2-methoxyphenyl)-4-ethoxy-5-methyl-5-(trifluoromethyl)furan-2(5H)-one (70 mg, 0.199 mmol) in a mixture of MeOH (2.5 mL) and THF (500 μL) at −40° C. The resulting mixture was stirred for 15 min at −40° C. Further quantities of both $NiCl_2 \cdot 6H_2O$ and $NaBH_4$ were added until the reaction reached ~85% conversion as indicated by $^{19}F$ NMR. The reaction mixture was quenched by addition of a saturated $NH_4Cl$ solution. The mixture was diluted with EtOAc and the phases were separated. The aqueous phase was extracted twice with EtOAc. The organic extracts were combined, dried ($MgSO_4$), filtered and concentrated in vacuo to give a mixture of stereoisomers with (3R,4S,5R)-3-(3,4-difluoro-2-methoxyphenyl)-4-ethoxy-5-methyl-5-(trifluoromethyl) dihydrofuran-2(3H)-one (60 mg, 85%) as the main diastereoisomer. $^1H$ NMR (400 MHz, Chloroform-d) δ 7.07-7.01 (m, 1H), 6.97-6.88 (m, 1H), 4.54-4.38 (m, 1H), 4.07 (d, J=6.1 Hz, 1H), 4.06 (d, J=2.9 Hz, 3H), 3.35-3.24 (m, 1H), 2.95-2.78 (m, 1H), 1.65 (q, J=1.2 Hz, 3H), 0.83 (t, J=7.0 Hz, 3H) ppm. ESI-MS m/z calc. 354.08905, found 354.1 $(M+1)^+$; Retention time: 1.02 minutes.

Step 7:

DIBAL (900 μL, 1 M in toluene solution, 0.900 mmol) was added dropwise to a stirred solution of a mixture of stereoisomers of (3R,4S,5R)-3-(3,4-difluoro-2-methoxyphenyl)-4-ethoxy-5-methyl-5-(trifluoromethyl)dihydrofuran-2(3H)-one (260 mg, 0.734 mmol) in DCM (9 mL) at −78° C. The reaction mixture was stirred at −78° C. for 2 h. The mixture was quenched by addition of a saturated ammonium chloride solution and a Rochelle's salt solution (30% w/w) (3 mL each). The mixture was diluted with DCM. The aqueous phase was separated and extracted with EtOAc (2×20 mL). The combined organic extracts were dried ($MgSO_4$), filtered and concentrated in vacuo. Purification by flash chromatography ($SiO_2$, 0 to 30% EtOAc in heptane) gave a mixture of stereoisomers with (3R,4S,5R)-3-(3,4-difluoro-2-methoxyphenyl)-4-ethoxy-5-methyl-5-(trifluoromethyl)tetrahydrofuran-2-ol (135 mg, 52%) as the main diastereoisomer. 1H NMR (400 MHz, Chloroform-d) δ 7.12 (ddd, J=8.5, 5.7, 2.3 Hz, 1H), 6.93-6.84 (m, 1H), 5.86 (dd, J=7.8, 5.4 Hz, 1H), 4.04 (t, J=2.5 Hz, 1H), 4.01 (d, J=2.2 Hz, 3H), 3.73 (dd, J=7.9, 5.7 Hz, 1H), 3.34-3.19 (m, 1H), 3.07 (d, J=5.5 Hz, 1H), 2.97-2.86 (m, 1H), 1.59 (q, J=1.1 Hz, 3H), 0.87 (t, J=7.0 Hz, 3H) ppm. ESI-MS m/z calc. 356.1047, found 309.1 $(M\text{-OH-Et})^+$; Retention time: 0.96 minutes.

Step 8:

DMAP (61 mg, 0.499 mmol) and acetic anhydride (155 μL, 1.643 mmol) were successively added to a stirred solution of a mixture of stereoisomers of (3R,4S,5R)-3-(3,4-difluoro-2-methoxyphenyl)-4-ethoxy-5-methyl-5-(trifluoromethyl)tetrahydrofuran-2-ol (135 mg, 0.379 mmol) in DCM (2 mL) at ambient temperature. The reaction mixture was stirred at ambient temperature overnight. Upon complete conversion, the reaction was quenched by addition of a saturated sodium bicarbonate solution. The aqueous phase was separated and extracted twice with ethyl acetate. The combined organic extracts were washed with a dilute HCl solution and brine, dried ($MgSO_4$), filtered and concentrated in vacuo to give a mixture of stereoisomers of (3R,4S,5R)-3-(3,4-difluoro-2-methoxyphenyl)-4-ethoxy-5-methyl-5-(trifluoromethyl)tetrahydrofuran-2-yl acetate (146 mg, 97%). ESI-MS m/z calc. 398.11526, found 310.1 $(M\text{-OAc-Et})^+$; Retention time: 1.06 minutes.

Step 9:

TMSCN (154 mg, 1.552 mmol) and $BF_3 \cdot OEt_2$ (120 μL, 0.972 mmol) were successively added dropwise to a stirred solution of a mixture of stereoisomers of (3R,4S,5R)-3-(3,4-difluoro-2-methoxyphenyl)-4-ethoxy-5-methyl-5-(trifluoromethyl)tetrahydrofuran-2-yl acetate (150 mg, 0.377 mmol) in DCM (4.5 mL) at −78° C. The mixture was stirred at −78° C. for 15 min and then warmed up to ambient temperature. The mixture was stirred at ambient temperature for 30 min. The mixture was quenched by addition of a 2M sodium carbonate solution (10 mL). The aqueous phase was separated and extracted with DCM (3×−5 mL). The combined organic extracts were dried ($MgSO_4$), filtered and concentrated in vacuo. The residue was dissolved in a sodium methoxide solution (7.5 mL of 0.5 M in methanol, 3.750 mmol) and stirred at ambient temperature for 2 h. The reaction was quenched by addition of a saturated $NH_4Cl$ solution. The mixture was diluted with EtOAc and water. The aqueous layer was separated and extracted twice with EtOAc. The combined organic extracts were dried ($MgSO_4$), filtered and concentrated in vacuo. Purification by flash chromatography ($SiO_2$, 0 to 50% EtOAc in heptane) gave methyl (2R,3R,4S,5R)-3-(3,4-difluoro-2-methoxyphenyl)-4-ethoxy-5-methyl-5-(trifluoromethyl)tetrahydrofuran-2-carbimidate (69 mg, 46%) as the main diastereoisomer. $^1H$ NMR (400 MHz, Chloroform-d) δ 7.72 (s, 1H), 7.18 (ddd, J=8.5, 5.7, 2.3 Hz, 1H), 6.88 (ddd, J=9.7, 9.0, 7.5 Hz, 1H), 4.82 (d, J=11.4 Hz, 1H), 3.94 (d, J=2.2 Hz, 3H), 3.83 (d, J=5.1 Hz, 1H), 3.75 (dd, J=11.4, 5.0 Hz, 1H), 3.60 (s, 3H), 3.24 (dq, J=8.9, 6.9 Hz, 1H), 2.82 (dq, J=8.9, 6.9 Hz, 1H), 1.54 (q, J=1.1 Hz, 3H), 0.87 (t, J=6.9 Hz, 3H) ppm. ESI-MS m/z calc. 397.13126, found 398.2 $(M+1)^+$; Retention time: 0.96 minutes.

Step 10:

LiOH (1000 μL of 2 M aqueous solution, 2.000 mmol) was added to a solution of methyl (2R,3R,4S,5R)-3-(3,4-difluoro-2-methoxyphenyl)-4-ethoxy-5-methyl-5-(trifluoromethyl)tetrahydrofuran-2-carbimidate (55 mg, 0.138 mmol) in THF (3 mL). The reaction mixture was stirred at 70° C. for 2 h. An additional amount of a 2M LiOH solution (1 ml) was added and reaction mixture was stirred at 80° C. over the weekend. A further 1 ml of 2 M LiOH was added and reaction was heated at 100° C. for 5 h. The mixture was acidified with a 1 M HCl solution. The resulting solution was partitioned between water and EtOAc. The aqueous layer was separated and extracted twice with EtOAc. The combined organic extracts were dried ($MgSO_4$) and concentrated in vacuo to give (2R,3R,4S,5R)-3-(3,4-difluoro-2-methoxyphenyl)-4-ethoxy-5-methyl-5-(trifluoromethyl)tetrahydrofuran-2-carboxylic acid (41 mg, 77%) as a yellow oil and as the main diastereoisomer. $^1H$ NMR (400 MHz, Chloroform-d) δ 7.17 (ddd, J=8.3, 5.6, 2.3 Hz, 1H), 6.89 (td, J=9.3, 7.4 Hz, 1H), 5.00 (d, J=11.6 Hz, 1H), 3.99 (d, J=2.4 Hz, 3H), 4.03-3.94 (m, 1H), 3.90 (d, J=5.0 Hz, 1H), 3.28 (dq, J=8.9, 6.9 Hz, 1H), 2.92-2.81 (m, 1H), 1.58 (q, J=1.1 Hz, 3H), 0.87 (t, J=7.0 Hz, 3H) ppm. ESI-MS m/z calc. 384.0996, found 383.2 $(M-1)^-$; Retention time: 0.58 minutes.

Step 11:

Oxalyl chloride (15 μL, 0.172 mmol) was added to a stirred solution of (2R,3R,4S,5R)-3-(3,4-difluoro-2-methoxyphenyl)-4-ethoxy-5-methyl-5-(trifluoromethyl)tetrahydrofuran-2-carboxylic acid (40 mg, 0.104 mmol) and DMF (10 μL, 0.129 mmol) in DCM (1000 μL) at 0° C. The reaction mixture was warmed to ambient temperature and stirred for 90 min. The mixture was concentrated in vacuo. The residue was dissolved in DCM (1000 μL). Methyl 4-aminopyridine-2-carboxylate (21.2 mg, 0.139 mmol) and $Et_3N$ (25 μL, 0.179 mmol) were sequentially added to the reaction mixture. The reaction was stirred for 2 h before being quenched by addition of MeOH. The mixture was concentrated in vacuo. Purification by flash chromatography (4 g $SiO_2$, 0 to 100% EtOAc in heptane) gave methyl 4-((2R,3R,4S,5R)-3-(3,4-difluoro-2-methoxyphenyl)-4-ethoxy-5-methyl-5-(trifluoromethyl)tetrahydrofuran-2-carboxamido)picolinate (10 mg, 19%) as the main diastereoisomer. ESI-MS m/z calc. 518.14764, found 519.2 $(M+1)^+$; 517.2 $(M-1)^-$; Retention time: 0.96 minutes.

Step 12:

Methyl 4-((2R,3R,4S,5R)-3-(3,4-difluoro-2-methoxyphenyl)-4-ethoxy-5-methyl-5-(trifluoromethyl)tetrahydrofuran-2-carboxamido)picolinate (10 mg, 0.019 mmol) was dissolved in methanolic ammonia (1 mL of 7 M solution in MeOH, 7.000 mmol) and stirred at ambient temperature overnight. The reaction mixture was concentrated in vacuo. Purification by reversed phase HPLC using a X-bridge C18 column (150×19 mm, 5 m particle size) from Waters (MeCN in in $H_2O$ with 0.1% ammonium hydroxide, 19 ml/min plus 1 ml/min MeCN at column dilution injection) gave 4-((2R,3R,4S,5R)-3-(3,4-difluoro-2-methoxyphenyl)-4-ethoxy-5-methyl-5-(trifluoromethyl)tetrahydrofuran-2-carboxamido) picolinamide (25, 8 mg, 81%). $^1H$ NMR (400 MHz, Methanol-$d_4$) δ 8.47 (dd, J=5.5, 0.6 Hz, 1H), 8.23 (dd, J=2.1, 0.7 Hz, 1H), 7.87 (dd, J=5.5, 2.2 Hz, 1H), 7.29 (ddd, J=8.5, 5.7, 2.3 Hz, 1H), 7.01 (ddd, J=9.9, 8.9, 7.6 Hz, 1H), 5.06 (d, J=11.3 Hz, 1H), 4.19 (dd, J=11.3, 5.0 Hz, 1H), 4.07 (d, J=5.1 Hz, 1H), 3.98 (d, J=1.9 Hz, 3H), 3.38-3.33 (m, 1H), 2.97-2.85 (m, 1H), 1.61 (d, J=1.1 Hz, 3H), 0.88 (t, J=7.0 Hz, 3H) ppm; amides NH and $NH_2$ not observed. ESI-MS m/z calc. 503.14795, found 504.2 $(M+1)^+$; 502.2 $(M-1)^-$; Retention time: 3.23 minutes.

Intermediate A

4-Fluoro-2-methoxy-3-methylphenyl)boronic acid

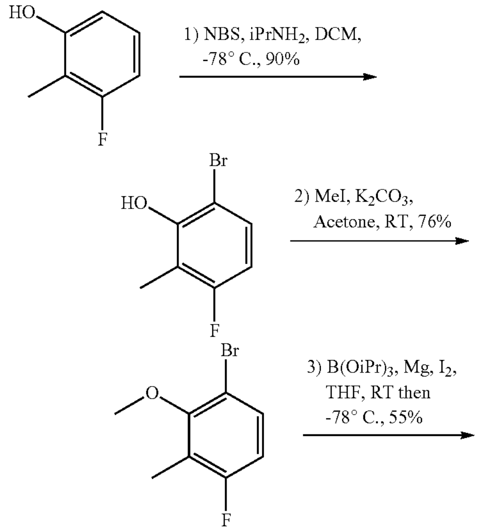

-continued

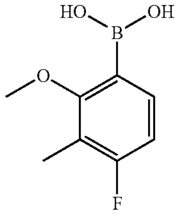

A

Step 1:

Isopropylamine (23.460 g, 34.5 mL, 396.89 mmol) was slowly added to a stirred solution of 3-fluoro-2-methylphenol (50 g, 396.42 mmol) in DCM (2.5 L). The reaction mixture was cooled to −78° C. NBS (70 g, 393.29 mmol) was added portionwise over 2 h 10 min and the mixture was stirred for a further 30 min. The mixture was warmed up to 25° C. 2N HCl (500 ml) was added and the mixture was stirred for 15 min. The organic layer was separated and concentrated in vacuo, keeping the water bath at 15° C. Hexane (500 ml) was added to the residue and the mixture was stirred for 10 min. The mixture was filtered and the liquors were concentrated in vacuo, keeping the water bath at 15° C. to give 6-bromo-3-fluoro-2-methylphenol (73 g, 90%) as a light brown oil. $^1H$ NMR (400 MHz, Chloroform-d) δ 7.24-7.21 (m, 1H), 6.55 (t, J=8.8 Hz, 1H), 5.61 (s, 1H), 2.20 (s, 3H) ppm.

Step 2:

To a stirred solution of 6-bromo-3-fluoro-2-methylphenol (40 g, 195.10 mmol) in acetone (400 mL) at ambient temperature was added potassium carbonate (135 g, 976.80 mmol). The reaction mixture was stirred for 10 min at 25° C. Methyl iodide (39 g, 17.105 mL, 274.77 mmol) was added dropwise over 10 min and the mixture was stirred for 16 h at 25° C. The reaction mixture was filtered and the solid residues washed with acetone (50 ml). The mother liquors were concentrated at 15° C. under reduced pressure. Hexane (200 ml) was added and the mixture was stirred for 15 min. The solid was collected and washed with hexane (8 ml). The mother liquors were concentrated under reduced pressure at 15° C. Purification by distillation (520 mm Hg, 192-196° C.) gave 1-bromo-4-fluoro-2-methoxy-3-methylbenzene (32.4 g, 76%). $^1H$ NMR (400 MHz, Chloroform-d) δ 7.33-7.30 (m, 1H), 6.72 (t, J=8.7 Hz, 1H), 3.80 (s, 3H), 2.23 (s, 3H) ppm.

Step 3:

Iodine (50 mg, 0.1970 mmol) was added at 25° C. to a stirred mixture of Mg turnings (5 g, 205.72 mmol) in THF (50 ml). The mixture was stirred until the reaction turned into a clear pale yellow colour. 1-bromo-4-fluoro-2-methoxy-3-methylbenzene (2.5 g, 11.4 mmol) was added dropwise at ambient temperature. When reaction initiation was observed, the remaining solution of 1-bromo-4-fluoro-2-methoxy-3-methylbenzene (22.5 g, 102.71 mmol) in THF (200 ml) was added dropwise. The mixture was stirred for 40 min. The reaction mixture was cooled down to −78° C. and triisopropylborate (64.385 g, 79 mL, 342.34 mmol) was added dropwise. The mixture was warmed up to ambient temperature and stirred for 16 h. The reaction was quenched by addition of 2N HCl (25 ml) and stirred for 15 min. The mixture was diluted with water (125 ml) and extracted with ethyl acetate (2×250 ml). The organic layer was separated, washed with water (250 ml), dried ($Na_2SO_4$) and concentrated in vacuo. Hexane (2.5 ml) was added to the residue at 0° C. and the mixture was stirred for 5 min. The resulting solid was filtered, washed with 10 ml of chilled hexane and dried to give (4-fluoro-2-methoxy-3-methylphenyl)boronic acid (11.5 g, 55%). $^1$H NMR (400 MHz, DMSO-$d_6$) δ 7.96 (br s, 2H), 7.32 (t, J=8.0 Hz, 1H), 6.88 (t, J=8.7 Hz, 1H), 3.75 (s, 3H), 2.11 (s, 3H) ppm.

Intermediates B and C (S)-6-(2,2-dimethyl-1,3-dioxolan-4-yl)pyridin-3-amine and (R)-6-(2,2-dimethyl-1,3-dioxolan-4-yl)pyridin-3-amine

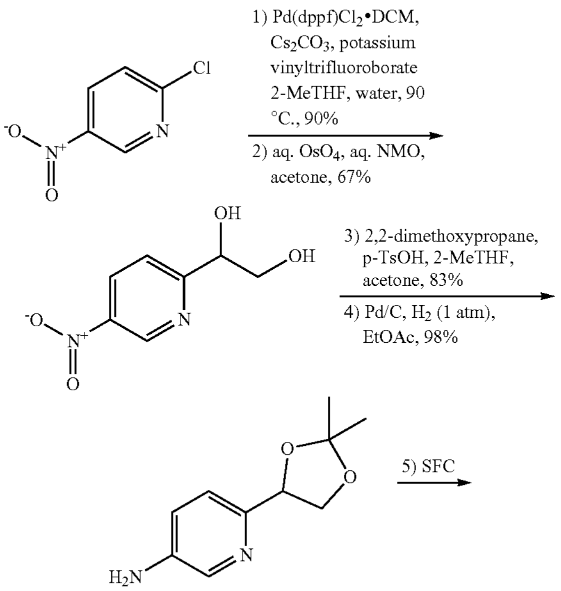

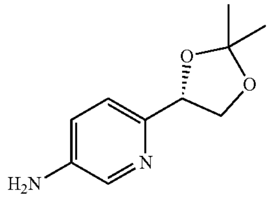

and

B, first eluting isomer

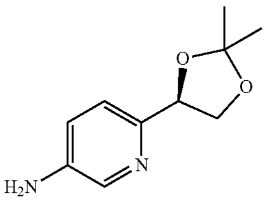

C, first eluting isomer

Step 1:

$Cs_2CO_3$ (100 g, 306.92 mmol) was added to a stirred solution of 2-chloro-5-nitro-pyridine (25 g, 157.69 mmol) and potassium vinyltrifluoroborate (25 g, 186.64 mmol) in a mixture of 2-MeTHF (250 mL) and water (25 mL). The mixture was degassed for 5 min with argon. Pd(dppf) $Cl_2$·DCM (6.25 g, 7.65 mmol) was added and the reaction mixture was degassed again with argon. The reaction mixture was stirred for 6 h at 90° C. The mixture was concentrated in vacuo and partitioned between ethyl acetate (125 mL) and water (40 mL). The organic layer was separated, dried ($MgSO_4$), filtered and concentrated in vacuo. Purification by silica gel chromatography ($SiO_2$, 5 to 20% ethyl acetate in hexanes) gave 5-nitro-2-vinylpyridine (22 g, 90%) as a light brown solid. $^1$H NMR (400 MHz, Chloroform-d) δ 9.38 (s, 1H), 8.42 (dd, J=2.1, 8.5 Hz, 1H), 7.46 (d, J=8.8 Hz, 1H), 6.93-6.86 (m, 1H), 6.44 (d, J=17.36 Hz, 1H), 5.74 (d, J=10.8 Hz, 1H) ppm. ESI-MS m/z calc. 150.0429, found 151.0 $(M+1)^+$; Retention time: 1.59 minutes.

Step 2:

NMO (104 mL of 50% w/v aqueous solution, 443.89 mmol) and $OSO_4$ (19 mL of 4% w/v aqueous solution, 2.989 mmol) were added to a stirred solution of 5-nitro-2-vinylpyridine (22 g, 146.53 mmol) in acetone (250 mL). The reaction mixture was stirred for 3 h at ambient temperature. The acetone was removed in vacuo and the mixture was partitioned with ethyl acetate (150 mL). The organic layer was separated, dried ($MgSO_4$), filtered and concentrated in vacuo. Purification by silica gel chromatography ($SiO_2$, 20 to 80% ethyl acetate in hexanes) gave rac-1-(5-nitropyridin-2-yl)ethane-1,2-diol (18 g, 67%) as an off-white solid. $^1$H NMR (400 MHz, DMSO-$d_6$) δ 9.29 (br s, 1H), 8.60-8.57 (m, 1H), 7.77 (d, J=8 Hz, 1H), 5.77 (d, J=8 Hz, 1H), 4.80 (t, J=5.6 Hz, 1H), 4.73-4.71 (m, 1H), 3.75-3.73 (m, 1H), 3.59-3.56 (m, 1H) ppm. ESI-MS m/z calc. 184.0484, found 185.1 $(M+1)^+$; Retention time: 1.46 minutes.

Step 3:

p-TsOH (30 mg, 0.028 mL, 0.174 mmol) and 2,2-dimethoxypropane (338.80 mg, 0.4 mL, 3.253 mmol) were added to a stirred solution of rac-1-(5-nitropyridin-2-yl)ethane-1,2-diol (295 mg, 1.602 mmol) in a mixture of 2-MeTHF (5 mL) and acetone (5 mL). The reaction mixture was stirred at ambient temperature for 16 h. The reaction mixture was quenched with a solution of $NaHCO_3$ (7 mL). The mixture was concentrated in vacuo and ethyl acetate (50 mL) was added. The mixture was dried ($MgSO_4$), filtered and concentrated in vacuo. Purification by silica gel chromatography ($SiO_2$, 5 to 10% ethyl acetate in hexanes) gave rac-2-(2,2-dimethyl-1,3-dioxolan-4-yl)-5-nitropyridine (300 mg, 83%) as an off-white solid. $^1$H NMR (400 MHz, DMSO-$d_6$) δ 9.33 (br s, 1H), 8.63 (dd, J=2.4, 8.8 Hz, 1H), 7.76 (d, J=8 Hz, 1H), 5.27 (t, J=6.4 Hz, 1H), 4.45 (t, J=8 Hz, 1H), 3.93-3.89 (m, 1H), 1.46 (s, 3H), 1.43 (s, 3H) ppm. ESI-MS m/z calc. 224.0797, found 225.3 $(M+1)^+$; Retention time: 3.24 minutes.

Step 4:

Pd/C (10 wt % loading, wet, Degussa, 285 mg, 0.268 mmol) was added to a solution of rac-2-(2,2-dimethyl-1,3-dioxolan-4-yl)-5-nitropyridine (2 g, 8.920 mmol) in ethyl acetate (60 mL). The reaction mixture was degassed for 5 min with argon and stirred under a balloon atmosphere of hydrogen for 6 h. The reaction mixture was filtered through a pad of celite. The filtrates were concentrated in vacuo to give rac-6-(2,2-dimethyl-1,3-dioxolan-4-yl)pyridin-3-amine (1.7 g, 98%) as a light yellow gum. $^1$H NMR (400 MHz, DMSO-$d_6$) δ 7.86 (d, J=2 Hz, 1H), 7.12 (d, J=8.4 Hz, 1H), 6.92 (dd, J=2.4, 8.4 Hz, 1H), 5.30 (s, 2H), 4.92 (t, J=6.8 Hz, 1H), 4.20 (t, J=6.4 Hz, 1H), 3.78 (t, J=7.6 Hz, 1H), 1.39 (s, 3H), 1.35 (s, 3H) ppm. ESI-MS m/z calc. 194.1055, found 195.2 $(M+1)^+$; Retention time: 1.41 minutes.

Step 5:

The enantiomers of rac-6-(2,2-dimethyl-1,3-dioxolan-4-yl)pyridin-3-amine (9 g, 46.34 mmol) were separated by using a Chiralpak IB column, 5 m particle size, 25 cm×20 mm from Daicel on a Prep-100 SFC instrument from Waters:

First Eluting Isomer (rt=0.90 min): (S)-6-(2,2-dimethyl-1,3-dioxolan-4-yl)pyridin-3-amine (4.4 g, 49%). $^1$H NMR (400 MHz, DMSO-$d_6$) δ 7.86 (dd, J=2.8, 0.7 Hz, 1H), 7.12 (d, J=8.3 Hz, 1H), 6.92 (dd, J=8.3, 2.8 Hz, 1H), 5.29 (s, 2H), 4.92 (dd, J=7.4, 6.4 Hz, 1H), 4.21 (dd, J=8.0, 6.4 Hz, 1H), 3.79 (dd, J=8.0, 7.4 Hz, 1H), 1.40 (d, J=0.7 Hz, 3H), 1.36 (d, J=0.7 Hz, 3H) ppm. ESI-MS m/z calc. 194.10553, found 195.2 $(M+1)^+$; Retention time: 0.43 minutes.

Second Eluting Isomer (rt=1.09 min): (R)-6-(2,2-dimethyl-1,3-dioxolan-4-yl)pyridin-3-amine (4.6 g, 51%). $^1H$ NMR (400 MHz, DMSO-$d_6$) δ 7.86 (dd, J=2.8, 0.7 Hz, 1H), 7.12 (d, J=8.3 Hz, 1H), 6.92 (dd, J=8.3, 2.7 Hz, 1H), 5.29 (s, 2H), 4.97-4.88 (m, 1H), 4.21 (dd, J=8.0, 6.4 Hz, 1H), 3.79 (dd, J=8.0, 7.4 Hz, 1H), 1.40 (d, J=0.7 Hz, 3H), 1.36 (d, J=0.7 Hz, 3H) ppm. ESI-MS m/z calc. 194.10553, found 195.2 $(M+1)^+$; Retention time: 0.43 minutes.

The following intermediates were prepared using the method described in Intermediates B and C except that 2-chloro-4-nitropyridine was used as the starting material. In step 4, a 1:1 mixture of EtOAc and EtOH was used as the solvent. In step 5, purification was performed by chiral SFC using a Chiralpak ID column, 5 μm particle size, 25 cm×20 mm from Daicel Corporation on a Minigram SFC instrument from Berger Instruments (22% MeOH, 20 mM $NH_3$, 245 nm, 100 bar):

| Cmpd No. | Compound Name | LC/MS | NMR (shifts in ppm) |
|---|---|---|---|
| D | rel-2-(2,2-dimethyl-1,3-dioxolan-4-yl)pyridin-4-amine (first eluting peak by SFC on Chiralpak ID column, rt = 2.72 min) | ESI-MS m/z calc. 194.10553, found 195.2 $(M + 1)^+$; Retention time: 0.41 minutes | $^1H$ NMR (500 MHz, DMSO-$d_6$) δ 7.90 (d, J = 5.6 Hz, 1H), 6.63 (d, J = 2.3 Hz, 1H), 6.36 (dd, J = 5.6, 2.3 Hz, 1H), 6.05 (s, 2H), 4.89 (t, J = 6.8 Hz, 1H), 4.28 (dd, J = 8.1, 6.8 Hz, 1H), 3.74 (dd, J = 8.1, 6.9 Hz, 1H), 1.43 (s, 3H), 1.38 (s, 3H) ppm. |
| E | rel-2-(2,2-dimethyl-1,3-dioxolan-4-yl)pyridin-4-amine (second eluting peak by SFC on Chiralpak ID column, rt = 3.56 min) | ESI-MS m/z calc. 194.10553, found 195.2 $(M + 1)^+$; Retention time: 0.41 minutes | $^1H$ NMR (500 MHz, DMSO-$d_6$) δ 7.90 (d, J = 5.6 Hz, 1H), 6.63 (d, J = 2.3 Hz, 1H), 6.36 (dd, J = 5.6, 2.3 Hz, 1H), 6.05 (s, 2H), 4.89 (t, J = 6.8 Hz, 1H), 4.28 (dd, J = 8.1, 6.8 Hz, 1H), 3.75 (dd, J = 8.1, 6.9 Hz, 1H), 1.43 (s, 3H), 1.38 (s, 3H) ppm. |

The following intermediate was prepared using the method described in Intermediates B and C except that 2-chloro-4-nitropyridine and 4,4,5,5-tetramethyl-2-(prop-1-en-2-yl)-1,3,2-dioxaborolane were used as the starting materials in step 1. In step 4, a 1:1 mixture of EtOAc and EtOH was used as the solvent. Step 5 was not carried out:

| Cmpd No. | Compound Name | LC/MS | NMR (shifts in ppm) |
|---|---|---|---|
| F | rac-2-(2,2,4-trimethyl-1,3-dioxolan-4-yl)pyridin-4-amine | ESI-MS m/z calc. 208.1212, found 209.0 $(M + 1)^+$; Retention time: 1.75 minutes | $^1H$ NMR (400 MHz, DMSO-$d_6$) δ 7.89 (d, J = 5.5 Hz, 1H), 6.74 (d, J = 2.3 Hz, 1H), 6.31 (dd, J = 5.5, 2.3 Hz, 1H), 6.00 (s, 2H), 4.16 (d, J = 8.4 Hz, 1H), 3.92 (d, J = 8.4 Hz, 1H), 1.42 (d, J = 3.5 Hz, 6H), 1.29 (s, 3H) ppm. |

Intermediate G 6-(((tert-butyldimethylsilyl)oxy)methyl)pyridin-3-amine

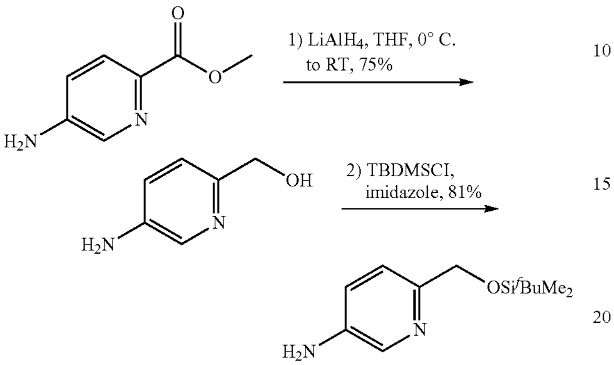

G

Step 1:

Lithium aluminium hydride (120 mL of 2 M, 240.00 mmol) was added at 0° C. under argon to a stirred suspension of methyl 5-aminopicolinate (21.05 g, 138.35 mmol) in dry THF (400 mL). The suspension was stirred at ambient temperature overnight then heated at 90° C. for 6 h. The reaction was left standing at room temperature for 30 h, after which time it was cooled back down to 0° C. The reaction was quenched by successive addition of water (9.3 mL, dropwise), 15% aqueous NaOH (9.3 mL) and then more water (28 mL). A white precipitate was filtered off, washing with additional THF (300 mL). The filtrate was concentrated in vacuo to give (5-aminopyridin-2-yl)methanol (16.1 g, 75%) as a brown oil, which was used in the next step without additional purification. $^1H$ NMR (400 MHz, DMSO-$d_6$) δ 7.81 (d, J=2.7 Hz, 1H), 7.06 (d, J=8.2 Hz, 1H), 6.89 (dd, J=8.5, 2.5 Hz, 1H), 5.11 (s, 2H), 4.34 (s, 2H) ppm; alcohol OH not observed.

Step 2:

Imidazole (1.97 g, 28.938 mmol) was added to a mixture of (5-aminopyridin-2-yl)methanol (3.65 g, 18.641 mmol) and tert-butylchlorodimethylsilane (3.41 g, 22.624 mmol) in THF (60 mL). The mixture was stirred at room temperature for 17 h. The THF layer was decanted off and the oily lower phase was dissolved in water (20 mL) and extracted with ethyl acetate (2×20 mL). The combined organic phases were washed with brine (10 mL), dried ($Na_2SO_4$), filtered and concentrated in vacuo. The oily residue (5.8 g) was taken up in a 1 to 1 mixture of ethyl acetate and heptane (30 mL). The precipitate was removed by filtration. The filtrate was concentrated in vacuo. Purification by flash chromatography ($SiO_2$, 25 to 75% ethyl acetate in heptane) gave 6-(((tert-butyldimethylsilyl)oxy)methyl)pyridin-3-amine (3.92 g, 81%) as a low-melting white solid. $^1H$ NMR (400 MHz, Chloroform-d) δ 8.00 (d, J=2.7 Hz, 1H), 7.27-7.25 (d, 1H), 7.02 (d, J=2.7 Hz, 1H), 4.72 (s, 2H), 3.82-2.92 (br s, 2H), 0.93 (s, 9H), 0.08 (s, 6H) ppm. ESI-MS m/z calc. 238.1501, found 239.5 $(M+1)^+$; Retention time: 0.86 minutes.

Intermediate H (R)-4,4,4-trifluoro-3-hydroxy-3-methylbutan-2-one

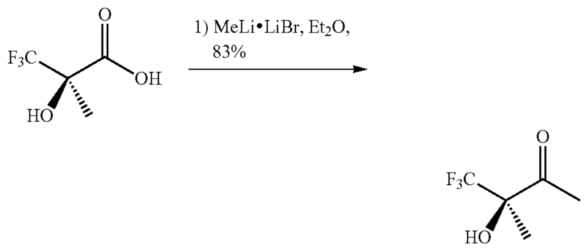

H

Step 1:

A jacketed glass reactor, dried and placed under nitrogen atmosphere, was charged with (R)-3,3,3-trifluoro-2-hydroxy-2-methylpropanoic acid (1.0 kg, 6.3261 mol) and diethyl ether (10 L). Methyllithium lithium bromide complex (3.4 L of 1.5 M in $Et_2O$, 5.1000 mol) was added slowly with evolution of gas and heat formation. The reactor was cooled to maintain a temperature of approximately 16° C. Then methyllithium with lithium bromide (6.1 L of 2.2 M in $Et_2O$, 13.420 mol) was added slowly. After addition of a total of 2 equivalents, the evolution of gas stopped and the rate of addition was decreased. The mixture was stirred overnight at ambient temperature. The reaction mixture was cooled to 0° C. and transferred to an extraction flask carrying a mixture of water (6 L), ice (2 L) and brine (2 L). The mixture was neutralized by the addition of citric acid (1.6 kg, 960.96 mL, 8.3280 mol) and was stirred for 30 min. The aqueous phase was separated and extracted with diethyl ether (2×2.5 L). The combined organic layers were concentrated in vacuo to approximately 2 L. The distillate was colored yellow and consisted of 0.8% w/w product. After further distillation, only 25 g of product was recovered from the distillate. The distillation residue was further concentrated in a distillation setup with vigreux (30 cm height) at normal pressure. The distillation was continued at reduced pressure (770 mbar) and the pressure was gradually lowered (until 200 mbar) with the collection flask cooled in ice and a cold trap between pump and setup. Mixed fractions were collected until the distillation temperature reached 71° C. The major fraction (590 g) was then collected until the distillation temperature dropped below 70° C. The combined mixed fractions were poured in brine and extracted with diethyl ether (3×75 mL). The combined organic layers were dried ($Na_2SO4$), filtered and concentrated in a distillation setup at normal pressure. The product was distilled at reduced pressure (200 mbar) to give the product as a colourless oil (198 g). The collected mixed fractions were redistilled to afford more product (44.25 g). All portions of product were combined (857 g), dried by addition of potassium carbonate (52 g) and left standing for 6 h. The water level dropped below detectable level and the mixture was filtered over glass filter to give (R)-4,4,4-trifluoro-3-hydroxy-3-methylbutan-2-one (815 g, 83%) as a colourless oil (815 g). $^1H$ NMR (300 MHz, Chloroform-d) δ 4.33 (s, 1H), 2.40 (d, J=1.1 Hz, 3H), 1.57 (d, J=1.1 Hz, 3H) ppm. $^{19}F$ NMR (282 MHz, Chloroform-d) δ −77.96 ppm.

Example 6

E-VIPR Assay Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential,* 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human $Na_V$ 1.8 with full channel activity were seeded into microtiter 384-well plates, pre-coated with matrigel, at a density of 25,000 cells per well. 2.5-5% KIR2.1 Bacmam virus was added to the final cell suspension before seeding into cell plates. HEK cells were grown in Dulbecco's Modified Eagle's Medium (DMEM) supplemented with 10% FBS (Fetal Bovine Serum, qualified; Sigma #F4135), 1% NEAA (Non-Essential Amino Acids, Gibco #11140), 1% HEPES (Gibco #15630), 1% Pen-Strep (Penicillin-Streptomycin; Gibco #15140) and 5 μg/ml Blasticidin (Gibco #R210-01). Cells were expanded in vented cap cell culture flasks, with 90-95% humidity and 5% $CO_2$.

Reagents and Stock Solutions:

100 mg/mL Pluronic F-127 (Sigma #P2443), in dry DMSO

Compound Plates: Corning 384-well Polypropylene Round Bottom #3656

Cell Plates: 384-well tissue culture treated plates (Greiner #781091-2B)

2.5-5% KIR 2.1 Bacmam virus (produced in-house), prepared as described in Section 3.3 of J. A. Fornwald et al., *Gene Expression in Mammalian Cells Using BacMam, a Modified Baculovirus System,* 1350 Methods in Molecular Biology 95-116 (2016), the entire contents of which are incorporated by reference. The concentration used can be dependent on viral titer of each batch.

5 mM $DiSBAC_6(3)$, a voltage sensitive oxonol acceptor (CAS number 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione), in dry DMSO. The preparation of $DiSBAC_6(3)$ is analogous to that of $DiSBAC_4(3)$ as described in *Voltage Sensing by Fluorescence Resonance Energy Transfer in Single Cells*, Gonzalez, J. E. and Tsien, R. Y. (1995) *Biophys. J.* 69, 1272-1280.

5 mM CC2-DMPE, a commercially available membrane-bound coumarin phospholipid FRET donor (ThermoFisher Scientific catalog number K1017, CAS number 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl] ester) was prepared in dry DMSO. See also, *Improved indicators of cell membrane potential that use fluorescence resonance energy transfer*, Gonzalez, J. E. and Tsien, R. Y. (1997) *Chem. Biol.* 4, 269-277.

Voltage Assay Background Suppression Compound (VABSC-1) is prepared in $H_2O$ (89-363 mM, range used to maintain solubility)

Human Serum (HS, Millipore #S1P1-01KL, or Sigma SLBR5469V and SLBR5470V as a 50%/50% mixture, for 25% assay final concentration)

Bath 1 Buffer:

Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath 1 Buffer:

Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2× Concentration):

Bath 1 Buffer containing 0.5% β-cyclodextrin (made fresh prior to each use, Sigma #C4767), 8 μM CC2-DMPE and 2 μM $DiSBAC_6(3)$. The solution was made by adding 10% Pluronic F127 stock equal to combined volumes of CC2-DMPE and $DiSBAC_6(3)$. The order of preparation was first mix Pluronic and CC2-DMPE, then add $DiSBAC_6(3)$, then while vortexing add Bath1/β-Cyclodextrin.

Compound Loading Buffer (2× concentration): Na/TMA Cl Bath1 Buffer containing HS (omitted in experiments run in the absence of human serum (HS)) 50%, VABSC-1 1 mM, BSA 0.2 mg/ml (in Bath-1), KCl 9 mM, DMSO 0.625%.

Assay Protocol (7 key Steps):

1) To reach the final concentration in each well, 375 nL of each compound was pre-spotted (in neat DMSO) into polypropylene compound plates at 240× desired final concentration from an intermediate stock concentration of 0.075 mM, in an 11 point dose response, 3-fold dilution, resulting in a top dose of 300 nM final concentration in the cell plate. Vehicle control (neat DMSO), and positive control (an established $Na_V$1.8 inhibitor, 25 μM final in assay in DMSO) were added manually to the outermost columns of each plate respectively. The compound plate was backfilled with 45 μL per well of Compound Loading Buffer resulting in a 240 fold dilution of compound following a 1:1 transfer of compound into the cell plate (see Step 6). Final DMSO concentration for all wells in the assay was 0.625% (0.75% DMSO was supplemented to the Compound Loading Buffer for a final DMSO concentration of 0.625%). This assay dilution protocol was adjusted to enable a higher dose range to be tested in the presence of HS or if the final assay volume was altered.
2) Hexyl Dye Solution was prepared.
3) Cell plates were prepared. On the day of the assay, the media was aspirated, and the cells were washed three times with 80 μL of Bath-1 buffer, maintaining 25 μL residual volume in each well.
4) 25 μL per well of Hexyl Dye Solution was dispensed into the cell plates. The cells were incubated for 20 minutes at room temperature or ambient conditions in darkness.

5) 45 μL per well of Compound Loading Buffer was dispensed into compound plates.

6) The cell plates were washed three times with 80 μL per well of Bath-1 Buffer, leaving 25 μL of residual volume. Then 25 μL per well from compound plate was transferred to each cell plate. The mixture was incubated for 30 minutes at room temperature/ambient conditions.

7) The cell plate containing compound was read on E-VIPR using the current-controlled amplifier to deliver stimulation wave pulses using a symmetrical biphasic waveform. The user-programmed electrical stimulus protocols were 1.25-4 Amps and 4 millisecond pulse width (dependent on electrode composition) were delivered at 10 Hz for 10 seconds. A pre-stimulus recording was performed for each well for 0.5 seconds to obtain the un-stimulated intensities baseline. The stimulatory waveform was followed by 0.5 seconds of post-stimulation recording to examine the relaxation to the resting state. All E-VIPR responses were measured at 200 Hz acquisition rate.

Data Analysis:

Data were analyzed and reported as normalized ratios of emission intensities measured in the 460 nm and 580 nm channels. The response as a function of time was reported as the ratios obtained using the following formula:

$$R(t) = \frac{(\text{intensity}_{460\ nm})}{(\text{intensity}_{580\ nm})}$$

The data were further reduced (i.e. normalized) by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound (i.e. the maximum amplitude of the ratio response or number of action potential peaks, at the beginning of the pulse train in the presence of the test compound). Using this analysis protocol, dose response curves were plotted and $IC_{50}$ values were generated for various compounds of the present invention as reported below.

Compounds having a measured $IC_{50}$ value less than 0.01 μM in the E-VIPR Assay described above include: 1, 4, 5, 7, 24, and 25.

Compounds having a measured $IC_{50}$ value less than 0.1 μM and greater than or equal to 0.01 μM in the E-VIPR Assay described above include: 6 and 18.

Compounds having a measured $IC_{50}$ value less than 1 μM and greater than or equal to 0.1 μM in the E-VIPR Assay described above include: 2, 8, 13, 14, 20*, and 22*.

Compounds having a measured $IC_{50}$ value greater than or equal to 1 μM in the E-VIPR Assay described above include: 3, 9*, 10*, 11*, 12*, 15, 16, 17, 19*, 21*, and 23*.

Compound numbers followed by "*" indicate that the assay was performed in the presence of human serum, as described above.

Many modifications and variations of the embodiments described herein may be made without departing from the scope, as is apparent to those skilled in the art. The specific embodiments described herein are offered by way of example only.

What is claimed is:

1. A compound of formula (I)

I

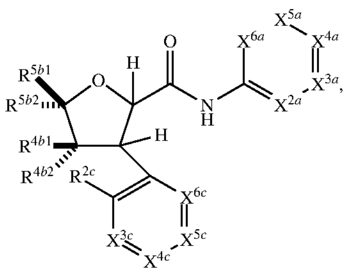

or a pharmaceutically acceptable salt thereof, wherein:

$X^{2a}$ is N, $N^+$—$O^-$, or C—$R^{2a}$;

$X^{3a}$ is N, $N^+$—$O^-$, C—$R^{3a}$, C—$CONR_2$, or C—$CH_{1-n}(R^A)(OH)(CH_2OH)_n$;

$X^{4a}$ is N, $N^+$—$O^-$, C—$R^{4a}$, C—$CONR_2$, or C—$CH_{1-n}(R^A)(OH)(CH_2OH)_n$;

$X^{5a}$ is N, $N^+$—$O^-$, or C—$R^{5a}$;

$X^{6a}$ is N, $N^+$—$O^-$, or C—$R^{6a}$;

each R is independently H or $C_1$-$C_6$ alkyl;

n is 0 or 1;

$R^A$ is H or $CH_3$;

$R^{2a}$, $R^{3a}$, $R^{4a}$, $R^{5a}$, and $R^{6a}$ are each independently H, halo, $C_1$-$C_6$ alkyl, or $C_1$-$C_6$ haloalkyl;

one of $R^{4b1}$ and $R^{4b2}$ is OH, $C_1$-$C_6$ alkoxy, or $C_1$-$C_6$ haloalkoxy, and the other is H;

$R^{5b1}$ and $R^{5b2}$ are each independently H, $C_1$-$C_6$ alkyl, $C_3$-$C_6$ cycloalkyl, or $C_1$-$C_6$ haloalkyl;

$X^{3c}$ is N or C—$R^{3c}$;

$X^{4c}$ is N or C—$R^{4c}$;

$X^{5c}$ is N or C—$R^{5c}$;

$X^{6c}$ is N or C—$R^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;

$L^1$ is a bond or O;

$L^2$ is a bond or $C_1$-$C_6$ alkylene;

$R^{3c}$ is H, halo, $C_1$-$C_6$ alkyl, or $C_1$-$C_6$ haloalkyl;

$R^{4c}$ is H, halo, $C_1$-$C_6$ alkyl, or $C_1$-$C_6$ haloalkyl;

$R^{5c}$ is H, halo, $C_1$-$C_6$ alkyl, or $C_1$-$C_6$ haloalkyl; and $R^{6c}$ is H, halo, $C_1$-$C_6$ alkyl, or $C_1$-$C_6$ haloalkyl;

provided that no more than two of $X^{2a}$, $X^{3a}$, $X^{4a}$, $X^{5a}$, and $X^{6a}$ are N or $N^+$—$O^-$;

provided that at least one of $X^{3a}$ and $X^{4a}$ is N, $N^+$—$O^-$, C—$R^{3a}$, or C—$R^{4a}$, and provided that no more than one of $X^{3c}$, $X^{4c}$, $X^{5c}$, and $X^{6c}$ is N.

2. The compound of claim 1, wherein the compound has formula (I-A)

I-A

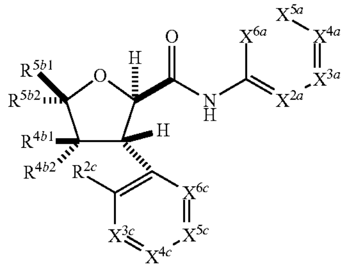

or a pharmaceutically acceptable salt thereof.

3. The compound of claim 1, wherein the compound has formula (I-A-1)

I-A-1

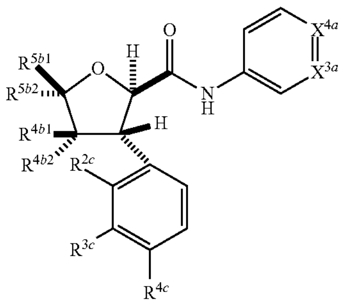

or a pharmaceutically acceptable salt thereof.

4. The compound of claim 1, wherein the compound has formula (I-B)

I-B

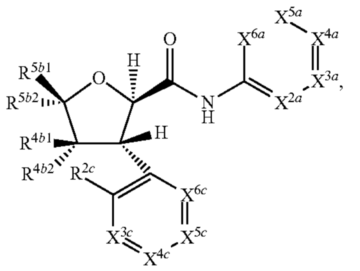

or a pharmaceutically acceptable salt thereof.

5. The compound of claim 1, wherein the compound has formula (I-B-1)

I-B-1

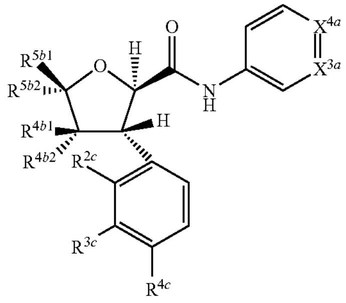

or a pharmaceutically acceptable salt thereof.

6. The compound of claim 1, or the pharmaceutically acceptable salt thereof, wherein $X^{2a}$ is C—$R^{2a}$, and $R^{2a}$ is H.

7. The compound of claim 1, or the pharmaceutically acceptable salt thereof, wherein $X^{3a}$ is N, C—$CONR_2$, or C—$CH_{1-n}(R^A)(OH)(CH_2OH)_n$.

8. The compound of claim 1, or the pharmaceutically acceptable salt thereof, wherein $X^{4a}$ is N, C—$CONR_2$, or C—$CH_{1-n}(R^A)(OH)(CH_2OH)_n$.

9. The compound of claim 1, or the pharmaceutically acceptable salt thereof, wherein one of $X^{3a}$ and $X^{4a}$ is N and the other is C—$CONR_2$, or C—$CH_{1-n}(R^A)(OH)(CH_2OH)_n$.

10. The compound of claim 1, or the pharmaceutically acceptable salt thereof, wherein $R^{5b1}$ is $C_1$-$C_6$ alkyl or $C_1$-$C_6$ haloalkyl; and/or $R^{5b2}$ is $C_1$-$C_6$ alkyl or $C_1$-$C_6$ haloalkyl.

11. The compound of claim 1, or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy; and/or $R^{3c}$ is halo or $C_1$-$C_6$ alkyl; and/or $R^{4c}$ is halo; and/or $R^{5c}$ is H; and/or $R^{6c}$ is H.

12. The compound of claim 1, or a pharmaceutically acceptable salt thereof, wherein $R^{4b2}$ is $C_1$-$C_6$ alkoxy; or $R^{4b1}$ is $C_1$-$C_6$ alkoxy.

13. A compound selected from:

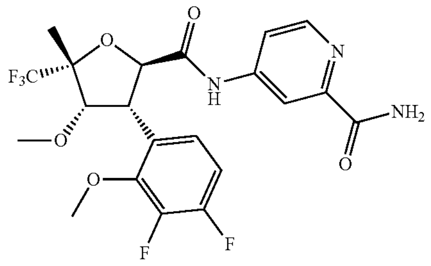

4-((2R, 3R, 4S, 5R)-3-(3, 4-difluoro-2-methoxyphenyl)-4-methoxy-5-methyl-5-(trifluoromethyl)tetrahydrofuran-2-carboxamido)picolinamide -continued

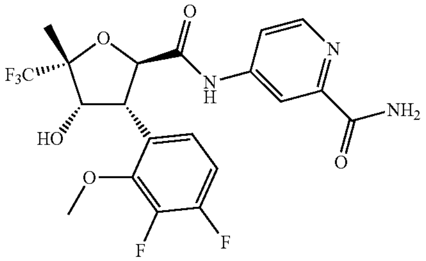

4-((2R, 3R, 4S, 5R)-3-(3, 4-difluoro-2-methoxyphenyl)-4-hydroxy-5-methyl-5-(trifluoromethyl)tetrahydrofuran-2-carboxamido)picolinamide

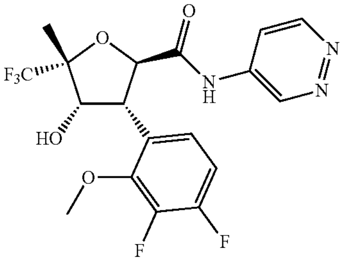

(2R, 3R, 4S, 5R)-3-(3, 4-difluoro-2-methoxyphenyl)-4-hydroxy-5-methyl-N-(pyridazin-4-yl)-5-(trifluoromethyl)tetrahydrofuran-2-carboxamide

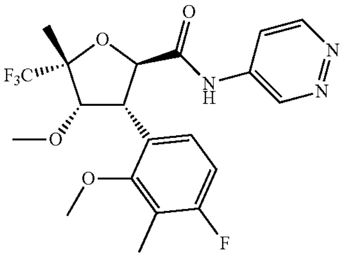

(2R, 3R, 4S, 5R)-3-(3, 4-difluoro-2-methoxyphenyl)-4-methoxy-5-methyl-N-(pyridazin-4-yl)-5-(trifluoromethyl)tetrahydrofuran-2-carboxamide

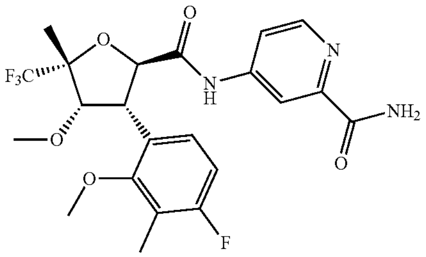

4-((2R, 3R, 4S, 5R)-3-(4-fluoro-2-methoxy-3-methylphenyl)-4-methoxy-5-methyl-5-(trifluoromethyl)tetrahydrofuran-2-carboxamido)picolinamide -continued

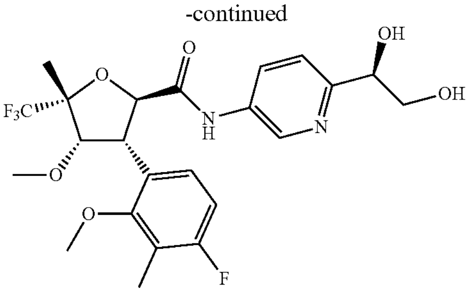

(2R, 3R, 4S, 5R)-N-(6-((R)-1, 2- dihydroxyethyl)pyridin-3-yl)-3-(4-fluoro-2-methoxy-3-methylphenyl)-4-methoxy-5-methyl-5-(trifluoromethyl)tetrahydrofuran-2-carboxamide

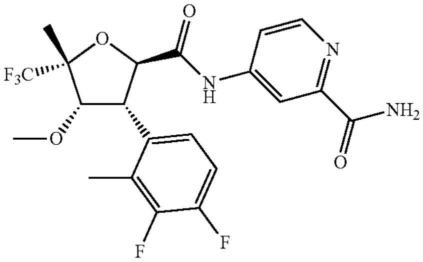

4-((2R, 3R, 4S, 5R)-3-(3, 4-difluoro-2-methoxyphenyl)-4-methoxy-5-methyl-5-(trifluoromethyl)tetrahydrofuran-2-carboxamido)picolinamide

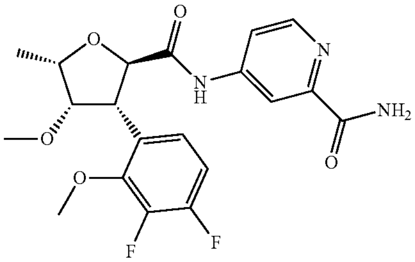

4-((2R, 3R, 4S, 5R)-3-(3, 4-difluoro-2-methoxyphenyl)-4-methoxy-5-methyltetrahydrofuran-2-carboxamido)picolinamide

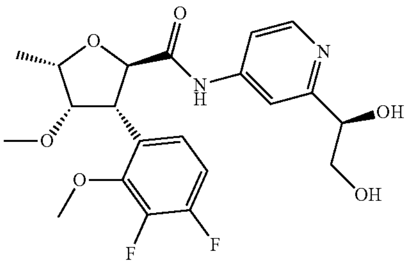

(2R, 3R, 4S, 5S)-3-(3, 4-difluoro-2-methoxyphenyl)-N-(2-((R)-1, 2-dihydroxyethyl)pyridin-4-yl)-4-methoxy-5-methyltetrahydrofuran-2-carboxamide -continued

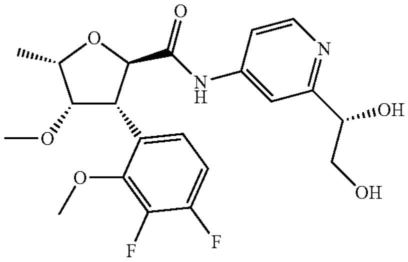

(2R, 3R, 4S, 5S)-3-(3, 4-difluoro-2-methoxyphenyl)-N-(2-((S)-1, 2-dihydroxyethyl)pyridin-4-yl)-4-methoxy-5-methyltetrahydrofuran-2-carboxamide

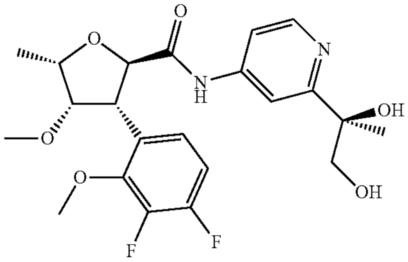

(2R, 3R, 4S, 5S)-3-(3, 4-difluoro-2-methoxyphenyl)-N-(2-((R)-1, 2-dihydroxypropan-2-yl)pyridin-4-yl)-4-methoxy-5-methyltetrahydrofuran-2-carboxamide

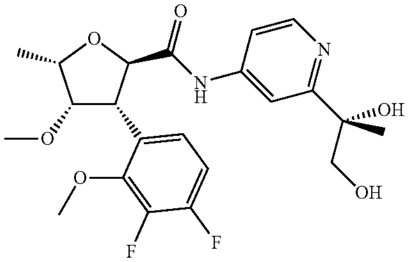

(2R, 3R, 4S, 5S)-3-(3, 4-difluoro-2-methoxyphenyl)-N-(2-((S)-1, 2-dihydroxypropan-2-yl)pyridin-4-yl)-4-methoxy-5-methyltetrahydrofuran-2-carboxamide

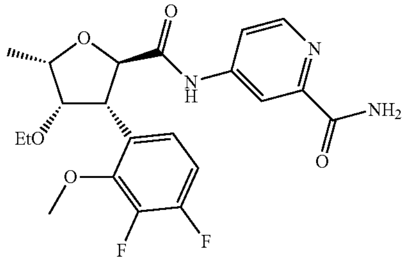

4-((2R, 3R, 4S, 5S)-3-(3, 4-difluoro-2-methoxyphenyl)-4-ethoxy-5-methyltetrahydrofuran-2-carboxamido)picolinamide -continued

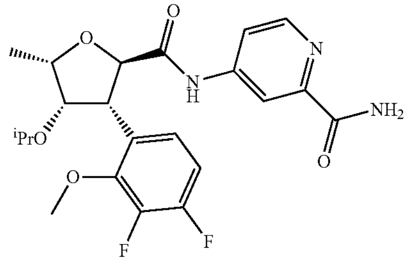

4-((2R, 3R, 4S, 5S)-3-(3, 4-difluoro-2-methoxyphenyl)-4-isopropoxy-5-methyltetrahydrofuran-2-carboxamido)picolinamide

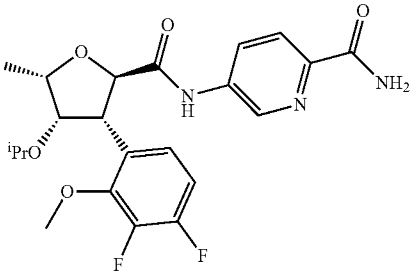

5-((2R, 3R, 4S, 5S)-3-(3, 4-difluoro-2-methoxyphenyl)-4-isopropoxy-5-methyltetrahydrofuran-2-carboxamido)picolinamide

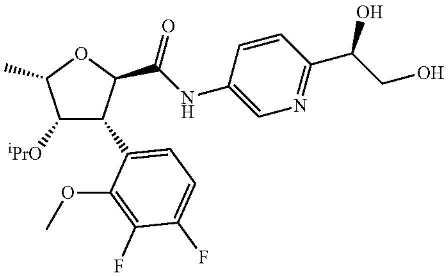

(2R, 3R, 4S, 5S)-3-(3, 4-difluoro-2-methoxyphenyl)-N-(6-((R)-1 ,2-dihydroxyethyl)pyridin-3-yl)-4-isopropoxy-5-methyltetrahydrofuran-2-carboxamide

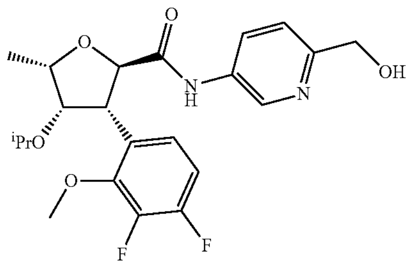

(2R, 3R, 4S, 5S)-3-(3, 4-difluoro-2-methoxyphenyl)-N-(6-(hydroxymethyl)pyridin-3-yl)-4-isopropoxy-5-methyltetrahydrofuran-2-carboxamide -continued

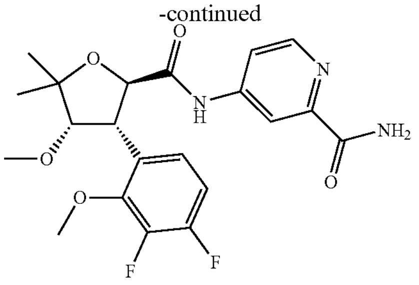

4-((2R, 3R, 4S)-3-(3, 4-difluoro-2-methoxyphenyl)-4-methoxy-5, 5-dimethyltetrahydrofuran-2-carboxamido)picolinamide

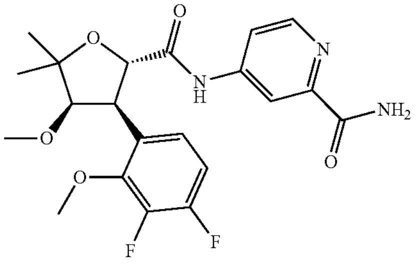

4-((2S, 3S, 4R)-3-(3, 4-difluoro-2-methoxyphenyl)-4-methoxy-5, 5-dimethyltetrahydrofuran-2-carboxamido)picolinamide

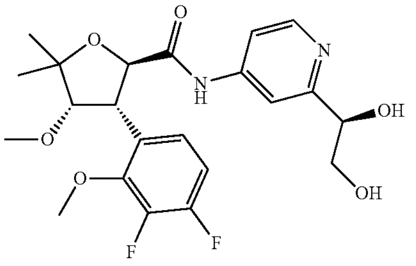

(2R, 3R, 4S)-3-(3, 4-difluoro-2-methoxyphenyl)-N-(2-((R)-1, 2-dihydroxyethyl)pyridin-4-yl)-4-methoxy-5, 5-dimethyltetrahydrofuran-2-carboxamide

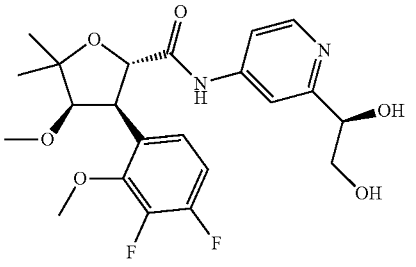

(2S, 3S, 4R)-3-(3, 4-difluoro-2-methoxyphenyl)-N-(2-((S)-1, 2-dihydroxyethyl)pyridin-4-yl)-4-methoxy-5, 5-dimethyltetrahydrofuran-2-carboxamide -continued

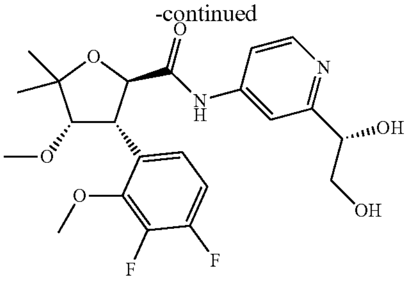

(2R, 3R, 4S)-3-(3, 4-difluoro-2-methoxyphenyl)-N-(2-((S)-1, 2-dihydroxyethyl)pyridin-4-yl)-4-methoxy-5, 5-dimethyltetrahydrofuran-2-carboxamide

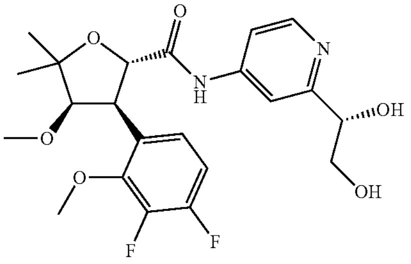

(2S, 3S, 4R)-3-(3, 4-difluoro-2-methoxyphenyl)-N-(2-((S)-1, 2-dihydroxyethyl)pyridin-4-yl)-4-methoxy-5, 5-dimethyltetrahydrofuran-2-carboxamide

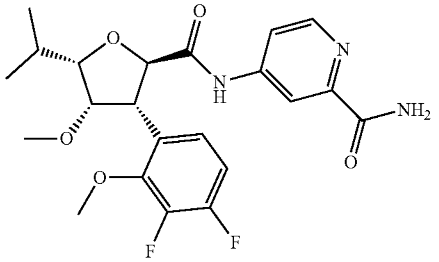

4-((2R, 3R, 4S, 5S)-3-(3, 4-difluoro-2- methoxyphenyl)-5-isopropyl-4- methoxytetrahydrofuran-2-carboxamido)picolinamide

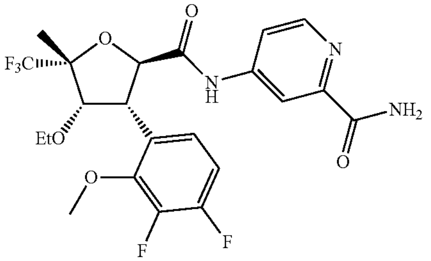

4-((2R, 3R, 4S, 5R)-3-(3,4-difluoro-2-methoxyphenyl)-4-ethoxy-5-methyl-5-(trifluoromethyl)tetrahydrofuran-2-carboxamido)picolinamide or a pharmaceutically acceptable salt thereof.

14. The compound of claim 13 in non-salt form.

15. A pharmaceutical composition comprising: (i) a therapeutically effective amount of the compound of claim 1 and one or more pharmaceutically acceptable carriers or vehicles; or (ii) the compound of claim 1 and one or more pharmaceutically acceptable carriers or vehicles.

16. A method of inhibiting a voltage-gated sodium channel in a subject, wherein the voltage-gated sodium channel is $Na_V1.8$, comprising administering to the subject the compound of claim 1, or a pharmaceutically acceptable salt thereof.

17. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

18. The method of claim 17, where the method comprises treating or lessening the severity in the subject of one or more of neuropathic pain, musculoskeletal pain, acute pain, postsurgical pain, or visceral pain.

19. The method of claim 18, wherein the neuropathic pain comprises one or more of post-herpetic neuralgia, small-fiber neuropathy, idiopathic small-fiber neuropathy, or diabetic neuropathy.

20. The method of claim 17, wherein said subject is treated with one or more additional therapeutic agents administered concurrently with, prior to, or subsequent to treatment with the compound or pharmaceutically acceptable salt.

* * * * *